US012527698B2

(12) United States Patent
Umebayashi

(10) Patent No.: US 12,527,698 B2
(45) Date of Patent: Jan. 20, 2026

(54) METHOD FOR PRODUCING WEARABLE ARTICLE

(71) Applicant: ZUIKO CORPORATION, Osaka (JP)

(72) Inventor: Toyoshi Umebayashi, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 35 days.

(21) Appl. No.: 18/038,775

(22) PCT Filed: Aug. 23, 2021

(86) PCT No.: PCT/JP2021/030830
§ 371 (c)(1),
(2) Date: May 25, 2023

(87) PCT Pub. No.: WO2022/118506
PCT Pub. Date: Jun. 9, 2022

(65) Prior Publication Data
US 2024/0033133 A1 Feb. 1, 2024

(30) Foreign Application Priority Data
Dec. 1, 2020 (JP) ................................. 2020-199864

(51) Int. Cl.
*A61F 13/15* (2006.01)

(52) U.S. Cl.
CPC .. *A61F 13/15747* (2013.01); *A61F 13/15634* (2013.01)

(58) Field of Classification Search
CPC .......... A61F 13/15747; A61F 13/15634; A61F 13/15699; A61F 13/15707; A61F 13/15739; A61F 13/15658
See application file for complete search history.

(56) References Cited

U.S. PATENT DOCUMENTS 4,834,735 A * 5/1989 Alemany .......... A61F 13/53752 428/218
5,180,622 A * 1/1993 Berg ....................... A61L 15/60 428/326

(Continued)

FOREIGN PATENT DOCUMENTS

CA 2 391 528 5/2001
EP 0 254 476 1/1988

(Continued)

OTHER PUBLICATIONS

Extended European Search Report issued Mar. 20, 2024 in corresponding European Patent Application No. 21900262.3.

(Continued)

*Primary Examiner* — George R Koch
*Assistant Examiner* — Christopher C Caillouet
(74) *Attorney, Agent, or Firm* — Wenderoth, Lind & Ponack, L.L.P.

(57) ABSTRACT

A method for producing a wearing article includes: a step of producing a waist member including a waist body and male fasteners; a step of joining an absorber to the waist body; and a step of engaging the male fastener and a female fastener of the absorber with each other by folding the absorber in two in an orthogonal direction, then folding, in a width direction, both side portions of the waist member, in which the step of producing the absorber includes a step of producing a core by holding an SAP on a core-side first non-woven fabric so as to form a first low-density region that holds an SAP having a lower density than an SAP in a holding region for holding the SAP and that is adjacent in an orthogonal direction to both end portions of the holding region in the orthogonal direction.

14 Claims, 23 Drawing Sheets

(56) References Cited

U.S. PATENT DOCUMENTS

| | | | | |
|---|---|---|---|---|
| 5,977,014 | A * | 11/1999 | Plischke | A61F 13/535 604/378 |
| 6,508,799 | B1 | 1/2003 | Freiburger et al. | |
| 6,703,330 | B1 | 3/2004 | Marsh | |
| 8,343,127 | B1 | 1/2013 | Dimitrijevs et al. | |
| 2004/0035521 | A1 | 2/2004 | Nakakado et al. | |
| 2005/0241751 | A1 | 11/2005 | Nakakado et al. | |
| 2006/0032589 | A1 | 2/2006 | Nakakado et al. | |
| 2008/0099130 | A1 | 5/2008 | Umebayashi et al. | |
| 2011/0188985 | A1 | 8/2011 | Nakakado et al. | |
| 2011/0196331 | A1 | 8/2011 | Nakakado et al. | |
| 2011/0212818 | A1 | 9/2011 | Nakakado et al. | |
| 2011/0282315 | A1 | 11/2011 | Gustin Bergström et al. | |
| 2015/0011958 | A1 | 1/2015 | Yoshioka | |
| 2016/0235604 | A1 | 8/2016 | Ehrnsperger et al. | |
| 2021/0186777 | A1 * | 6/2021 | Di Berardino | B32B 7/05 |

FOREIGN PATENT DOCUMENTS

| | | |
|---|---|---|
| EP | 2 601 922 | 6/2013 |
| JP | 2003-509162 | 3/2003 |
| JP | 2003-527152 | 9/2003 |
| JP | 2004-223238 | 8/2004 |
| JP | 2008-73216 | 4/2008 |
| JP | 2008-154964 | 7/2008 |
| JP | 2009-118921 | 6/2009 |
| JP | 2012-61138 | 3/2012 |
| JP | 2012-510312 | 5/2012 |
| JP | 2013-75106 | 4/2013 |
| JP | 2020-120937 | 8/2020 |
| WO | 2006/068081 | 6/2006 |
| WO | 2013/168753 | 11/2013 |

OTHER PUBLICATIONS

Office Action issued Aug. 13, 2024 in Japanese Patent Application No. 2021-103374, with English-language Translation.

International Search Report issued Nov. 2, 2021 in International (PCT) Application No. PCT/JP2021/030830.

Notice of Reasons for Refusal issued Feb. 15, 2021 in Japanese Application No. 2020-199864, with English translation thereof.

Office Action issued May 21, 2024 in Japanese Patent Application No. 2021-103374, with English-language Translation.

Office Action issued Oct. 22, 2024 in corresponding Canadian Patent Application No. 3203147, 9 pages.

* cited by examiner

METHOD FOR PRODUCING WEARABLE ARTICLE

TECHNICAL FIELD

The present invention relates to a method for producing a wearing article.

BACKGROUND ART

Patent Literatures 1 to 3 disclose wearing articles that can be developed from an initial underpants-shaped form to a predetermined development form and that can be assembled from the development form to the underpants-shaped form. These wearing articles include a belt-shaped waist part disposed around a waist of a wearer, and an absorber extending from a front abdomen portion to a back portion of the wearer via a crotch portion. The waist part has elasticity that is capable of expanding and contracting along a belt-shaped width direction. The absorber is joined to the waist part and extends from the joint part so as to be orthogonal to the width direction of the waist part.

In a state before use, both end portions of the waist part are detachably engaged with a tip end portion of the absorber. Therefore, the wearing article can be worn as underpants.

When the wearing state of the wearing article is adjusted during use, the wearing article can be developed by releasing the both end portions of the waist part from the tip end portion of the absorber.

Furthermore, the wearing article can be assembled into an underpants shape by reengaging the both end portions of the waist part with the tip end portion of the absorber from the developed state.

However, in Patent Literatures 1 to 3, although the form of the wearing article can be changed between the initial underpants-shaped form and the development form, improvement in a wearing feeling in consideration of tactile sense at a part of the wearing article in direct contact with the skin is not considered. Therefore, it is required to improve the wearing feeling by improving such a part in direct contact with the skin.

CITATION LIST

Patent Literature

Patent Literature 1: JP 2008-73216 A
Patent Literature 2: JP 2003-527152 A
Patent Literature 3: U.S. Pat. No. 8,343,127 B

SUMMARY OF INVENTION

Therefore, the present invention has been made in view of the above-described problems, and an object of the present invention is to provide a method for producing a wearing article capable of changing a form between an initial underpants shape and a predetermined development form, and capable of improving a wearing feeling.

A method for producing a wearing article for solving the above problems is a method for producing a wearing article including a waist member disposed around a waist of a wearer, and an absorber joined to the waist member and extending in an orthogonal direction with respect to a width direction from a joint portion with the waist member so as to be disposed from a back portion to a front abdomen portion of the wearer via a crotch portion, the method including: a step of producing the waist member including a waist body that extends in the width direction, has elasticity capable of expanding and contracting in the width direction, and is disposed around the waist of the wearer, and first engagement portions provided on a surface facing a skin surface side of the wearer at both end portions of the waist body in the width direction; a step of producing the absorber including a core for absorbing a body fluid, a front sheet provided on the skin surface side of the wearer of the core, a back sheet provided on an outer surface side opposite to the skin surface side of the core so as to sandwich the core between the back sheet and the front sheet, and a second engagement portion provided on an outer surface opposite to a surface facing the skin surface side of the back sheet and detachable with respect to each of the first engagement portions; a step of joining the absorber to the joint portion of the waist body so as to extend in the orthogonal direction from the waist body; and a step of engaging the first engagement portion and the second engagement portion with each other by folding the absorber in two in the orthogonal direction, then folding, in the width direction, both side portions positioned on both sides in the width direction with respect to the joint portion in the waist member, in which the step of producing the absorber includes a step of producing the core by holding a water absorbent polymer on a core-side first non-woven fabric so as to form a holding region and a first low-density region that holds the water absorbent polymer having a lower density than the water absorbent polymer in the holding region and is adjacent in the orthogonal direction to both end portions of the holding region in the orthogonal direction.

It is possible to provide a method for producing a wearing article capable of changing a form between an initial underpants shape and a predetermined development form and capable of improving a wearing feeling.

DESCRIPTION OF EMBODIMENT

An embodiment of the present invention will be described below with reference to the accompanying drawings. Note that the following embodiment is an example embodying the present invention and is not intended to limit the technical scope of the present invention.

<Configuration of Refastenable Type Wearing Article>

(Overall Configuration)

A configuration of a refastenable type wearing article will be described below.

A refastenable type wearing article 1 according to the present embodiment includes a waist member 10 disposed around a waist of a wearer, and an absorber 20 disposed from a back portion to a front abdomen portion of the wearer via a crotch portion.

The waist member 10 has a waist body 16 (FIG. 4) extending in a width direction, having elasticity capable of expanding and contracting in the width direction, and disposed around the waist of the wearer, and male fasteners (first engagement portions) 12 provided on a surface facing a skin surface side of the wearer at both end portions 10*c* in the width direction of the waist body 16.

Figure 1:
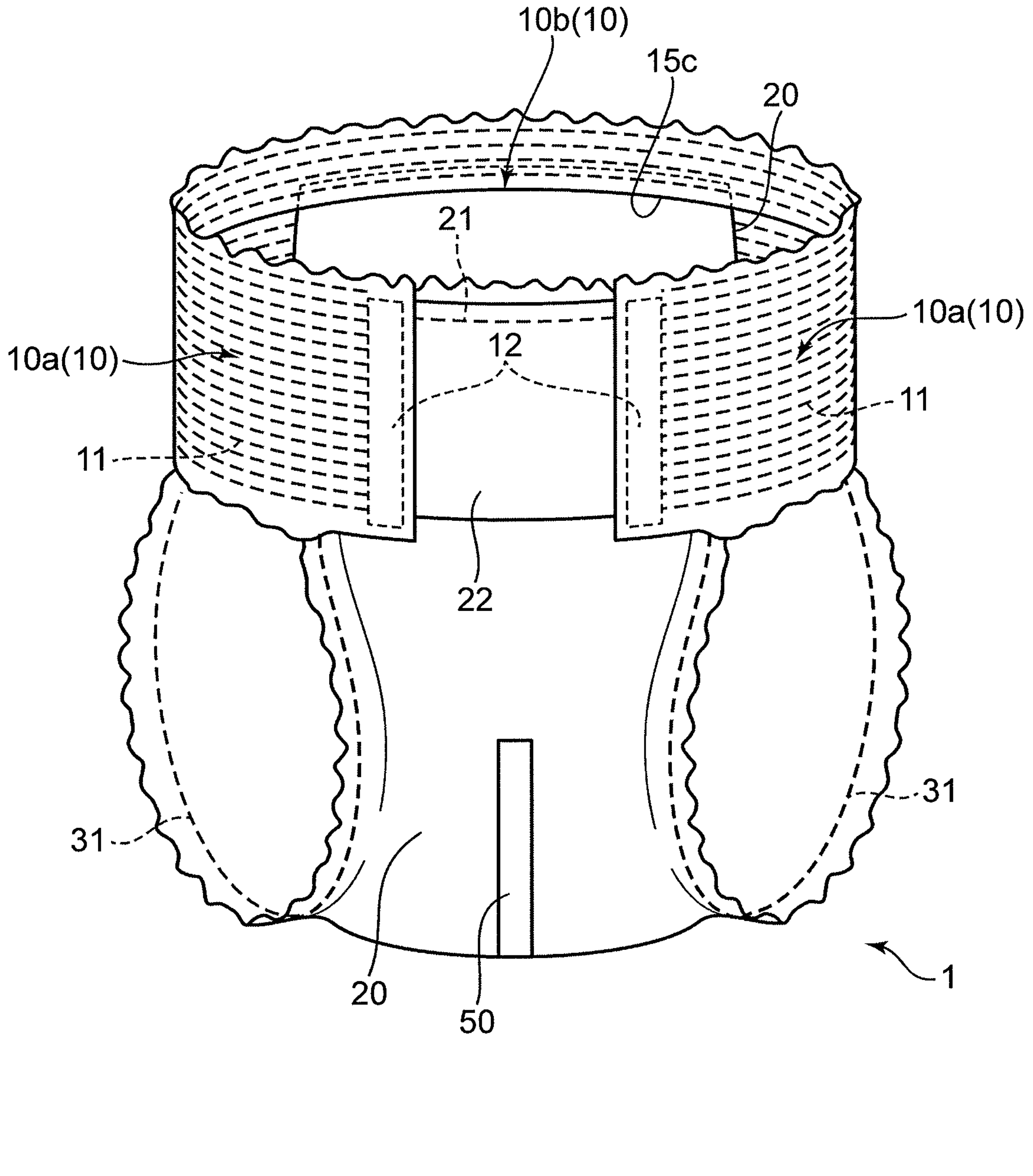
FIG. 1 is a front view illustrating an appearance of a refastenable type wearing article after assembly.
Figure 2:
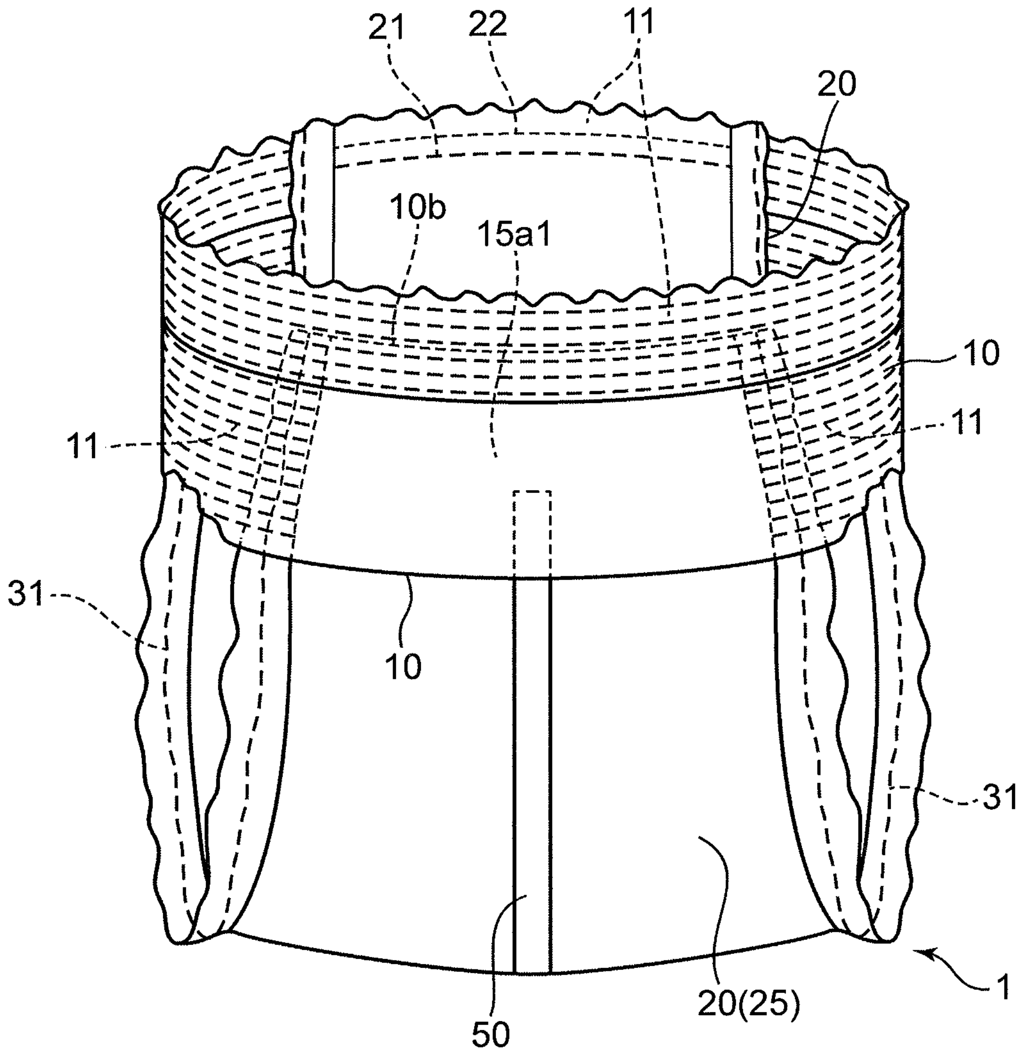
FIG. 2 is a rear view illustrating an appearance of the refastenable type wearing article after assembly.
Figure 3:
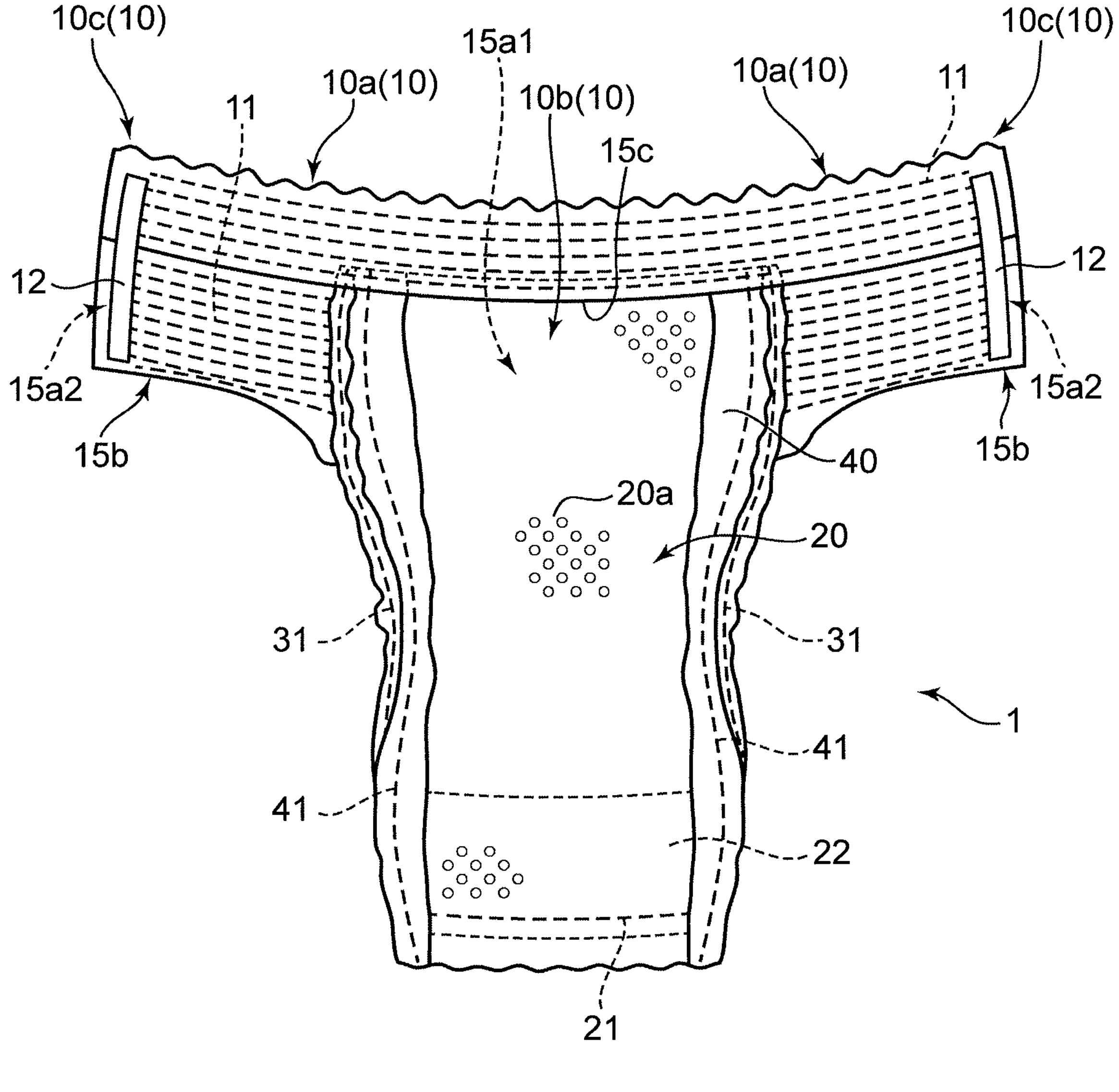
FIG. 3 is a developed view of the refastenable type wearing article.

Hereinafter, as illustrated in FIGS. 1 to 3 and the like, in the refastenable type wearing article 1, a direction in which the waist body 16 (FIG. 4) extends in the waist member 10 is referred to as waist width direction (width direction), and a direction substantially orthogonal to the waist width direction is referred to as waist orthogonal direction (orthogonal direction).

This waist body 16 includes an inner sheet 14 (FIG. 4), an outer sheet 15 (FIG. 4), and a waist elastic member 11 (FIG. 4) joined to the inner sheet 14 and the outer sheet 15 in a state of being sandwiched between the inner sheet 14 and the outer sheet 15.

The absorber 20 is a member for absorbing mainly body fluids such as urine and sweat. The absorber 20 is joined to a joint portion 10*b* (FIGS. 3 and 4) of the waist member 10. In the present embodiment, the joint portion 10*b* is a part that is at a center portion of the waist width direction of the waist member 10 and deviates downward from a waist-side edge. The absorber 20 extends in the waist orthogonal direction from the joint portion 10*b* so as to be disposed from the back portion to the front abdomen portion of the wearer via the crotch portion. The absorber 20 includes a female fastener (second engagement portion) 22 on the outer surface opposite to the surface facing the skin surface side at the tip end portion in the waist orthogonal direction.

In the final form (at a stage where the wearing article is used for the first time), the refastenable type wearing article 1 having such a configuration is folded in a state where the male fastener 12 and the female fastener 22 are engaged with each other. Specifically, in the refastenable type wearing article 1 folded as illustrated in the final step 13 of FIG. 16, the male fastener 12 and the female fastener 22 are engaged with each other in a state where the absorber 20 is folded in two in the waist orthogonal direction, and both side portions 10*a*, which are parts adjacent in the waist width direction of the joint portion 10*b* in the waist member 10, are folded in the waist width direction.

The wearer pushes and spreads the waist member 10 of the refastenable type wearing article 1 assembled in the underpants-shaped form in a state where the male fasteners 12 and the female fastener 22 are engaged, inserts the legs, and wears the wearing article 1 as underpants. The male fasteners 12 and the female fastener 22 are engaged in advance in the refastenable type wearing article 1, the engagement of the both fasteners 12 and 22 can be released to develop the wearing article 1 into the form illustrated in FIG. 3. Furthermore, engagement and release of the both fasteners 12 and 22 are repeated when the wearing article 1 is adapted to the wearer and when the wearing article 1 is replaced.

In contrast to such the refastenable type wearing article 1, an open type wearing article is folded in a state where the male fasteners 12 and the female fastener 22 are not engaged in the final form (at a stage where the wearing article is used for the first time). Specifically, in the open type wearing article, for example, in a state where the both side portions 10*a* of the waist member 10 of the wearing article in the development form of FIG. 3 are folded in the waist width direction so as to face the skin surface side of the absorber 20, the absorber 20 is folded in the waist orthogonal direction so that the tip end portion of the absorber 20 is positioned on the waist member 10 side. That is, in the open type wearing article, the both side portions 10*a* of the waist member 10 are folded so as to be sandwiched between the joint portion 10*b* of the waist member 10 and the absorber 20. In this case, the male fasteners 12 and the female fastener 22 are not engaged.

Note that the open type wearing article may include the development form illustrated in FIG. 3.

Next, each portion of the refastenable type wearing article 1 will be further described.

(Waist Member)

The waist member 10 has the waist body 16 (FIG. 4) extending in the waist width direction, having elasticity capable of expanding and contracting in the waist width direction, and disposed around the waist of the wearer, and the male fasteners 12 provided on the surface facing the skin surface side of the wearer at the both end portions 10*c* in the waist width direction of the waist body 16. The waist body 16 includes the inner sheet (FIG. 4 and the like) 14 described later, the outer sheet (FIG. 4 and the like) 15, and the waist elastic member 11.

Here, a part of the waist body 16 to which the absorber 20 is joined is the joint portion 10*b*. In the present embodiment, as illustrated in FIG. 2, a part of the waist elastic member 11 is positioned above the joint portion 10*b* in the waist orthogonal direction.

The both side portions 10*a* of the waist body 16 are regions adjacent in the waist width direction to the joint portion 10*b*. The both side portions 10*a* include the both end portions 10*c*, which are both ends in the waist width direction of the waist body 16. At least a part of the both end portions 10*c* is a joint portion 15*a*2 (FIGS. 3 and 4) to which the male fasteners 12 are joined.

The waist body 16 has elasticity in the waist width direction as a whole. The joint portion of the waist body 16 is a part where one end portion of the absorber 20 is disposed. The joint portion 10*b* includes a core arrangement portion 15*a*1 where a core 25 constituting a part of the absorber 20 is arranged (FIG. 2). The joint portion 15*a*2 of the waist body 16 is a part where the male fasteners 12 are disposed.

The core arrangement portion 15*a*1 of the joint portion 10*b* has smaller elasticity or hardly any elasticity in the waist width direction than in the region excluding the core arrangement portion. That is, in the waist body 16, in a region excluding the core arrangement portion 15*a*1, elasticity in the waist width direction is larger than that of the core arrangement portion 15*a*1. The joint portion 15*a*2 has smaller elasticity or hardly any elasticity in the waist width direction than in the region excluding the joint portion 15*a*2. That is, in the waist body 16, in the region excluding the core arrangement portion 15*a*1 and the joint portion 15*a*2, elasticity in the waist width direction is larger than that of the joint portion 15*a*2. Due to this, the waist body 16 has elasticity in the waist width direction as a whole due to the elasticity in the waist width direction in the region excluding the core arrangement portion 15*a*1 and the joint portion 15*a*2.

Here, in the final form (at the stage when the wearing article is used for the first time), the male fasteners 12 and the female fastener 22 are engaged with each other in a state where the absorber 20 is temporarily fixed in a detachable manner in a state of being folded in two, and the refastenable type wearing article 1 is folded into the underpants-shaped form. When the wearer wears the refastenable type wearing article 1, the wearer detaches the temporary fixing in a state where the male fasteners 12 and the female fastener 22 are engaged with each other, pushes and spreads the waist member 10 of the wearing article 1, inserts the legs, and wears the wearing article 1 as underpants.

The wearing article 1 in a state where engagement of the male fasteners 12 and the female fastener 22 is released in the refastenable type wearing article 1 and brought into the development form can be wearable as follows. In a state where the joint portion 10*b* of the waist body 16 abuts against the back portion, the absorber 20 is disposed over a range from the back portion to the front abdomen portion of the wearer via the crotch portion. In this state, the both side portions 10*a* adjacent to the joint portion 10*b* of the waist body 16 are expanded to the outer surface of the tip end portion of the absorber 20 positioned in the front abdomen portion. Then, the male fasteners 12 provided in the waist body 16 and the female fastener 22 provided in the absorber 20 are engaged with each other, whereby the refastenable type wearing article 1 is worn by the wearer.

Next, the planar shape of the waist body 16 will be described. An upper edge in the waist orthogonal direction of the waist body 16 is linear substantially along the waist width direction. On the other hand, at a lower edge in the waist orthogonal direction of the waist member 10, that is, the lower edge on a groin side, is provided with a leg round curve portion 15*b* (FIGS. 3, 4, and the like) for forming a leg hole along the shape of the leg round. The leg round curve portion 15*b* has a curve shape in which the length in the waist orthogonal direction of the waist body 16 increases from the both side portions 10*a* toward the joint portion 10*b*.

Figure 4:
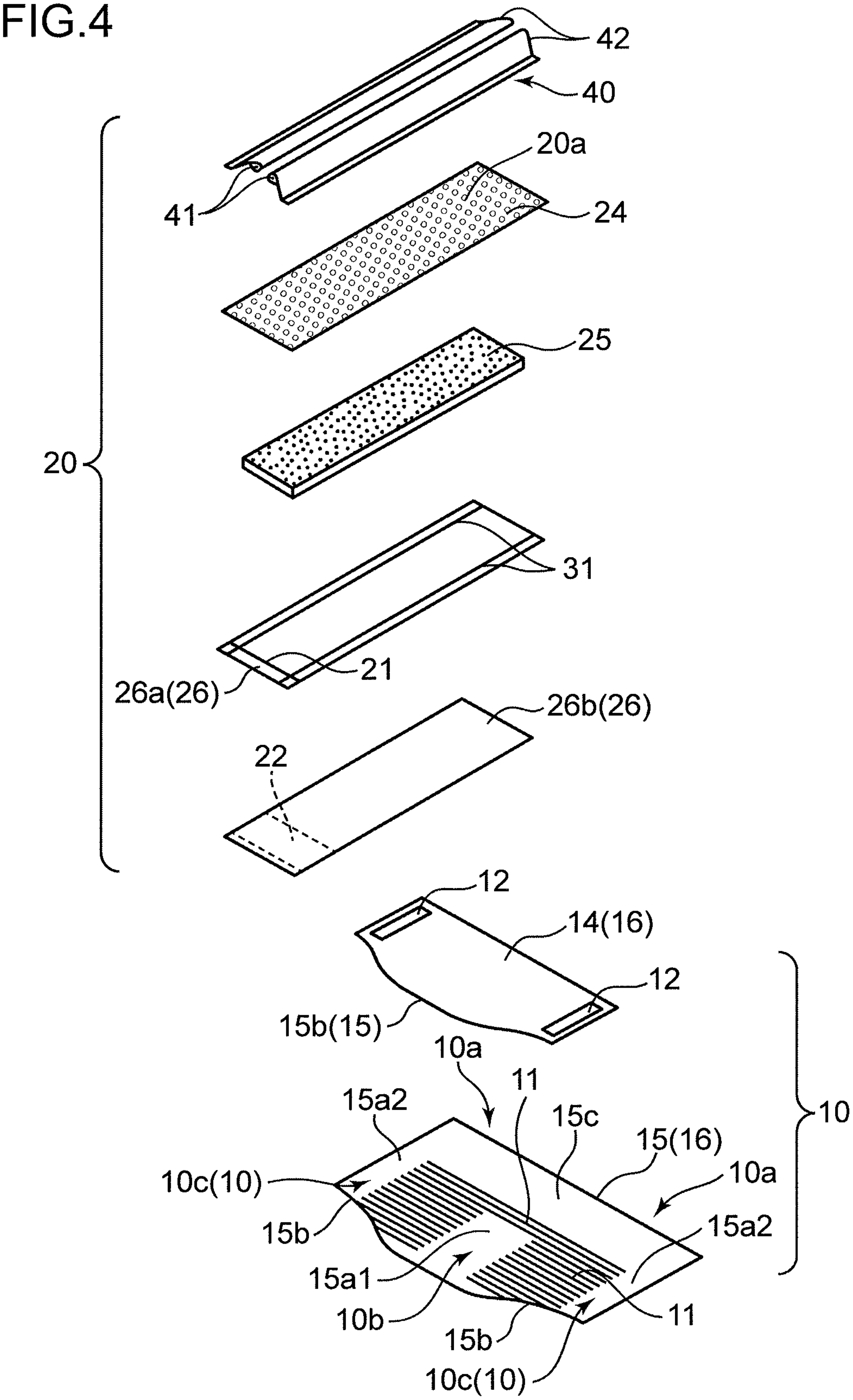
FIG. 4 is an exploded perspective view of the refastenable type wearing article.

A specific configuration of such the waist body 16 will be further described. As illustrated in FIG. 4, the waist body 16 includes the inner sheet 14 extending in the waist width direction, the outer sheet 15 extending in the waist width direction and covering an outer surface opposite to the surface facing the skin surface side of the inner sheet 14, and the waist elastic member 11 having elasticity capable of expanding and contracting along the waist width direction.

As illustrated in FIGS. 3 and 4, the inner sheet 14 is, for example, a non-woven fabric sheet, and is a belt-shaped member extending in the waist width direction. One end portion of the absorber 20 is joined to a part corresponding to the joint portion 10*b* of the inner sheet 14.

The male fasteners 12 respectively extend in the waist orthogonal direction on the surface facing the skin surface side of the both end portions 10*c* in the waist width direction of the inner sheet 14. Specifically, the male fasteners 12 are joined to the inner sheet 14. The length in the waist orthogonal direction of the male fasteners 12 is only required to be a length enough for the engagement with the female fastener 22 to be not easily released. For example, when the length in the waist orthogonal direction of the male fasteners 12 is about the same as the length in the waist orthogonal direction of the inner sheet 14, the waist body 16 can be reliably engaged with the female fastener 22 of the absorber 20 over the entire length in the waist orthogonal direction.

The outer sheet 15 includes a non-woven fabric, for example, and is a belt-shaped member extending in the waist width direction similarly to the inner sheet 14. The outer sheet 15 is disposed on the outer surface side opposite to the skin surface side of the inner sheet 14, and covers the outer surface opposite to the surface facing the skin surface side of the inner sheet 14.

The planar shape of the inner sheet 14 is the same as the planar shape of the waist body 16 described above. As illustrated in FIG. 4, the upper edge in the waist orthogonal direction of the inner sheet 14 is formed linearly along the waist width direction. The lower edge of the groin side in the waist orthogonal direction of the inner sheet 14 has the leg round curve portion 15*b* having a curve shape along the shape of the leg round. The both end portions in the waist width direction of the inner sheet 14 are linear along the waist orthogonal direction.

The lower edge of the outer sheet 15 has the leg round curve portion 15*b* having a curve shape along the shape of the leg round on the groin side, similarly to the inner sheet 14, in plan view. The outer sheet 15 has an extending portion 15*c* extending upward in the waist orthogonal direction of the inner sheet 14 in a state where the inner sheet 14 overlap so as to cover the waist elastic member 11.

As illustrated in FIG. 3 and the like, the extending portion 15*c* is joined to the inner sheet 14 and the absorber 20 in a state of being folded back so as to cover the waist elastic member 11 and so as to cover the end portion joined to the waist member 10 in the waist orthogonal direction of the absorber 20. This makes it possible to suppress discomfort caused when the end portion of the absorber 20 comes into contact with the skin. The end portion of the absorber 20 is not exposed, and the good appearance can be improved.

The waist elastic member 11 is joined to at least any one of the inner sheet 14 and the outer sheet 15 in a state where the waist elastic member 11 is expanded linearly in the waist width direction and in a state of being sandwiched between the inner sheet 14 and the outer sheet 15. Then, the waist elastic member 11 is disposed in a range from the upper end edge of the inner sheet 14 to the leg round curve portion 15*b* on the groin side in the region excluding the extending portion 15*c*. The waist elastic member 11 is subjected to weakening treatment in weakened portions 15*a*1 and 15*a*2 described later.

The leg round curve portion 15*b* constitutes a part of a leg hole in a curved shape along the shape of the groin. The waist elastic member 11 adjacent to the leg round curve portion 15*b* elastically brings a part of a peripheral edge portion of the leg hole into close contact with the upper portion of the groin, thereby improving the wearing feeling. Note that the waist elastic member 11 adjacent to the leg round curve portion 15*b* in the waist elastic member 11 may have a curved shape along the curve of the leg round curve portion 15*b*.

The waist elastic member 11 is formed of, for example, a material such as polyurethane, natural rubber, or thermoplastic resin. The shape of the waist elastic member 11 is, for example, a thread shape, a ribbon shape, a sheet shape, or the like. An elastic member constituting a leg gather 31 described later and elastic members such as a three-dimensional gather elastic member 41 and an absorber elastic member 21 have the same material and shape.

Joint of the waist elastic member 11 to the inner sheet 14 and the outer sheet 15 can be performed by adhesion using a hot melt adhesive or welding by heat sealing, but is desirably performed by ultrasonic welding. Use of ultrasonic welding can maintain flexibility of the inner sheet 14 and the outer sheet 15 as compared with a case of using an adhesive, and gives little crispy stiff tactile sense and little discomfort.

The waist elastic member 11 has elasticity in the waist width direction. Due to this, the waist elastic member 11 elastically brings the waist body 16 of the waist member 10 into close contact with the waist. In the present embodiment, the waist elastic member 11 includes a plurality of thread-shaped elastic members, extends in the waist width direction of the waist member 10, and is disposed at an interval in the waist orthogonal direction.

In the present embodiment, in the core arrangement portion 15*a*1 (also referred to as weakened portion 15*a*1) of the joint portion 10*b* of the waist member 10 to which the absorber 20 is joined, the waist elastic member 11 is subjected to the weakening treatment (see FIG. 2). In the present embodiment, the region of the joint portion 10*b* is larger than the region of the core arrangement portion 15*a*1.

Specifically, in the absorber 20, the core 25 is disposed in the center portion in the waist width direction, and the leg gather 31 is sandwiched between a front sheet 24 and a back sheet 26 in a state of being disposed along each of both edges in the waist width direction. The back sheet 26 is joined to the joint portion 10*b* of the waist member 10. Then, of the joint portion 10*b*, in the core arrangement portion 15*a*1 where at least the core 25 is arranged, the waist elastic member 11 is subjected to the weakening treatment.

On the other hand, in a part of the joint portion 10*b* excluding the core arrangement portion 15*a*1 (both edge portions of the front sheet 24 and the back sheet 26 at the part where the leg gather 31 is tucked, for example), the waist elastic member 11 is not subjected to the weakening treatment.

Specifically, in the present embodiment, as described above, a part of the waist elastic member 11 is positioned above the joint portion 10*b* in the waist orthogonal direction. That is, a part of the waist elastic member 11 is disposed between the upper end edge in the waist orthogonal direction of the waist body 16 and the joint portion 10*b*. Therefore, in the present embodiment, of the joint portion 10*b*, the waist elastic member 11 is not subjected to the weakening treatment in the three sides of the both side portions adjacent in the waist width direction to the core arrangement portion 15*a*1 and the upper side part in the waist orthogonal direction of the core arrangement portion 15*a*1.

As in the present embodiment, a part on the upper side in the waist orthogonal direction relative to the core arrangement portion 15*a*1 in the joint portion 10*b* is provided with at least any of the waist elastic member 11 in an expanded state. By joining the absorber 20 to such the joint portion 10*b*, the tip end portion on the waist member 10 side of the absorber 20 overlaps the waist elastic member 11 disposed in the upper side part. Therefore, similarly to that a free end (end portion on the side opposite to the waist member 10) in the waist orthogonal direction of the absorber 20 is capable of expanding and contracting by the absorber elastic member 21 described later, the tip end portion on the waist member 10 side of the absorber 20 is also made capable of expanding and contracting by the waist elastic member 11.

In the joint portions 15*a*2 (hereinafter, also referred to as weakened portions 15*a*2) to which the male fasteners 12 are joined in the both end portions 10*c* in the waist width direction of the waist member 10, the waist elastic member 11 is subjected to the weakening treatment.

Note that although the region of the joint portion 10*b* is larger than the region of the core arrangement portion 15*a*1 in the above description, the region of the joint portion 10*b* and the region of the core arrangement portion 15*a*1 may coincide with each other.

The joint portion 15*a*2 to which the male fastener 12 is joined is at least a part of the both end portions 10*c* of the waist member 10. However, the region of the both end portions 10*c* and the region of the joint portion 15*a*2 may coincide with each other. Furthermore, although the region of the joint portion 15*a*2 and the region of the weakened portion coincide in the present embodiment, the region of the weakened portion may be larger than the region of the joint portion 15*a*2.

The weakening treatment is a treatment of weakening the elastic force of the waist body 16 by the elastic member. The weakening treatment also includes a treatment of invalidating the elastic force of the elastic member. The weakening treatment is performed by cutting a part positioned in the core arrangement portion 15*a*1 and the joint portion 15*a*2 of the waist elastic member 11, for example. For example, by cutting the waist elastic member 11 in a state of being joined to the inner sheet 14 and the outer sheet 15 in a part other than the core arrangement portion 15*a*1 and the joint portion 15*a*2 and not being joined in the core arrangement portion 15*a*1 and the joint portion 15*a*2, the core arrangement portion 15*a*1 and the joint portion 15*a*2 can be subjected to the weakening treatment. The cutting is performed, for example, by cutting the elastic member using a blade or by fusing by applying heat to the elastic member. Since the elastic member is divided by applying the weakening treatment, the elastic force in the core arrangement portion 15*a*1 and the joint portion 15*a*2 is weakened.

The weakening treatment includes, in addition to a treatment of removing elasticity by dividing the elastic member as described above, denaturing the elastic member so that the elasticity of the elastic member decreases. Examples of the weakening treatment include a method of intermittently joining the elastic member to the non-woven fabric and cutting the elastic member between the joint portion and the joint portion. This weakens the elastic force of the elastic member in a range where the elastic member is cut.

By the weakening treatment, the elastic force of the waist body 16 by the waist elastic member 11 is weakened in the weakened portion 15*a*1 where the absorber 20 is disposed and the weakened portion 15*a*2 where the male fastener 12 is disposed. That is, the elastic force of the weakened portion 15*a*1 and the weakened portion 15*a*2 of the waist body 16 by the waist elastic member 11 is weaker than the elastic force of the part adjacent in the waist width direction to the weakened portion 15*a*1 and the weakened portion 15*a*2 in the waist body 16.

Thus, in the weakened portion 15*a*1 where the absorber 20 is disposed, the elastic force of the waist body 16 by the waist elastic member 11 is weakened. Therefore, since contraction of the core 25 joined to the weakened portion 15*a*1 of the waist body 16 can be suppressed, the back portion and the like can be reliably covered with the core 25.

In the weakened portion 15*a*2 where the male fastener 12 is disposed, the elastic force of the waist body 16 by the waist elastic member 11 is weakened. Therefore, contraction of the male fastener 12 is suppressed, and the engagement force between the male fasteners 12 and the female fastener 22 can be suppressed from being impaired.

(Absorber)

The absorber 20 is a belt-shaped member capable of absorbing body fluids such as urine, is joined to the joint portion 10*b* of the waist body 16, and extends from the joint portion 10*b* in the waist orthogonal direction. The absorber 20 is disposed from the back portion to the front abdomen portion of the wearer via the crotch portion.

The absorber 20 includes the core 25 for absorbing a body fluid, the front sheet 24 provided on the skin surface side of the wearer of the core 25, the back sheet 26 provided on the outer surface side opposite to the skin surface side of the core 25 so as to sandwich the core 25 between the back sheet 26 and the front sheet 24, and the female fastener 22 provided on the outer surface opposite to the surface facing the skin surface side of the back sheet 26 and detachably engaged with respect to the male fastener 12. The absorber 20 further includes the absorber elastic member 21, the leg gather 31, a three-dimensional gather 40, and an indicator 50.

The front sheet 24 is a belt-shaped sheet extending in the waist orthogonal direction, and is provided on the skin surface side of the wearer with respect to the core 25. The front sheet 24 is formed by laminating two of a front-side first non-woven fabric 24*a* and a front-side second non-woven fabric 24*b* (FIGS. 11, 12, and the like) having a liquid permeability of substantially the same size and joining the front-side first non-woven fabric 24*a* and the front-side second non-woven fabric 24*b*.

The front-side first non-woven fabric 24*a* has a surface facing the skin surface side of the wearer when worn, and this surface facing the skin surface side is provided with a plurality of irregularity shapes 20*a*. Note that the back surface of the front-side first non-woven fabric 24*a* has an irregularity shape opposite to the irregularity shapes 20*a* of the front surface. The shape of the concave part and the convex part forming the irregularity shape 20*a* is not particularly limited, and is a circular shape, an elliptical shape, a polygonal shape, or the like in plan view, for example. The size of the concave part and the convex part is only required to be a size enough to give a pleasant feeling to the skin surface, such as being capable of suppressing sticking to the skin surface due to contact, and is about 3 to 5 mm in plan view in a case of a circular shape, for example.

As described above, the front-side first non-woven fabric 24*a* on the skin surface side of the front sheet 24 is provided with the irregularity shape 20*a*. Therefore, the convex part of the irregularity shape 20*a* is elastically brought into point contact with the skin surface of the wearer, and air can pass through the concave part, whereby breathability is good. Therefore, according to the front sheet 24, good texture can be improved as compared with the case where the front sheet 24 and the skin surface are brought into surface contact with each other. Even after the absorber 20 absorbs body fluids such as urine and sweat, the convex part of the front sheet 24 and the skin surface wetted with urine and the like are brought into point contact with each other, and furthermore, the concave part has breathability, whereby discomfort of the tactile sense of the skin surface can be mitigated.

The front-side second non-woven fabric 24*b* is joined to the outer surface opposite to the surface facing the skin surface side in the front-side first non-woven fabric 24*a*. The front-side second non-woven fabric 24*b* has a shape that is gentler in undulation than the irregularity shape of the front-side first non-woven fabric 24*a*. The surface facing the skin surface side of the front-side second non-woven fabric 24*b* has a flat surface shape, for example. As described above, the undulation of the front-side second non-woven fabric 24*b* is smaller than the undulation of the front-side first non-woven fabric 24*a*. Therefore, the ease of expansion in the plane direction of the front-side second non-woven fabric 24*b* is smaller than that of the front-side first non-woven fabric 24*a*. Due to this, expansion of the front-side first non-woven fabric 24*a* is restrained by the front-side second non-woven fabric 24*b*, and the irregularity shape 20*a* of the front-side first non-woven fabric 24*a* is maintained. At this time, the concave part of the irregularity shape 20*a* of the front-side first non-woven fabric 24*a* is joined to the front surface having a flat surface shape of the front-side second non-woven fabric 24*b*, and the shape of the convex part of the irregularity shape is maintained due to joint of this concave part. For example, even when the wearer presses the irregularity shape 20*a* by contact, the convex part is less likely to be deformed, and the good texture due to point contact with the convex part can be maintained.

Although the front sheet 24 is formed of two non-woven fabrics (the front-side first non-woven fabric 24*a* and the front-side second non-woven fabric 24*b*), the number of non-woven fabrics may be 3 or more.

When the front sheet 24 is provided with the irregularity shape 20*a*, among the plurality of non-woven fabrics, the front surface of at least one non-woven fabric facing the skin surface side is only required to be provided with the irregularity shape 20*a*. Therefore, all the non-woven fabrics constituting the front sheet 24 may also be provided with the irregularity shape 20*a*.

Furthermore, the front sheet 24 may be formed of one non-woven fabric. In this case, the front surface facing the skin surface side of one non-woven fabric is provided with the irregularity shape 20*a*.

Joint of the front-side first non-woven fabric 24*a* and the front-side second non-woven fabric 24*b* can be performed by adhesion using a hot melt adhesive or welding by heat sealing, but ultrasonic welding is preferable. Use of ultrasonic welding for the joint can maintain flexibility of the front sheet 24 as compared with a case of using an adhesive, and gives little crispy stiff tactile sense and little discomfort.

In the above, the surface facing the skin surface side of the front-side first non-woven fabric 24*a* is provided with the plurality of irregularity shapes 20*a*. However, the aspect of the front sheet 24 also includes an aspect in which the surface facing the skin surface side of the front-side first non-woven fabric 24*a* has a flat surface shape. In this case, the front sheet 24 may be formed of only one non-woven fabric having a flat surface shape. That is, the front sheet 24 may be formed only of the front-side first non-woven fabric 24*a* having a flat surface shape with the front-side second non-woven fabric 24*b* being omitted.

As illustrated in FIG. 4 and the like, the core 25 is a rectangular belt-shaped sheet extending in the waist orthogonal direction in plan view. Note that a constriction may be formed in a center position in the waist orthogonal direction at the both edge portions in the waist width direction of the core 25. The constriction is formed by recessing the both edge portions in the waist width direction in order to arrange the core 25 around the leg of the wearer without a gap. The constriction has a curve shape for extending the curve of the above-described leg round curve portion 15*b*.

Figure 5A:
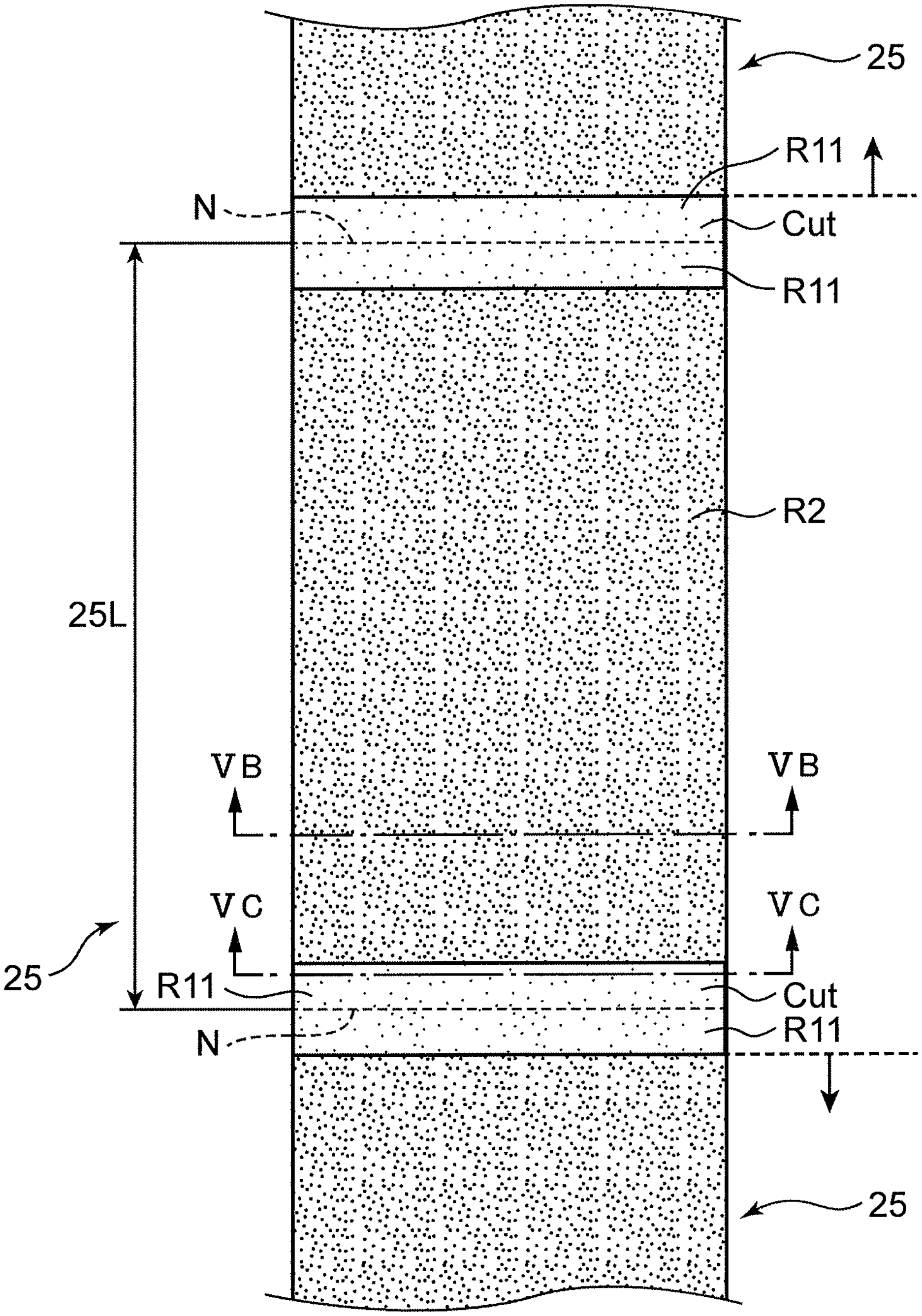
FIG. 5A is a plan view illustrating a distribution state of a SAP in a core continuous in a waist orthogonal direction.

Although described in detail in the production method described later, the core 25 is produced by being continuously coupled in the waist orthogonal direction as illustrated in FIG. 5A. A cut region Cut is provided between the continuous core 25. The continuous core 25 is cut along a cutting line N in the cutting region Cut and divided into one core 25 having a predetermined length 25L. The distribution density of the SAP in the cut region Cut is lower than the distribution density of the SAP in a holding region R2 described later. Specifically, in the present embodiment, the cut region Cut of a core-side first non-woven fabric S1 and a core-side second non-woven fabric S2 hardly holds the SAP. Note that in the cut region Cut, the SAP may not be supported at all.

Figure 5B:
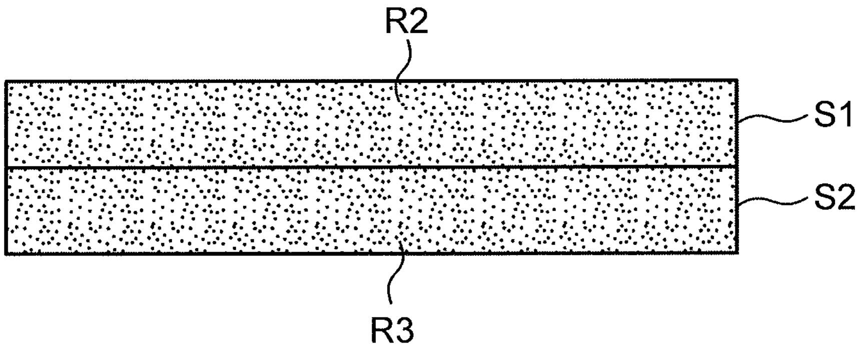
FIG. 5B is a cross-sectional view taken along cutting line VB-VB of FIG. 5A.

The core 25 is formed of the two core-side first non-woven fabric S1 and core-side second non-woven fabric S2, and a super absorbent polymer (SAP) supported on the core-side first non-woven fabric S1 and the core-side second non-woven fabric S2. In the core 25, the two core-side first non-woven fabric S1 and core-side second non-woven fabric S2 are laminated as illustrated in FIG. 5B and the like. The SAP is a water absorbent substance having water absorbency, and for example, sodium polyacrylate is used.

More specifically, the core 25 further includes the core-side second non-woven fabric S2 laminated on the core-side first non-woven fabric S1 so as to oppose the core-side first non-woven fabric S1 with the SAP interposed therebetween. A fiber layer raised to form a gap for supporting the SAP is formed on an opposing surface of each of the core-side first non-woven fabric S1 and the core-side second non-woven fabric S2. By disposing the SAP in the gap in the fiber layer, a large amount of SAP can be supported on the core-side first non-woven fabric S1 and the core-side second non-woven fabric S2. Examples of the non-woven fabric having such a fiber layer include an air-laid non-woven fabric.

By causing the two-layer core-side first non-woven fabric S1 and core-side second non-woven fabric S2 to support the SAP, it is possible to increase the support amount of the SAP and to increase the absorption amount of urine and the like by the SAP as compared with the case of providing a one-layer core-side first non-woven fabric.

Figure 5C:
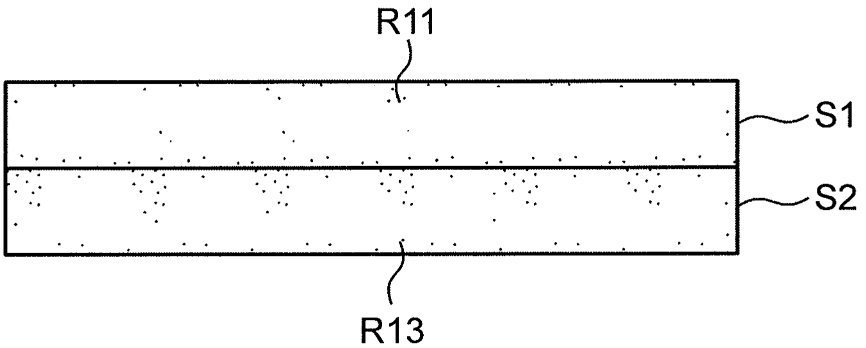
FIG. 5C is a cross-sectional view taken along cutting line VC-VC of FIG. 5A.

Furthermore, as illustrated in FIGS. 5A to 5C, the core-side first non-woven fabric S1 supports the SAP so as to form a first low-density region R11 and the holding region R2. This first low-density region R11 is disposed adjacent in the waist orthogonal direction to both end portions of the waist orthogonal direction of the holding region R2. The first low-density region R11 is a region from the end portion in the waist orthogonal direction of the holding region R2 to the cutting line N in the cut region Cut of FIG. 5A. The distribution density of the SAP in the first low-density region R11 is lower than the distribution density of the SAP in the holding region R2. Note that the first low-density region R11 may not support the SAP. The holding region R2 is a region where the SAP is supported so as to have predetermined water absorption performance such as urine. Then, the core-side first non-woven fabric S1 exerts water absorption performance set in advance as the first low-density region R11 and the holding region R2 as a whole.

On the other hand, as illustrated in FIGS. 5B and 5C, a holding region R3 of the core-side second non-woven fabric S2 is disposed at a position overlapping the holding region R2 of the core-side first non-woven fabric S1 in plan view. A third low-density region R13 of the core-side second non-woven fabric S2 is disposed at a position overlapping the first low-density region R11 of the core-side first non-woven fabric S1 in plan view. The distribution density of the SAP in the third low-density region R13 is lower than the distribution density of the SAP in the holding region R2 and the holding region R3. Note that the third low-density region R13 may not support the SAP. The distribution density of the SAP in the holding region R3 is set so as to have predetermined water absorption performance such as urine. Then, the distribution density of the SAP in the entire third low-density region R13 and holding region R3 of the core-side second non-woven fabric S2 is set so as to exert water absorption performance set in advance.

The density of the SAP in the holding region R3 may be about the same as or different from that in the holding region R2. The density of the SAP in the third low-density region R13 may be about the same as or different from that in the first low-density region R11.

Then, the core-side first non-woven fabric S1 is disposed on the skin surface side of the wearer of the wearing article 1, and the core-side second non-woven fabric S2 is laminated on the back surface side of this core-side first non-woven fabric S1.

These two core-side first non-woven fabric S1 and core-side second non-woven fabric S2 are laminated such that the fiber layers raised and supporting the SAP oppose each other. This makes it possible to suppress falling of the SAP. That is, the high-density fibers are entangled at an outside part that is not raised of the outer surface side of the core-side first non-woven fabric S1 and the core-side second non-woven fabric S2. This outside part supports the SAP in the core-side first non-woven fabric S1 and the core-side second non-woven fabric S2.

The core-side first non-woven fabric S1 is formed to hold the SAP. Since the absorption performance per unit volume of the SAP is higher than the absorption performance per unit volume of fluff pulp, the amount of fluff pulp used when fluff pulp is used can be reduced. Therefore, the thickness of the core 25 can be made thinner than that of a non-woven fabric formed of only fluff pulp having an amount necessary for a predetermined absorption performance. Since the thickness of the wearing article 1 including this core-side first non-woven fabric S1 is also thin, the wearing article 1 can be easily fitted to the body shape of the waist of the wearer, and the fitting feeling of the wearing article 1 can be improved.

Furthermore, the thickness of the core 25 can be made thinner than that of a non-woven fabric formed of only fluff pulp having an amount necessary for a predetermined absorption performance. Since by thinning of the core-side first non-woven fabric S1 and the core-side second non-woven fabric S2, the thickness of the wearing article 1 can also be reduced, the wearing article 1 can be easily fitted to the body shape of the waist of the wearer, and the fitting feeling of the wearing article 1 can be improved.

Since the distribution density of the SAP is higher in the holding region R2 than in the first low-density region R11, flexibility is poor. On the other hand, the distribution density of the SAP is lower in the first low-density region R11 than in the holding region R2, and thus the first low-density region R11 has a higher flexibility than the holding region R2. Therefore, the shape of the core 25 having the first low-density region R11 is easily deformed. Here, when the wearer wears the wearing article 1, the both end portions in the waist orthogonal direction of the holding region R2 are disposed to face the front abdomen portion and the back portion of the wearer, respectively. The first low-density region R11 where the distribution density of the SAP is lower than that in the holding region R2 is disposed in a part adjacent in the waist orthogonal direction to the both end portions in the waist orthogonal direction of this holding region R2. Therefore, the part of the core where the first low-density region R11 is disposed is flexibly deformed so as to fit the body shape of the front abdomen portion and the back portion, and the part abuts on the front abdomen portion and the back portion with a soft tactile sense, whereby the wearing feeling of the wearing article 1 can be improved.

Furthermore, the core 25 illustrated in FIGS. 5A to 5C and the front sheet 24 having the irregularity shape 20*a* may be combined to produce the wearing article 1. In this case, breathability and texture can be improved by the irregularity shape 20*a* of the front sheet 24. Even after absorption of the body fluid, the good breathability and texture can be maintained by the irregularity shape 20*a* of the front sheet 24.

The arrangement of the low-density region in the core 25 is not limited to the above-described form, and the arrangement as illustrated in FIGS. 6A to 6D, for example, may be adopted.

Figure 6A:
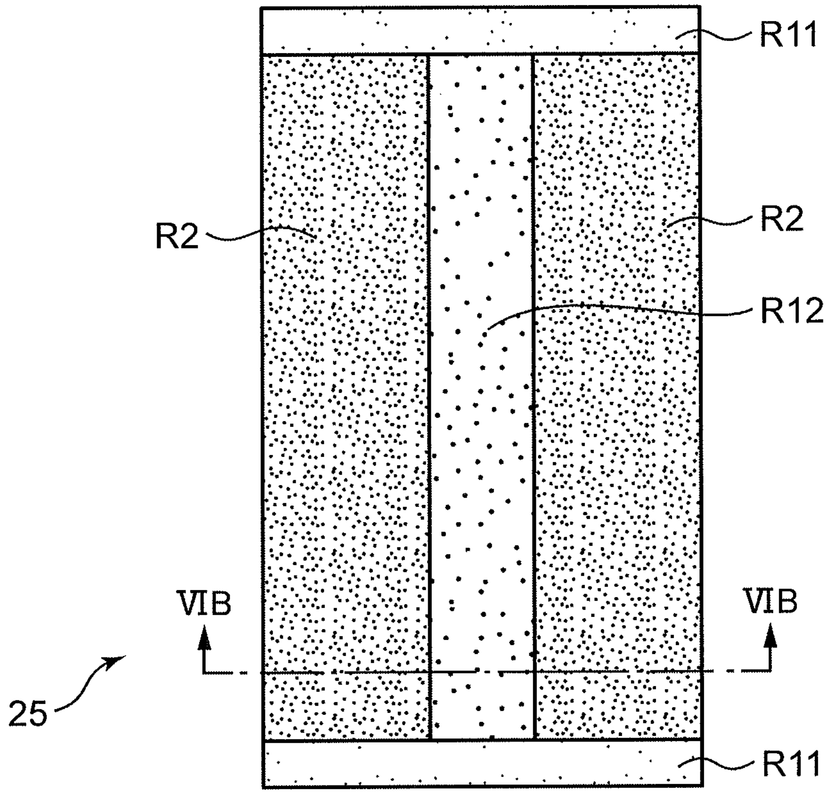
FIG. 6A is a plan view illustrating another distribution state of the SAP in the core.
Figure 6B:
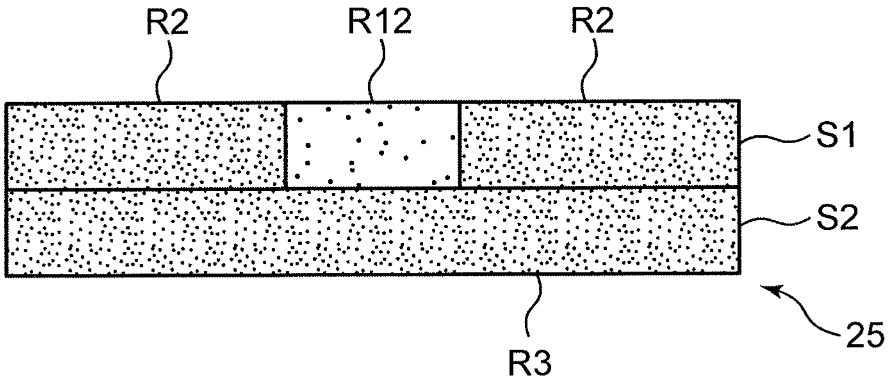
FIG. 6B is a cross-sectional view taken along cutting line VIB-VIB of FIG. 6A.

In the core-side first non-woven fabric S1 illustrated in FIGS. 6A and 6B, the first low-density region R11 is disposed adjacent in the waist orthogonal direction to the both end portions in the waist orthogonal direction of the holding region R2, and a second low-density region R12 is disposed to be sandwiched in the waist width direction by the holding region R2. The holding region R2 is a region where the SAP is supported so as to have predetermined water absorption performance such as urine. The distribution density of the SAP in the second low-density region R12 is lower than the distribution density of the SAP in the holding region R2. Note that the second low-density region R12 may not support the SAP. The distribution density of the SAP in the second low-density region R12 may be about the same as or different from the distribution density of the SAP in the first low-density region R11. Then, the core-side first non-woven fabric S1 exerts water absorption performance set in advance as the first low-density region R11, the second low-density region R12, and the holding region R2 as a whole.

The formation position of the second low-density region R12 of the present embodiment will be further described. As illustrated in FIG. 6A, the second low-density region R12 is provided continuously along the waist orthogonal direction in the center portion in the waist width direction of the core 25. The holding region R2 is provided so as to be adjacent to the both sides in the waist width direction of the second low-density region R12.

The amount of the SAP held in the second low-density region R12 is smaller than the amount of the SAP held in the holding region R2. Therefore, the flexibility of the core 25 in the second low-density region R12 is higher than the flexibility of the core 25 in the holding region R2. Hence, the core 25 can be easily deformed along with the body shape, and the stiff feeling of the core 25 can be suppressed, whereby the fitting feeling of the wearing article 1 can be improved.

For example, in FIGS. 6A to 6D, the second low-density region R12 continuously extends in the waist orthogonal direction in the center portion in the waist width direction of the core 25. Due to this, by bending the core 25 based on the second low-density region R12 where the amount of the SAP is smaller than that of the holding region R2 and flexibility is high, the core 25 can be deformed along with the body shape of the waist of the wearer over the formation range of the second low-density region R12 in the waist orthogonal direction, and the fitting feeling of the wearing article can be improved.

Figure 6C:
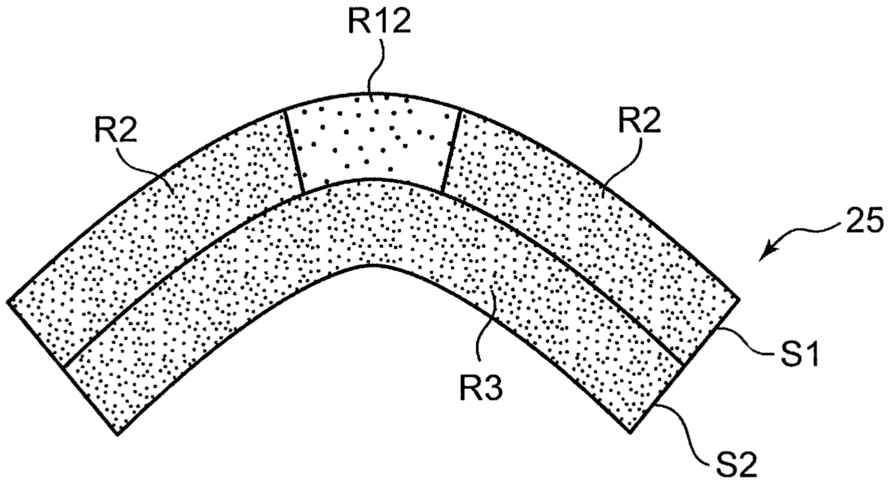
FIG. 6C is a cross-sectional view taken along cutting line VIB-VIB of FIG. 6A, and illustrating a state where the core is bent in an inverted V shape.
Figure 6D:
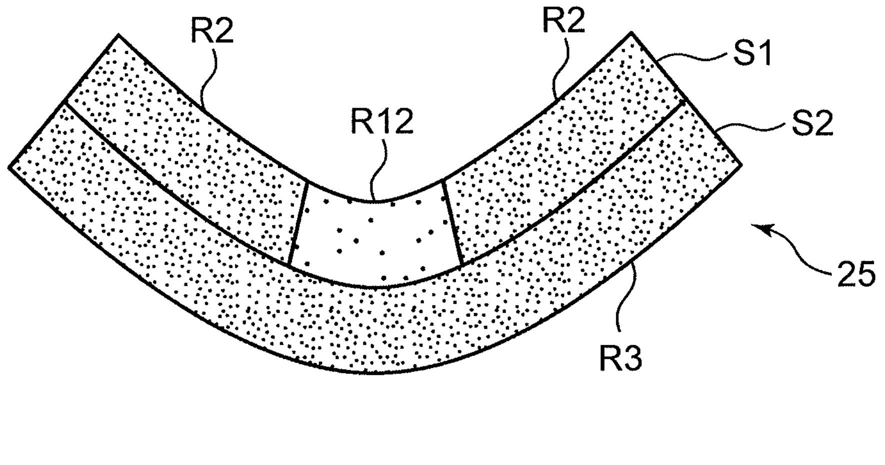
FIG. 6D is a cross-sectional view taken along cutting line VIB-VIB of FIG. 6A, and illustrating a state where the core is bent in a V shape.

Specifically, since the second low-density region R12 is disposed in the center portion in the waist width direction, as illustrated in FIG. 6C, the core 25 is easily deformed into a shape bent in an inverted V shape substantially symmetrically about the second low-density region R12 in the center portion. Therefore, when the wearer wears the wearing article, the core 25 extending from the back portion to the front abdomen portion via the crotch portion deforms as illustrated in FIG. 6C in accordance with the shape of the crotch portion of the wearer. Therefore, the wearing feeling of the wearing article 1 can be further improved. As illustrated in FIG. 6D, the core 25 can be deformed into a shape in which the core 25 is bent in a V shape substantially symmetrically about the second low-density region R12. Also in this case, the core 25 is less likely to be bulky in the crotch portion, and the wearing feeling of the wearing article 1 can be improved.

Since the absorption amount of urine and the like in the second low-density region R12 is smaller than that in the holding region R2, the urine and the like can be diffused in the waist orthogonal direction along the second low-density region R12. Therefore, the core 25 can effectively absorb urine and the like using the holding regions R2 adjacent to both sides in the waist width direction of the second low-density region R12.

More specifically, in the arrangement of the second low-density region R12 and the holding region R2 illustrated in FIG. 6A, the second low-density region R12 is positioned in the center portion in the waist width direction of the core 25, that is, provided at a position in the crotch portion where the amount of urine and the like received is relatively large. Therefore, there is a high possibility that urine and the like are guided to the second low-density region R12 and the holding region R2 adjacent in the waist width direction to the second low-density region R12. When urine and the like are guided to the second low-density region R12 and the holding region R2, the urine and the like can be diffused along the second low-density region R12 extending along the waist orthogonal direction while being absorbed in the second low-density region R12 and the holding region R2 around the second low-density region R12. At this time, the urine and the like diffused along the second low-density region R12 are also absorbed in the second low-density region R12 and the holding region R2 adjacent in the waist width direction to the second low-density region R12. Due to this, as compared with the case where the second low-density region R12 does not exist (the case where the density of the SAP is constant over the entire holding range), urine and the like can be quickly absorbed using a wider range of the holding region R2 by diffusing the urine and the like. Therefore, it is possible to more quickly eliminate the sticky feeling on the skin surface due to urine and the like and to mitigate the discomfort.

Furthermore, since the second low-density region R12 can be used as a region for expansion of the SAP in the holding region R2, excessively close contact of the absorber 20 to the skin surface can be suppressed. Hence, it is possible to more quickly eliminate the sticky feeling on the skin surface due to urine and the like and to mitigate the discomfort.

The wearing article 1 having the core 25 in FIGS. 6A to 6D described above is worn around the waist by engaging the male fasteners 12 and the female fastener 22. Then, in a state where the absorber 20 is in close contact with the crotch portion, before absorption of a body fluid, a feeling of close contact with the crotch portion can be improved by the flexibility of the second low-density region R12 of the core 25. Furthermore, even after absorption of the body fluid, since the expansion space of the SAP can be secured by the second low-density region R12 of the core 25, the core 25 can be suppressed from expanding more than necessary on the skin surface side, and the good texture can be maintained.

Furthermore, the core 25 illustrated in FIGS. 6A to 6D and the front sheet 24 having the irregularity shape 20*a* may be combined to produce the wearing article 1. In this case, in the state where the absorber 20 is in close contact with the crotch portion, before absorption of the body fluid, the breathability and the texture of the wearing article 1 can be improved while improving the feeling of close contact with the crotch portion by the irregularity shape 20*a* of the front sheet 24 and the second low-density region R12 of the core 25. Furthermore, even after absorption of the body fluid, since the expansion space of the SAP can be secured by the second low-density region R12 of the core 25, the core 25 can be suppressed from expanding more than necessary on the skin surface side, and the good breathability and texture can be maintained by the irregularity shape 20*a* of the front sheet 24.

Note that the second low-density region R12 and the holding region R2 are not limited to being formed by adjusting the support amount of the SAP in the core-side non-woven fabric. For example, a space formed by dividing the core-side non-woven fabric on which the holding region R2 is formed and separating the divided part in the width direction can also be used as the second low-density region R12. Alternatively, a part where a gap for holding the SAP is made small by pressing the surface (surface subjected to raising treatment) of the core-side non-woven fabric of the holding region R2 to crush the fiber in the raised state can be used as the second low-density region R12.

In the above, the core-side second non-woven fabric S2 has only the third low-density region R13 as a low-density region. However, both of the two core-side non-woven fabrics S1 and S2 may have the first low-density region R11, the second low-density region R12, and the holding region R2. For example, the core-side first non-woven fabric S1 includes the first low-density regions R11 provided in both ends of the core-side first non-woven fabric S1 and the second low-density region R12 between both the first low-density regions R11. Similarly, the core-side second non-woven fabric S2 includes the third low-density regions R13 provided in both ends of the core-side second non-woven fabric S2 and the second low-density region R12 between the third low-density regions R13. In this case, the second low-density region R12 of the first core-side non-woven fabric S1 and the second low-density region R12 of the core-side second non-woven fabric S2 may be disposed at different positions in plan view, or may be disposed at an overlapping position in plan view.

Figure 7A:
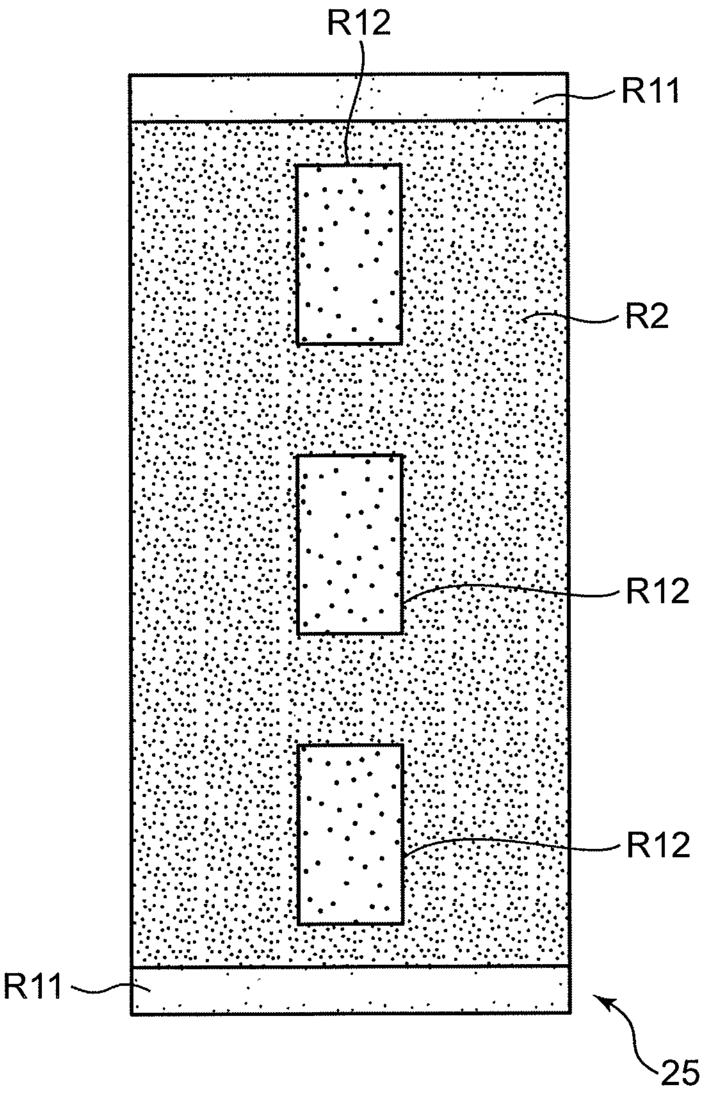
FIG. 7A is a plan view illustrating another distribution state of the SAP in the core.
Figure 7B:
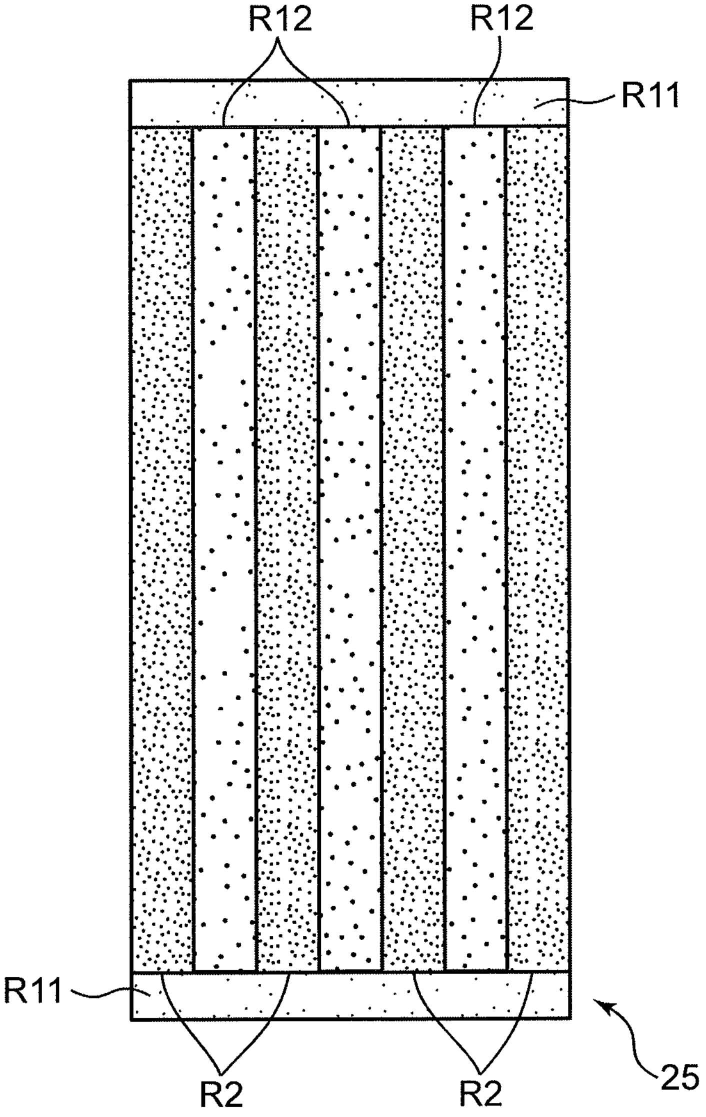
FIG. 7B is a plan view illustrating another distribution state of the SAP in the core.
Figure 7C:
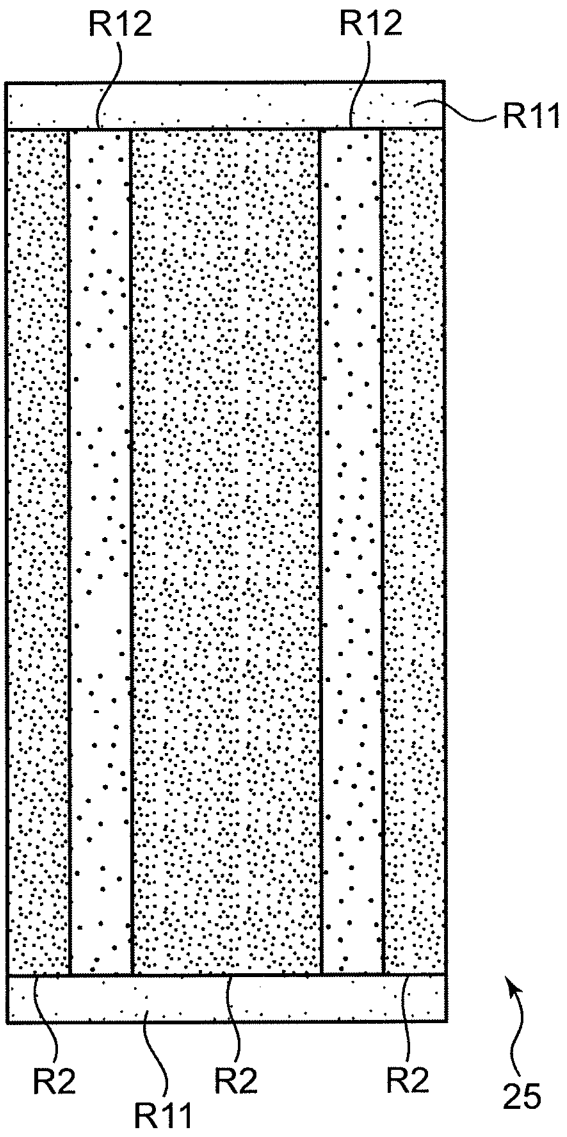
FIG. 7C is a plan view illustrating another distribution state of the SAP in the core.

The second low-density region R12 in FIGS. 6A to 6D may have the form illustrated in FIGS. 7A to 7C, for example. Regarding the second low-density region R12 in FIGS. 7A to 7C, only differences from FIGS. 6A to 6D will be mainly described.

In the example illustrated in FIG. 7A, the first low-density regions R11 are disposed adjacent in the waist orthogonal direction to both end portions in the waist orthogonal direction of the holding region R2, and the center portion in the waist width direction of the core-side first non-woven fabric S1 is provided with a plurality of the second low-density regions R12 intermittently along the waist orthogonal direction. Due to this, the diffusion range of urine and the like in the core 25 and the absorption range by the holding region R2 can be roughly divided into three using the holding region R2 between the plurality of second low-density regions R12 as a weir.

At the center portion in the waist width direction of the core-side first non-woven fabric S1, in both end portions in the waist orthogonal direction, the holding regions R2 are provided adjacent in the waist orthogonal direction to the second low-density region R12. That is, in the core-side first non-woven fabric S1, the both end portions in the waist orthogonal direction of the second low-density region R12 are closed by the holding regions R2. This allows the holding region R2 to be used as a weir for the second low-density region R12. Therefore, according to the configuration illustrated in FIG. 7A, urine and the like can be prevented from being guided to the outside of the core 25 in the waist orthogonal direction by the second low-density region R12.

In the example illustrated in FIG. 7B, in the core-side first non-woven fabric S1, the first low-density regions R11 are disposed adjacent in the waist orthogonal direction to both end portions in the waist orthogonal direction of the holding region R2, and in addition to the second low-density regions R12 similar to that in FIG. 6A provided in the center position in the waist width direction, the second low-density region R12 is provided on each of the both sides in the waist width direction of this second low-density region R12. The three second low-density regions R12 extend in parallel to one another in the waist orthogonal direction. The added two second low-density regions R12 make it easy to diffuse, throughout the entire core 25, urine and the like spreading on the front surface of the core 25, and further improve the flexibility in the waist orthogonal direction of the core 25.

In the example illustrated in FIG. 7C, the first low-density regions R11 are disposed adjacent in the waist orthogonal direction to the both end portions in the waist orthogonal direction of the holding region R2, and the second low-density region R12 illustrated in FIG. 7B provided in the center position in the waist width direction of the core-side first non-woven fabric S1 is not provided. That is, the holding region R2 is provided in the center position in the waist width direction of the core-side first non-woven fabric S1, and the second low-density region R12 is provided on each of the both sides in the waist width direction of the center position. The two second low-density regions R12 extend in parallel to each other in the waist orthogonal direction. The two second low-density regions R12 make it easier to diffuse urine and the like throughout the entire core 25 than the one second low-density region R12 illustrated in FIG. 6A, and further improve the flexibility in the waist width direction of the core 25.

Also in the examples illustrated in FIGS. 7A and 7B, similarly to the example illustrated in FIG. 6A, the core 25 is easily deformed into a shape bent in a V shape or an inverted V shape substantially symmetrically about the center portion in the waist width direction where the second low-density region R12 is disposed as the center. Also in the example illustrated in FIG. 7C, since the two second low-density regions R12 separated from the center portion in the waist width direction are provided, the core 25 is easily deformed into a shape bent in a U shape or an inverted U shape substantially symmetrically.

Furthermore, the extending direction of the second low-density region R12 is not limited to the waist orthogonal direction. For example, the second low-density region R12 may be along the waist width direction in the core 25 and may be sandwiched in the waist width direction by the holding regions R2. For example, when the second low-density region R12 is disposed in the crotch along the waist width direction, urine and the like can be diffused in the waist width direction along the second low-density region R12 and absorbed in the holding region R2 adjacent to the second low-density region R12. Since the holding region R2 is adjacent to the end portion in the waist width direction of the second low-density region R12, the holding region R2 can be used as a weir. Therefore, urine and the like can be prevented from being guided to the outside in the waist width direction of the core 25 by the second low-density region R12.

The second low-density region R12 may have a part extending along the waist orthogonal direction and a part extending along the waist width direction. For example, the second low-density region R12 may have a part extending along the waist orthogonal direction in the center portion in the waist width direction of the core 25 and a part branching in the waist width direction from the part extending in the waist orthogonal direction. This makes it possible to diffuse urine and the like in both the waist orthogonal direction and the waist width direction along the second low-density region R12, and to cause the holding region R2 to quickly absorb the urine and the like.

Furthermore, the regions having different distribution densities of the SAP are not limited to the low-density regions R11, R12, and R13 and the holding regions R2 and R3. For example, based on the holding region R2, a plurality of regions having different distribution densities selected from distribution regions of the distribution density of the SAP ranges from 0 to the distribution density of the SAP in the holding region R2 may be provided in the core 25.

Although both of the two core-side non-woven fabrics support the SAP in the above description, only any one of the core-side non-woven fabrics may support the SAP, and the remaining core-side non-woven fabric may not support the SAP. Furthermore, fluff pulp may be contained.

For example, in the core 25 of FIGS. 5A to 5C, the core 25 may be configured such that the core-side non-woven fabric containing fluff pulp is disposed on the skin surface side of the wearer, and the core-side first non-woven fabric S1 illustrated in FIGS. 5A to 5C is disposed on the side opposite to the skin surface side. In this case, the body fluid is absorbed earlier than the SAP by the fluff pulp of the core-side non-woven fabric on the skin surface side, and the body fluid absorbed by the fluff pulp is further absorbed by the SAP of the core-side first non-woven fabric S1 on the opposite side. Also in the core 25 of FIGS. 6A to 6D and FIGS. 7A to 7C, similarly to the above description, the core-side non-woven fabric containing fluff pulp may be disposed on the upper layer, and the core-side first non-woven fabric S1 illustrated in FIGS. 6A to 6D and FIGS. 7A to 7C may be disposed on the lower layer.

The method for supporting the SAP in the core-side non-woven fabric is not limited to the method for supporting the SAP on the fiber layer of the core-side non-woven fabric raised for forming a gap for supporting the SAP. For example, an adhesive may be applied to the front surface of the core-side non-woven fabric, and the SAP may be scattered to the applied adhesive to dispose the SAP on the front surface of the core-side non-woven fabric. In this case, the amount per unit area of the adhesive applied for the low-density regions R11, R12, and R13 is less than the amount per unit area of the adhesive applied for the holding regions R2 and R3. Other than that, the SAP may be supported in the fiber layer of the core-side non-woven fabric by scattering the SAP on the fiber layer of the raised core-side non-woven fabric and sucking the SAP from the surface opposite to the surface on which the SAP is scattered.

The number of the core-side non-woven fabrics forming the core 25 is not limited to 2, and may be formed of one core-side non-woven fabric.

As illustrated in FIG. 4 and the like, the back sheet 26 is a rectangular belt-shaped sheet extending in the waist orthogonal direction. Furthermore, the back sheet 26 is provided on the outer surface opposite to the surface facing the skin surface side of the core 25, and sandwiches the core 25 with the front sheet 24. The back sheet 26 includes a liquid impermeable sheet 26*a* facing the core 25 and an outer layer sheet 26*b* covering the outer surface opposite to the surface of the liquid impermeable sheet 26*a* facing the core 25.

The liquid impermeable sheet 26*a* is a belt-shaped sheet that has water repellency and does not allow urine and the like to permeate. The liquid impermeable sheet 26*a* is formed of a non-woven fabric made of, for example, polypropylene, polyethylene, or the like. The liquid impermeable sheet 26*a* preferably has breathability.

The core 25 is joined to the liquid impermeable sheet 26*a* in a state where the core 25 is disposed so as to fall within the range in the waist width direction and the waist orthogonal direction of the liquid impermeable sheet 26*a*. Since the liquid impermeable sheet 26*a* is provided on the outer surface opposite to the surface facing the skin surface side of the core 25 as described above, it is possible to suppress urine and the like from flowing out to the outside of the liquid impermeable sheet 26*a* even when urine and the like cannot be completely absorbed in the core 25.

The liquid impermeable sheet 26*a* has a rectangular shape in the example illustrated in FIG. 4. However, in the liquid impermeable sheet 26*a*, a leg round curve portion may be formed in a center position in the waist orthogonal direction at both edge portions in the waist width direction of the liquid impermeable sheet 26*a* in plan view. The leg round curve portion is formed by recessing the both edge portions in the waist width direction in order to arrange the liquid impermeable sheet 26*a* without a gap around the leg of the wearer.

The leg gather 31 is an elastic member corresponding to the groin when the wearer wears the wearing article 1. The leg gather 31 is provided along each of the both edges in the waist width direction of the liquid impermeable sheet 26*a* on substantially the entire liquid impermeable sheet 26*a* in the waist orthogonal direction. The leg gather 31 is disposed in an expanded state in the waist orthogonal direction between the liquid impermeable sheet 26*a* and the front sheet 24, and is joined to at least one of the liquid impermeable sheet 26*a* and the front sheet 24. The joint can be performed by adhesion using a hot melt adhesive or welding by heat sealing, but ultrasonic welding is preferable. By providing such the leg gather 31, a soft feeling can be given to the groin as compared with a case where the both edge portions of the absorber 20 directly abut on the groin, and the wearing feeling of the wearing article 1 is further improved.

The leg gather 31 may be disposed between the liquid impermeable sheet 26*a* and the outer layer sheet 26*b* and joined to at least one of these.

The absorber elastic member 21 is provided at a free end (end portion on the side opposite to the waist member 10) in the waist orthogonal direction of the liquid impermeable sheet 26*a*, and has elasticity capable of expanding and contracting in the waist width direction. Therefore, the tip end portion of the absorber 20 having the liquid impermeable sheet 26*a* on the side opposite to the side joined to the waist member 10 is capable of expanding and contracting in the waist width direction. As described above, the waist member 10 is also capable of expanding and contracting in the waist width direction by the waist elastic member 11. Due to this, both the waist member 10 and the tip end portion of the absorber 20 become capable of expanding and contracting in the waist width direction in accordance with the length of the waist of the wearer, and therefore the degree of freedom in selection of the engagement position between the male fasteners 12 of the waist member 10 and the female fastener 22 of the absorber 20 is large. Therefore, the fitting feeling of the wearing article 1 can be improved.

Note that the absorber elastic member 21 is not an essential component. Even when the absorber elastic member 21 is omitted, since the waist member 10 has elasticity in the waist width direction, the fitting feeling of the wearing article 1 can be improved.

The outer layer sheet 26*b* is a sheet extending in the waist orthogonal direction and formed of a non-woven fabric, and is attached to the outer surface opposite to the surface facing the skin surface side of the liquid impermeable sheet 26*a* in a state of covering the liquid impermeable sheet 26*a* from the outer surface side. Therefore, the appearance from the outside of the wearing article 1 and the texture of the wearing article 1 can be improved. The outer layer sheet 26*b* has a rectangular shape in the example illustrated in FIG. 4 and the like. However, in the outer layer sheet 26*b*, a leg round curve portion may be formed in the center position in the waist orthogonal direction at both edge portions in the waist width direction of the outer layer sheet 26*b* in plan view. In this case, the leg round curve portion is formed by recessing the both edge portions in the waist width direction in order to arrange the outer layer sheet 26*b* without a gap around the leg of the wearer.

As described above, the liquid impermeable sheet 26*a* and the outer layer sheet 26*b* can be provided with the leg round curve portion. Furthermore, as described above, the lower edge on the groin of the waist member 10 is provided with the leg round curve portion 15*b*. In this case, as illustrated in FIGS. 1 and 2, by assembling the wearing article 1 by engaging the male fasteners 12 of the waist member 10 and the female fastener 22 of the absorber 20, a curved leg hole disposed along the entire circumference of the groin can be formed by the leg round curve portion of the liquid impermeable sheet 26*a* and the outer layer sheet 26*b* and the leg round curve portion 15*b* of the waist member 10.

The peripheral edge portion of the leg hole elastically is brought into close contact with the groin over the entire circumference by the leg gather 31 and the waist elastic member 11 disposed in the vicinity of the leg round curve portion 15*b*. This can improve the wearing feeling.

The female fastener 22 is provided on the outer surface of the tip end portion on the side opposite to the waist member 10 of the outer layer sheet 26*b* in the waist orthogonal direction. The female fastener 22 is provided over substantially the entirety in the waist width direction at the tip end portion of the outer layer sheet 26*b*. The length in the waist orthogonal direction of the female fastener 22 may be about the same as the length in the waist orthogonal direction of the male fastener 12, for example, or may be longer than the length in the waist orthogonal direction of the male fastener 12.

In this manner, the female fastener 22 is provided over substantially the entire tip end portion of the outer layer sheet 26*b* in the waist width direction. Therefore, by expanding and contracting the waist member 10 in the waist width direction, the male fastener 12 can be engaged with an arbitrary position in the waist width direction of the female fastener 22, and the degree of freedom in selection of the engagement position is large. Therefore, the engagement position between the waist member 10 and the absorber 20 can be easily adjusted in accordance with the length of the waist of each wearer, and the fitting feeling can be improved.

The indicator 50 is discolored in accordance with the amount of urine and the like absorbed by the core 25, and indicates that the wearer has voided urine. The indicator 50 extends in the waist orthogonal direction in the center portion in the waist width direction of the outer layer sheet 26*b* on the surface facing the skin surface side of the outer layer sheet 26*b*. As the indicator 50, for example, an adhesive that discolors in accordance with the absorption amount of urine and the like is used.

As illustrated in FIG. 4, the three-dimensional gather 40 is provided on the surface of the front sheet 24 facing the skin surface side. The three-dimensional gather 40 includes a pair of rising flaps 42 and the three-dimensional gather elastic member 41 provided on each of the rising flaps 42. The rising flaps 42 each extend in the waist orthogonal direction and joined to both edge portions in the waist width direction of the front sheet 24. Specifically, one edge portion (edge portion on the right side, for example) in the waist width direction of each of the rising flaps 42 is joined to one edge portion (edge portion on the right side, for example) of the front sheet 24. Each of the three-dimensional gather elastic members 41 is joined in an expanded state to the other edge portion (edge portion on the left side, for example) in the waist width direction of the rising flap 42. In a state where the absorber 20 is curved in the waist orthogonal direction along the crotch portion of the wearer, the other edge portion (edge portion on the left side, for example) in the waist width direction of each of the rising flaps 42 is contracted by a biasing force of the three-dimensional gather elastic member 41, whereby each of the rising flaps 42 rises with respect to the front sheet 24. When worn, the rising flap 42 is elastically brought into close contact with the back portion, the crotch portion, the front abdomen portion, and the like. Therefore, it is possible to suppress urine and the like from flowing out of the wearing article 1.

The length in the waist width direction and the waist orthogonal direction of the female fastener 22 is only required to be set so as to obtain an engagement force capable of engaging with the male fastener 12 so that the waist member 10 and the absorber 20 are not developed when worn. For example, the female fastener 22 may be provided only in the center portion of the waist width direction at the tip end portion of the outer layer sheet 26*b*, or may be divided into two and provided at the both side portions in the waist width direction.

It is sufficient that the waist member 10 and the absorber 20 can be engaged, and the waist member 10 can be provided with the female fastener 22 and the absorber 20 can be provided with the male fastener 12.

The back sheet 26 may be formed only of the liquid impermeable sheet 26*a*.

A transfer sheet (not illustrated) may be interposed between the front sheet 24 and the core 25. This transfer sheet rapidly diffuses urine and the like along the front surface of the core 25 and prevents the urine and the like absorbed by the core 25 from leaking out from the front sheet 24.

In such the refastenable type wearing article 1, the male fastener 12 and the female fastener 22 are engaged with each other in a state where the absorber 20 is folded in two in the waist orthogonal direction, and the both side portions 10*a* positioned on both sides with respect to the joint portion 10*b* in the waist member 10 are folded in the waist width direction. Due to this, since the female fastener 22 is engaged with the male fastener 12 in the initial state, the refastenable type wearing article 1 described above is in the underpants-shaped form, and the wearer can wear the wearing article as underpants.

By releasing the engagement between the male fastener 12 and the female fastener 22, it is possible to develop into a predetermined development form. In the development form, the both side portions 10*a* of the waist member 10 protrude with respect to the absorber 20 disposed at the joint portion 10*b* of the waist member 10. The both side portions 10*a* can be directed to the tip end portion of the absorber 20 along the waist of the wearer, and can be caused to abut on the back sheet 26 of the absorber 20 disposed along the crotch portion of the wearer. Then, the male fasteners 12 in the both end portions 10*c* in the waist width direction of the waist member 10 are engaged with the female fastener 22 of the back sheet 26 to support the refastenable type wearing article 1 around the waist, whereby the absorber 20 is pulled up and the absorber 20 is brought into close contact with the crotch portion of the wearer.

It is possible to achieve compactness by folding, and to achieve a form suitable for packing, storing, and the like of a plurality of the wearing articles 1.

<Method for Producing Refastenable Type Wearing Article>

A method for producing the refastenable type wearing article 1 will be described below.

In each following step, an MD (machine direction) direction A is a conveyance direction of a sheet or the like, and a CD (cross direction) direction W is a direction substantially orthogonal to a length direction A.

(1) Step 1 to Step 2

Figure 8:
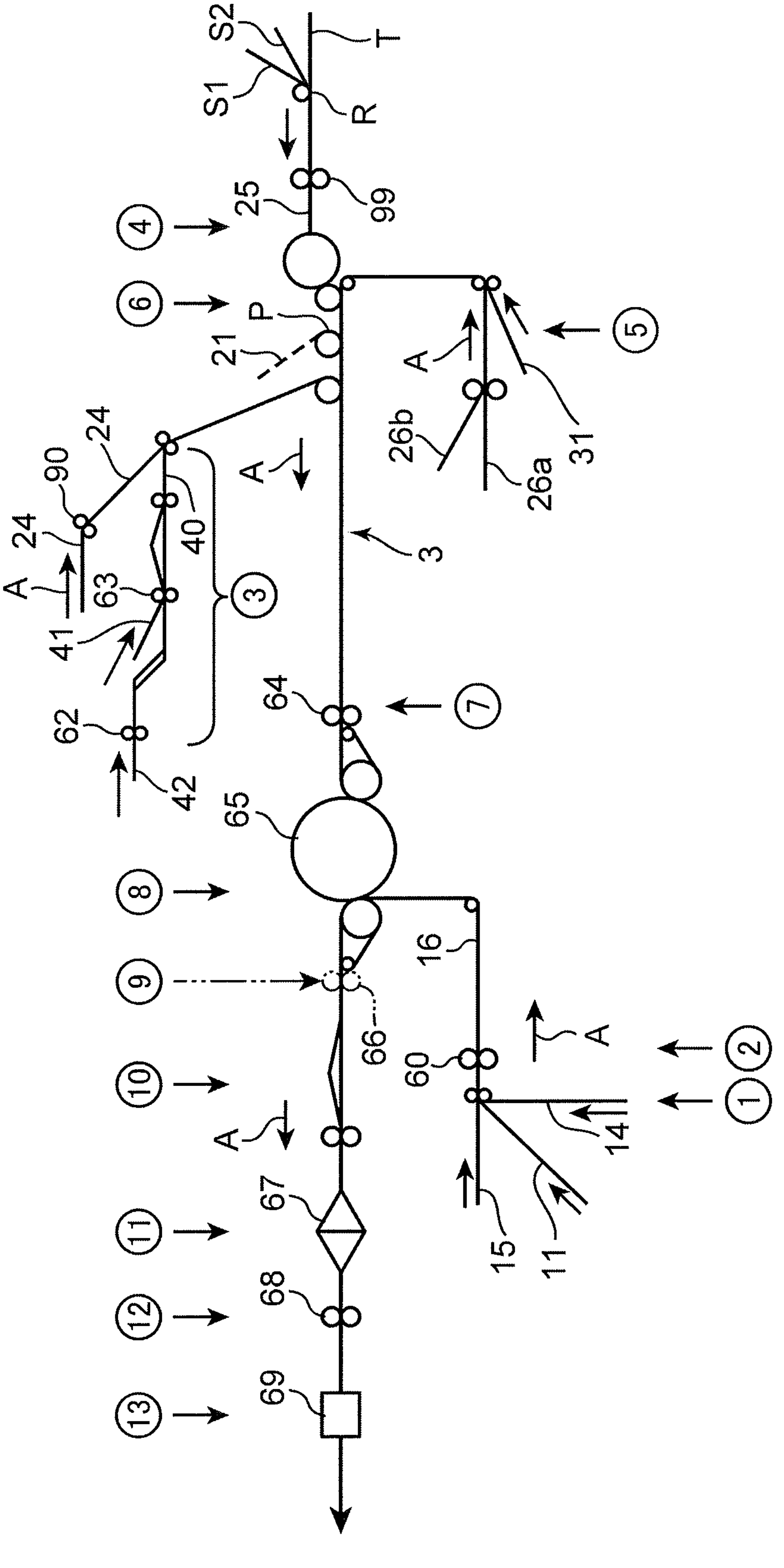
FIG. 8 is a system diagram of a production step of the refastenable type wearing article.
Figure 9:
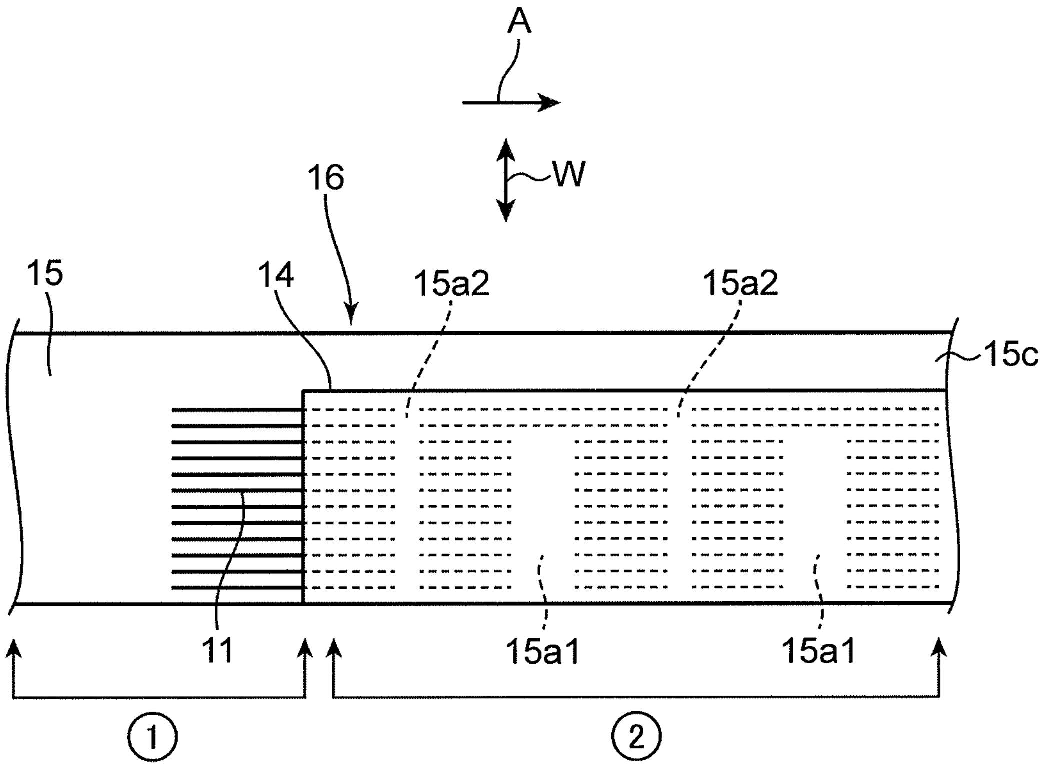
FIG. 9 is a plan view of a production situation of step 1 and step 2.
Figure 17A:
FIG. 17A is a cross-sectional view of a main part in a production process of step 1, and illustrates a state where an outer sheet is conveyed.

As illustrated in FIGS. 8, 9, and 17, step 1 to step 2 are an example of a step of producing, in a horizontal flow state as illustrated in FIG. 9, a waist continuous body in which a plurality of the waist bodies 16 are continuous. In the horizontal flow state of FIG. 9, the MD direction A coincides with the waist width direction, and the CD direction W coincides with the waist orthogonal direction.

(Step 1)

Figure 17B:
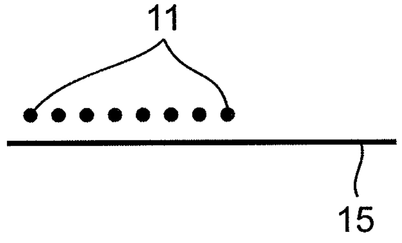
FIG. 17B is a cross-sectional view of a main part in the production process of step 1, and illustrates a state where a waist elastic member is disposed on the outer sheet.

In step 1, a continuous body of the outer sheet 15 where a plurality of the outer sheets 15 are continuous is conveyed in the MD direction A (see FIG. 17A), and the waist elastic members 11 are linearly disposed along the MD direction A on the continuous body of the outer sheet 15 (see FIG. 17B). The waist elastic members 11 are disposed at intervals with each other in the waist orthogonal direction on the lower side spaced apart from the upper end edge of the outer sheet 15.

Figure 17C:
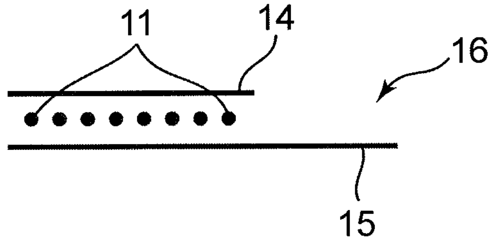
FIG. 17C is a cross-sectional view of a main part in a production process of step 2, and illustrates a state where an inner sheet is conveyed so as to cover the outer sheet and an upper portion of the waist elastic member.

Next, as illustrated in FIGS. 9 and 17C, a continuous body of the inner sheet 14 where a plurality of the inner sheets 14 are continuous is conveyed in the MD direction A, and the continuous body of the inner sheet 14 is disposed on the continuous body of the outer sheet 15 so as to cover the waist elastic member 11 from above. As illustrated in FIG. 9, the continuous body of the inner sheet 14 is positioned in a state where the upper side of the outer sheet 15 is exposed, and is joined while covering the continuous body of the outer sheet 15. Due to this, the extending portion 15*c* is formed by the part where the outer sheet 15 is exposed.

In the above, the waist elastic member 11 is disposed linearly along the MD direction A on the continuous body of the outer sheet 15. However, among the waist elastic members 11, the waist elastic member 11 disposed at the lower end edge of the inner sheet 14 may be disposed in a curve shape along the curve of the leg round curve portion 15*b* formed in step 8 described later. For example, the waist elastic member 11 disposed at the lower end edge of the inner sheet 14 may be disposed on the outer sheet 15 along a substantially sinusoidal path meandering with respect to the MD direction A.

Then, the waist elastic member 11 is tucked between the continuous body of the outer sheet and the continuous body of the inner sheet 14 in the expanded state, and is joined to at least one of the continuous body of the outer sheet 15 and the continuous body of the inner sheet 14. Note that a joint means can be adhesion using a hot melt adhesive or welding by heat sealing, but ultrasonic welding is preferable.

(Step 2)

In step 2, in the continuous body of the outer sheet 15 and the continuous body of the inner sheet 14, the weakening treatment is applied to the waist elastic member 11 in the weakened portion 15*a*1 where the absorber 20 is to be disposed and the weakened portion 15*a*2 where the male fastener 12 is to be disposed. The weakening treatment is a treatment for making the elasticity in a predetermined site weaker than that of a part adjacent to the predetermined site or disabling, by cutting the elastic member at the predetermined site using a blade or fusing the elastic member by applying heat as described later. Specifically, by the above-described weakening treatment, the elastic force of the weakened portions 15*a*1 and 15*a*2 becomes weaker than the elastic force of the part adjacent in the waist width direction (MD direction A in FIG. 9) to the weakened portions 15*a*1 and 15*a*2.

As the weakening treatment, for example, a method of melting the waist elastic member 11 using an emboss roll (heat emboss) (see JP 2002-113042 A) or a method for cutting the waist elastic member 11 with a gather cutter 60 (see FIG. 8) can be adopted.

The weakening treatment may be performed before step 8 of attaching the absorber 20 described later.

(2) Step 3 to Step 7

Figure 10:
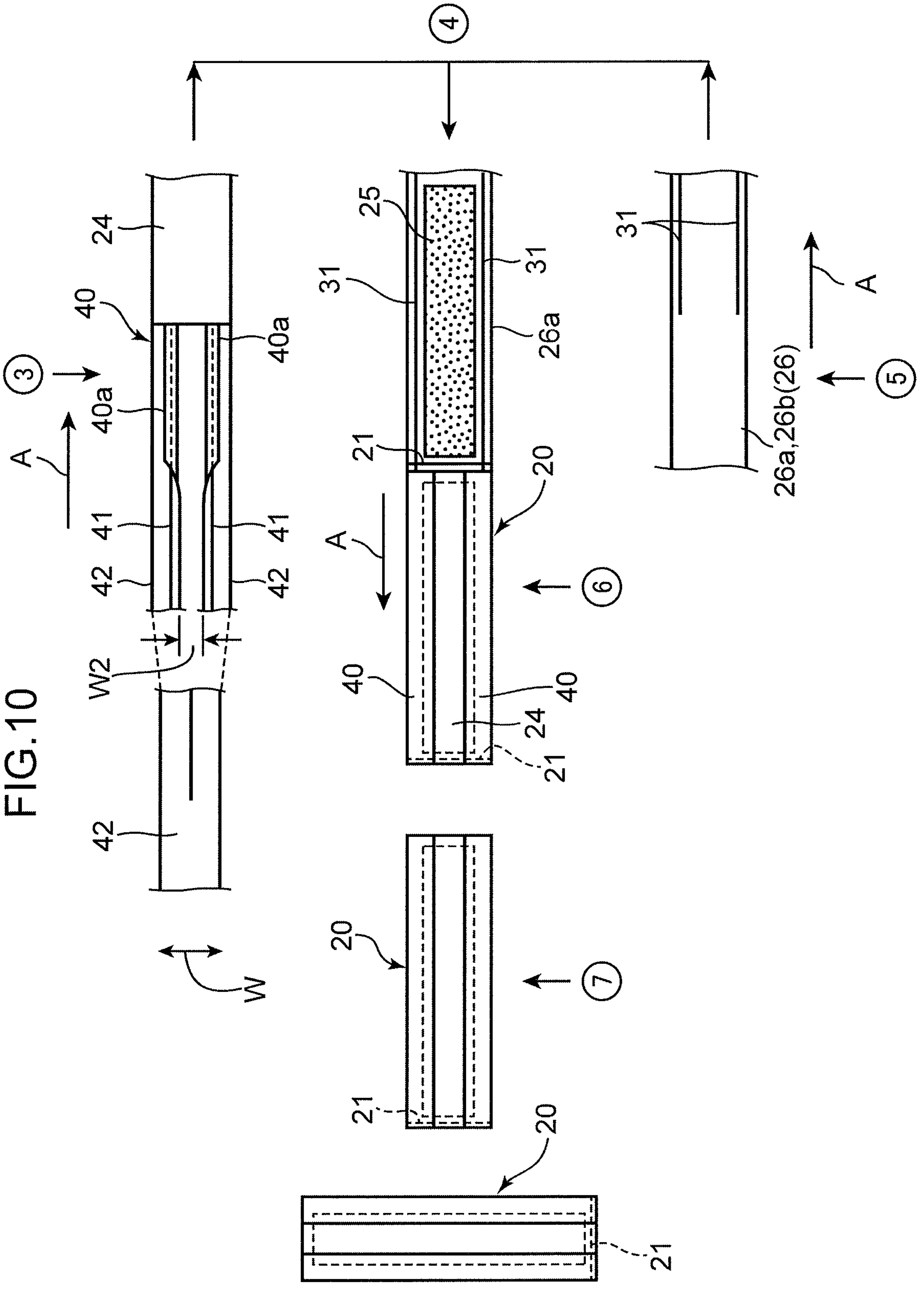
FIG. 10 is a plan view of a production situation of step 3 to step 7.

Step 3 to step 7 are an example of a step of producing the absorber 20 in a vertical flow state as illustrated in FIG. 10. In the vertical flow state of FIG. 10, the MD direction A coincides with the waist orthogonal direction, and the CD direction W coincides with the waist width direction.

(Step 3)

In step 3, a front sheet in-process item where a continuous body of the front sheet 24 in which the plurality of front sheets 24 are continuous and a continuous body of the three-dimensional gather 40 in which the plurality of three-dimensional gathers 40 are continuous are combined is formed.

Figure 18A:
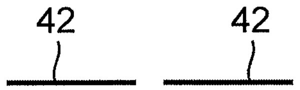
FIG. 18A is a cross-sectional view of a main part in a production process of step 3, and illustrates a state of cutting a sheet for a rising flap.
Figure 18B:
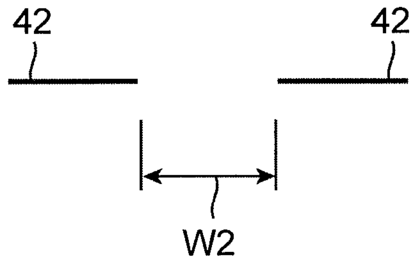
FIG. 18B is a cross-sectional view of a main part in the production process of step 3, and illustrates a state where the rising flap having been cut is widened at a regular interval in a width direction.
Figure 18C:
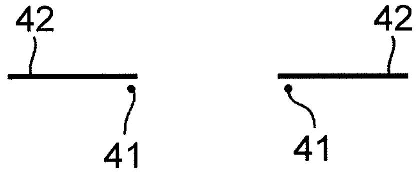
FIG. 18C is a cross-sectional view of a main part in the production process of step 3, and illustrates a state where a three-dimensional gather elastic member is disposed on the rising flap.

In FIGS. 8, 10, and 18, a non-woven fabric sheet for forming a continuous body of the rising flap 42 in which the plurality of rising flaps 42 are continuous is continuously fed in the MD direction A and cut in the MD direction A by a slitter 62 (see FIG. 18A). The continuous body of the pair of belt-shaped rising flaps 42 having been cut is widened at a constant interval W2 in the CD direction W (see FIG. 18B). Next, the three-dimensional gather elastic member 41 is disposed in an expanded state in the MD direction A in an inner edge portion of each continuous body of the pair of rising flaps 42 (edge portion of the continuous body of one rising flap 42 closer to the continuous body of the other rising flap 42 in the CD direction W) (see FIG. 18C).

Figure 18D:
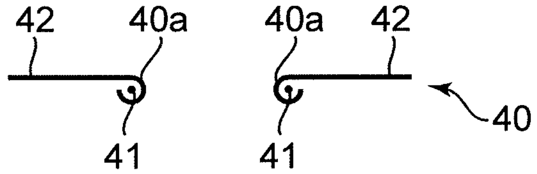
FIG. 18D is a cross-sectional view of a main part in the production process of step 3, and illustrates a state of producing a three-dimensional gather by joining the three-dimensional gather elastic member in an inner bent portion of the rising flap.

As illustrated in FIG. 18D, the inner edge portion where the three-dimensional gather elastic member 41 of the continuous body of the rising flap 42 is disposed is folded back such that the three-dimensional gather elastic member 41 is tucked inside the rising flap 42 by a sailor 63. Due to this, an inner bent portion 40*a* is formed. At this time, the three-dimensional gather elastic member 41 is joined by adhesion using a hot melt adhesive, welding by heat sealing, ultrasonic welding, or the like to the continuous body of the rising flap 42 in a state of being tucked in the inner bent portion 40*a* in an expanded state in the MD direction A. Due to this, the continuous body of the three-dimensional gather 40 is produced.

Figure 18E:
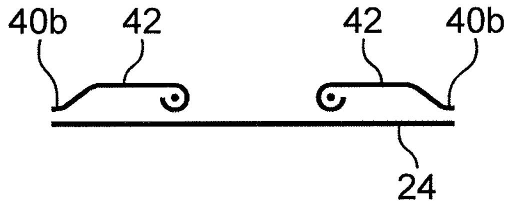
FIG. 18E is a cross-sectional view of a main part in the production process of step 3, and illustrates a state where the three-dimensional gather is joined to the front sheet.

Thereafter, an outer edge portion 40*b* of the continuous body of the three-dimensional gather 40 (edge portion of the continuous body of one rising flap 42 far from the continuous body of the other rising flap 42 in the CD direction W) is joined by adhesion using a hot melt adhesive, welding by heat sealing, ultrasonic welding, or the like to both outer edge portions in the CD direction W of the continuous body of the front sheet 24 continuously fed in the MD direction A, thereby producing the front sheet in-process item (see FIG. 18E).

Next, a method for producing the continuous body of the front sheet 24 will be described. First, the configuration of a production device 85 of the continuous body of the front sheet 24 will be described.

Figure 11:
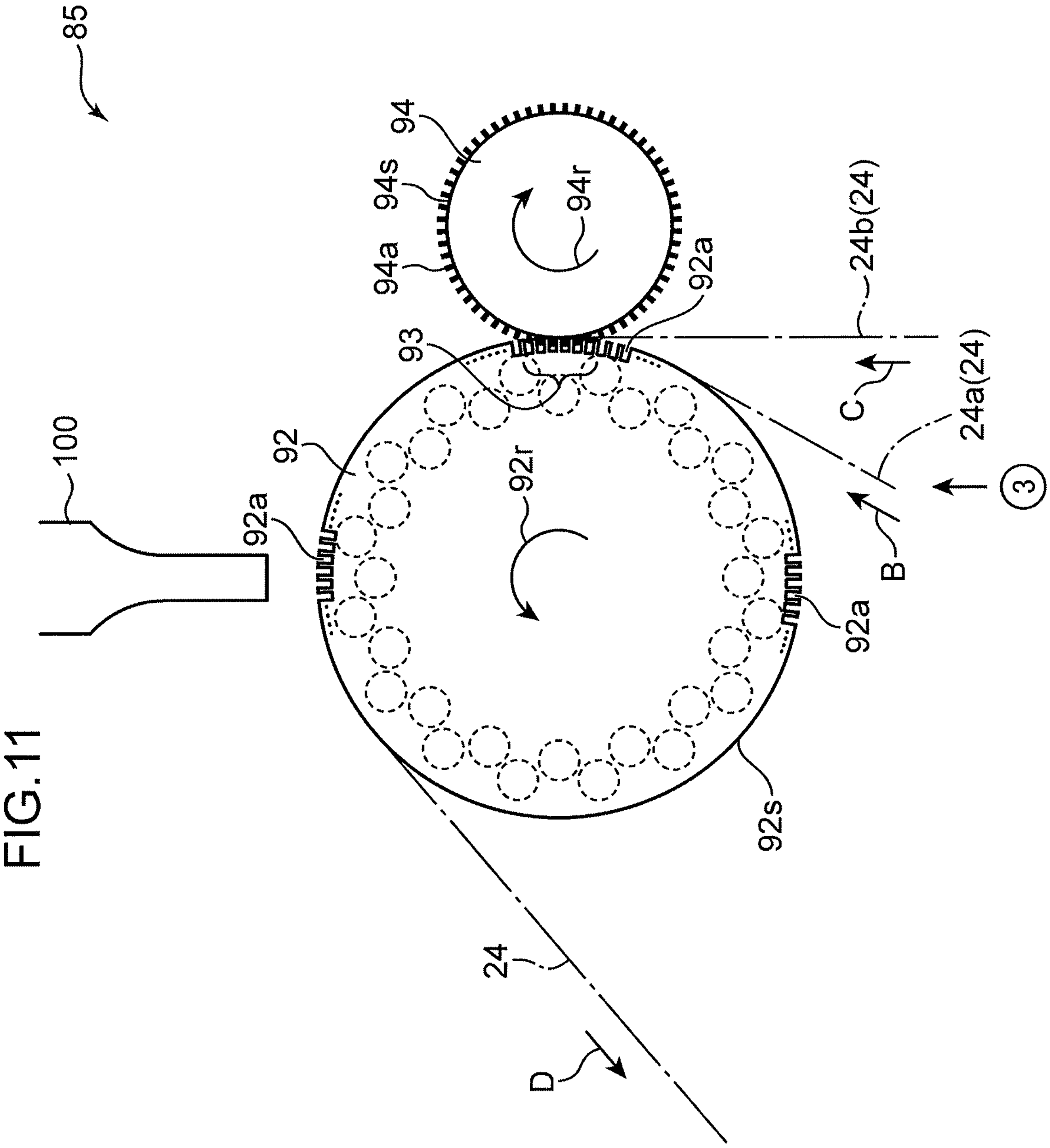
FIG. 11 is a schematic view of a front sheet production device.

FIG. 11 is a schematic diagram of the production device 85. As illustrated in FIG. 11, the production device 85 includes first and second rolls 92 and 94 disposed adjacent to each other, and a joint device 100 disposed adjacent to the first roll 92.

The first roll 92 has, on a cylindrical outer circumferential surface 92*s*, a plurality of concave portions 92*a* that are recessed radially inward from the outer circumferential surface 92*s* and mesh with a plurality of convex portions 94*a* described later. The second roll 94 has, on a cylindrical outer circumferential surface 94*s*, the plurality of convex portions 94*a* protruding radially outward from the outer circumferential surface 94*s*. The shape of the convex portion 94*a* has, for example, a hemispherical shape in which the protruding tip end is a hemispherical surface, and may be another shape such as, for example, a rectangular parallelepiped shape, a cylindrical shape, or a truncated pyramid shape. The first and second rolls 92 and 94 rotate in opposite directions to each other as indicated by arrows 92*r* and 94*r*. The concave portion 92*a* of the first roll 92 and the convex portion 94*a* of the second roll 94 mesh with each other in a mesh region 93. More specifically, the first and second rolls 92 and 94 rotate such that the concave portion 92*a* and the convex portion 94*a* mesh with each other in a state where a gap is formed between the both in the mesh region 93, that is, in a state where they mesh with each other in a non-contact state.

The joint device 100 is an ultrasonic sealing device, and produces the continuous body of the front sheet 24 by joining two continuous bodies of a continuous body of the front-side first non-woven fabric 24*a* where a plurality of the front-side first non-woven fabrics 24*a* are continuous and a continuous body of the front-side second non-woven fabric 24*b* where a plurality of the front-side second non-woven fabrics 24*b* are continuous. The joint means can be adhesion using a hot melt adhesive or welding by heat sealing, but ultrasonic welding is preferable. In the case of using ultrasonic welding, as compared with the case of using an adhesive or heat sealing, stiffness of the front sheet 24 is suppressed, which is preferable.

Use of the production device 85 makes it possible to form the irregularity shape 20*a* by overlapping the continuous body of the front-side first non-woven fabric 24*a* and the continuous body of the front-side second non-woven fabric 24*b*. Furthermore, use of the production device 85 makes it possible to join the continuous body of the front-side first non-woven fabric 24*a* and the continuous body of the front-side second non-woven fabric 24*b* in a state of maintaining the irregularity shape 20*a* of the continuous body of the front-side first non-woven fabric 24*a* and in a state where tension is applied to the continuous body of the front-side second non-woven fabric 24*b* so that the undulation of the continuous body of the front-side second non-woven fabric 24*b* becomes gentler than the irregularity shape 20*a* of the continuous body of the front-side first non-woven fabric 24*a*. The method for producing such a continuous body of the front sheet 24 will be further described.

Figure 12A:
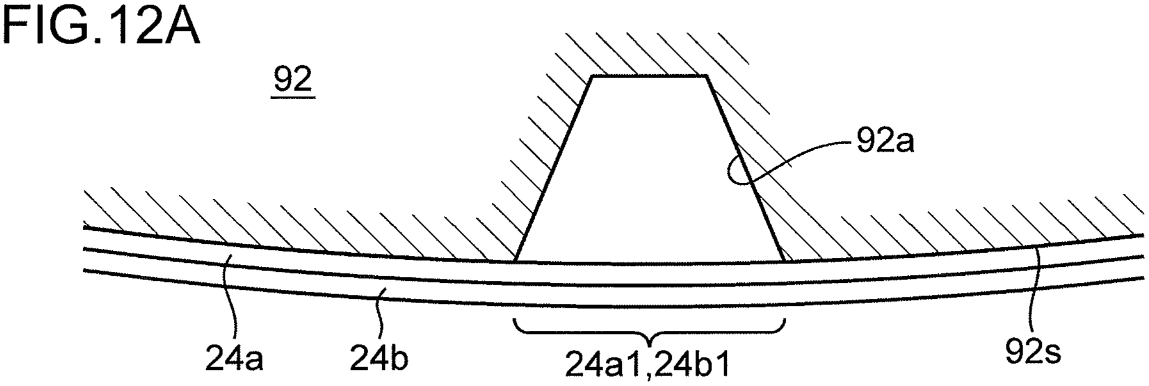
FIG. 12A is an explanatory view of a formation process of an irregularity shape on a front sheet, and illustrates a state where a front-side first non-woven fabric and a front-side second non-woven fabric are wound around an outer circumferential surface of a first roll.

As illustrated in FIGS. 11 and 12A, the continuous body of the front-side first non-woven fabric 24*a* is wound around the outer circumferential surface 92*s* of the first roll 92 prior to the continuous body of the front-side second non-woven fabric 24*b*. Since the concave portion 92*a* of the first roll 92 is connected to a negative pressure source, the continuous body of the front-side first non-woven fabric 24*a* is adsorbed and held along the outer circumferential surface 92*s* of the first roll 92. Next, the continuous body of the front-side second non-woven fabric 24*b* is wound around the outer circumferential surface 92*s* of the first roll 92 via the continuous body of the front-side first non-woven fabric 24*a* in the mesh region 93 or a position slightly upstream thereof. That is, the continuous body of the front-side second non-woven fabric 24*b* is overlapped on the outer side of the continuous body of the front-side first non-woven fabric 24*a* in the mesh region 93 or the position slightly upstream thereof. As described above, the continuous body of the front-side first non-woven fabric 24*a* and the continuous body of the front-side second non-woven fabric 24*b* are guided to the first roll 92 along the directions indicated by arrows B and C (FIG. 11) so that the continuous body of the front-side first non-woven fabric 24*a* and the continuous body of the front-side second non-woven fabric 24*b* are wound around the outer circumferential surface 92*s* of the first roll 92.

Parts 24*a*1 and 24*b*1 covering the concave portion 92*a* in the continuous body of the front-side first non-woven fabric 24*a* and the continuous body of the front-side second non-woven fabric 24*b* are pushed into the concave portion 92*a* by the convex portion 94*a* in a state of being overlapped in the mesh region 93. Due to this, parts 24*a*2 and 24*b*2 pushed into the concave portion 92*a* are formed in the continuous body of the front-side first non-woven fabric 24*a* and the continuous body of the front-side second non-woven fabric 24*b* (see FIGS. 12A and 12B). That is, the plurality of parts 24*a*2 and 24*b*2 are formed on the continuous body of the superimposed front-side first non-woven fabric 24*a* and the continuous body of the front-side second non-woven fabric 24*b*, thereby forming the irregularity shape 20*a*.

As described above, the continuous body of the front-side first non-woven fabric 24*a* and the continuous body of the front-side second non-woven fabric 24*b* are overlapped in the mesh region 93, and are joined by the joint device 100 on a downstream side (right side in FIGS. 12A to 12C) relative to the mesh region 93. As described above, due to the frictional resistance generated between the both continuous bodies when the continuous body of the front-side first non-woven fabric 24*a* and the continuous body of the front-side second non-woven fabric 24*b* are overlapped, relative movement of the both continuous bodies is suppressed. Furthermore, the relative movement between the continuous body of the front-side first non-woven fabric 24*a* and the continuous body of the front-side second non-woven fabric 24*b* is restricted by the joint. On the other hand, the continuous body of the front-side first non-woven fabric 24*a* and the continuous body of the front-side second non-woven fabric 24*b* are conveyed in a non-contact and non-joint state as illustrated in FIG. 11 on an upstream side of the mesh region 93 (left side in FIGS. 12A to 12C). Therefore, the relative movement between the continuous body of the front-side first non-woven fabric 24*a* and the continuous body of the front-side second non-woven fabric 24*b* is allowed on the upstream side of the mesh region 93. Therefore, the relative movement between the continuous body of the front-side first non-woven fabric 24*a* and the continuous body of the front-side second non-woven fabric 24*b* is more likely to occur on the upstream side compared with the downstream side of the mesh region 93.

Figure 12B:
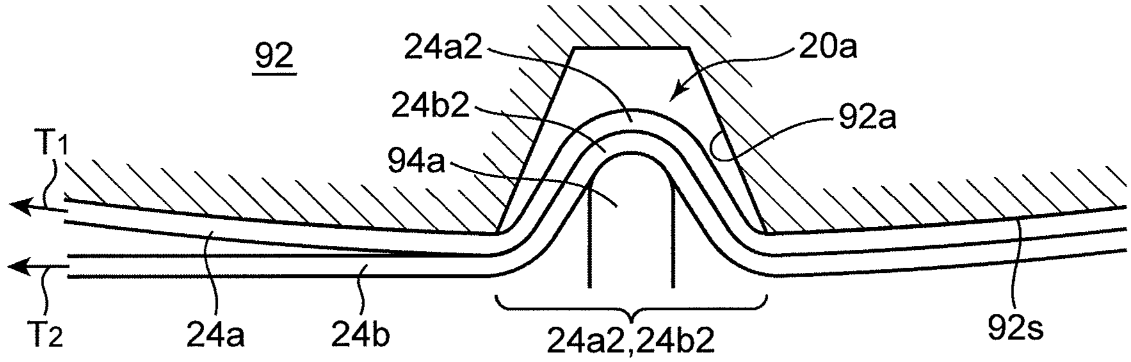
FIG. 12B is an explanatory view of the formation process of the irregularity shape on the front sheet, and illustrates a state where the front-side first non-woven fabric and the front-side second non-woven fabric are pushed into a concave portion of the first roll.
Figure 12C:
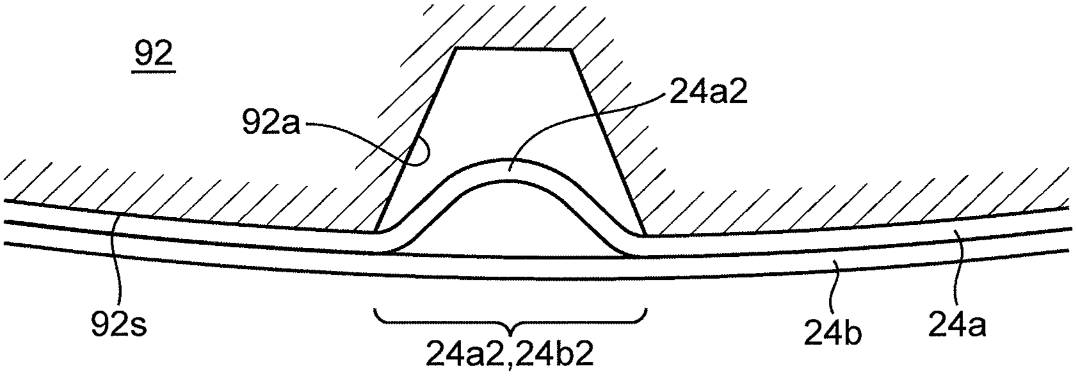
FIG. 12C is an explanatory view of the formation process of the irregularity shape on the front sheet, and illustrates a state where the irregularity shape is formed only on the front-side first non-woven fabric.

As illustrated in FIG. 12B, the convex portion 94*a* meshed with the concave portion 92*a* gradually comes out of the concave portion 92*a* in accordance with the rotation of the first roll 92. As described above, the air in the concave portion 92*a* is sucked. Therefore, by inserting the convex portion 94*a* into the concave portion 92*a*, the plurality of parts 24*a*2 of the continuous body of the front-side first non-woven fabric 24*a* remain in the concave portion 92*a* and are shaped. On the other hand, as illustrated in FIG. 12C, the part 24*b*2 of the continuous body of the front-side second non-woven fabric 24*b* is pulled out from the concave portion 92*a* by being pulled by the tension applied to the continuous body of the front-side second non-woven fabric 24*b* as the convex portion 94*a* gradually comes out of the concave portion 92*a*. Therefore, the undulation formed on the continuous body of the front-side second non-woven fabric 24*b* becomes gentler than the irregularity shape formed on the continuous body of the front-side first non-woven fabric 24*a*.

When the convex portion 94*a* completely comes out of the concave portion 92*a*, the part 24*b*2 pushed into the concave portion 92*a* of the continuous body of the front-side second non-woven fabric 24*b* is completely pulled out from the concave portion 92*a* by the tension applied to the continuous body of the front-side second non-woven fabric 24*b*. Therefore, the undulation formed on the continuous body of the front-side second non-woven fabric 24*b* becomes gentler than the irregularity shape 20*a* formed on the continuous body of the front-side first non-woven fabric 24*a*. On the other hand, since the part 24*a*2 pushed into the concave portion 92*a* of the continuous body of the front-side first non-woven fabric 24*a* remains in the concave portion 92*a* as described above, the irregularity shape 20*a* is formed only in the continuous body of the front-side first non-woven fabric 24*a*.

In order to form the irregularity shape 20*a* only on the continuous body of the front-side first non-woven fabric 24*a* as described above, tension T2 applied to the continuous body of the front-side second non-woven fabric 24*b* is set to be larger than tension T1 applied to the continuous body of the front-side first non-woven fabric 24*a* (T1<T2). Due to this, the part 24*b*2 of the continuous body of the front-side second non-woven fabric 24*b* is pulled out from the concave portion 92*a* with relative movement with respect to the continuous body of the front-side first non-woven fabric 24*a* in response to the convex portion 94*a* coming out of the concave portion 92*a*. Therefore, the continuous body of the front-side first non-woven fabric 24*a* is provided with the irregularity shape meanwhile the continuous body of the front-side second non-woven fabric 24*b* is provided with a gentle undulation as compared with the irregularity shape 20*a* of the continuous body of the front-side first non-woven fabric 24*a* (in the present embodiment, the continuous body of the front-side second non-woven fabric 24*b* that is substantially flat is formed).

As illustrated in FIG. 11, the continuous body of the front-side first non-woven fabric 24*a* is conveyed in a state of being in contact with the outer circumferential surface 92*s* of the first roll 92 in the position on the upstream side of the mesh region 93 and being sucked into the concave portion 92*a*. Due to this, a frictional force is generated between the part between the part on the upstream side of the mesh region 93 of the continuous body of the front-side first non-woven fabric 24*a* and the joint device 100 and the first roll 92. Therefore, the part 24*a*2 pushed into the concave portion 92*a* of the continuous body of the front-side first non-woven fabric 24*a* easily remains in the concave portion 92*a* due to the frictional force even if the convex portion 94*a* comes out of the concave portion 92*a*. Therefore, the irregularity shape 20*a* can be effectively formed on the continuous body of the front-side first non-woven fabric 24*a*.

On the other hand, as described above, the continuous body of the front-side second non-woven fabric 24*b* is wound around the outer circumferential surface 92*s* of the first roll 92 via the continuous body of the front-side first non-woven fabric 24*a* in the mesh region 93 or a position slightly upstream thereof. That is, the continuous body of the front-side second non-woven fabric 24*b* is conveyed in a non-contact state with respect to the continuous body of the front-side first non-woven fabric 24*a*, the first roll 92, and the second roll 94 in the position on the upstream side of the mesh region 93. Therefore, a frictional force is not generated with respect to the continuous body of the front-side first non-woven fabric 24*a*, the first roll 92, and the second roll 94 in the part on the upstream side of the mesh region 93 of the continuous body of the front-side second non-woven fabric 24*b*. Therefore, the part on the upstream side of the mesh region 93 of the continuous body of the front-side second non-woven fabric 24*b* can be easily moved relatively to the continuous body of the front-side first non-woven fabric 24*a* and the first roll 92. Therefore, in order to pull out the part 24*b*2 of the continuous body of the front-side second non-woven fabric 24*b* from the concave portion 92*a*, the tension T2 can facilitate movement of the mesh region 93 of the continuous body of the front-side second non-woven fabric 24*b* to the upstream side.

As illustrated in FIG. 12B, since the continuous body of the front-side second non-woven fabric 24*b* is interposed between the continuous body of the front-side first non-woven fabric 24*a* and the convex portion 94*a*, the continuous body of the front-side first non-woven fabric 24*a* is not in contact with the convex portion 94*a*. Due to this, no frictional force is generated between the continuous body of the front-side first non-woven fabric 24*a* and the convex portion 94*a*, and therefore when the convex portion 94*a* comes out of the concave portion 92*a*, the continuous body of the front-side first non-woven fabric 24*a* can be suppressed from following the convex portion 94*a*. Therefore, even if the tension T1 applied to the continuous body of the front-side first non-woven fabric 24*a* is set to be extremely small, the part 24*a*2 pushed into the concave portion 92*a* of the continuous body of the front-side first non-woven fabric 24*a* can remain in the concave portion 92*a*. On the other hand, since the part 24*b*2 pushed into the concave portion 92*a* of the continuous body of the front-side second non-woven fabric 24*b* is in contact with the convex portion 94*a*, when the convex portion 94*a* comes out of the concave portion 92*a*, the continuous body of the front-side second non-woven fabric 24*b* easily follows the convex portion 94*a*. Therefore, the part 24*b*2 of the continuous body of the front-side second non-woven fabric 24*b* can be efficiently pulled out from the concave portion 92*a* in combination with the tension T2.

As described above, the first and second rolls 92 and 94 rotate in the state where the continuous body of the front-side first non-woven fabric 24*a* and the continuous body of the front-side second non-woven fabric 24*b* are tucked between the first and second rolls 92 and 94. With this rotation, the plurality of convex portions 94*a* and the plurality of concave portions 92*a* sequentially mesh with each other, whereby a plurality of raised parts 24*a*2 are intermittently formed on the continuous body of the front-side first non-woven fabric 24*a*. Due to this, the irregularity shape 20*a* is formed on the continuous body of the front-side first non-woven fabric 24*a*. On the other hand, the continuous body of the front-side second non-woven fabric 24*b* is pulled out from the concave portion 92*a* by the tension T2 as described above, thereby being formed in a substantially flat surface shape.

Next, the continuous body of the front-side second non-woven fabric 24*b* having a substantially flat surface shape is joined to the outer surface opposite to the surface facing the skin surface side in the continuous body of the front-side first non-woven fabric 24*a* having the irregularity shape 20*a*. Specifically, the concave portion of the continuous body of the front-side first non-woven fabric 24*a* and the continuous body of the front-side second non-woven fabric 24*b* are joined. The continuous body of the front-side first non-woven fabric 24*a* and the continuous body of the front-side second non-woven fabric 24*b* are joined by passing the continuous body of the front-side first non-woven fabric 24*a* and the continuous body of the front-side second non-woven fabric 24*b* between the first roll 92 and an ultrasonic horn of the joint device 100. Due to this, the continuous body of the front sheet 24 is formed. The continuous body of the front sheet 24 is separated from the first roll 92 as indicated by arrow D (FIG. 11) and conveyed to a subsequent step.

According to the above production method, the irregularity shape 20*a* is simultaneously formed on two non-woven fabrics in a state where the front-side first non-woven fabric 24*a* and the front-side second non-woven fabric 24*b* to be joined to each other are overlapped. Then, the front-side second non-woven fabric 24*b* is joined to the front-side first non-woven fabric 24*a* while maintaining the irregularity shape 20*a* of the front-side first non-woven fabric 24*a* in a state where the tension is applied to the front-side second non-woven fabric 24*b* so that undulation of the front-side second non-woven fabric 24*b* becomes gentle among the two non-woven fabrics provided with the irregularity shape 20*a*. Therefore, the step and the production device can be simplified as compared with the case where the step of forming the irregularity shape 20*a* on the front-side first non-woven fabric 24*a* and the step of forming the front-side second non-woven fabric 24*b* having a gentle undulation are separately performed, and the step of overlapping the front-side first non-woven fabric 24*a* and the front-side second non-woven fabric 24*b* having been subjected to these steps is further performed. That is, according to the above production method, for example, different undulation shapes can be formed on the same line for the front-side first non-woven fabric 24*a* and the front-side second non-woven fabric 24*b*, the number of lines can be reduced as compared with a case where a line for producing the front-side first non-woven fabric 24*a* and a line for producing the front-side second non-woven fabric 24*b* are separately provided, and a configuration in which the separate lines are converged can be omitted.

In the above, the continuous body of the front sheet 24 where only the continuous body of the front-side first non-woven fabric 24*a* has the irregularity shape 20*a* is formed. Unlike this, by the following production step, the continuous body of the front sheet 24 where both the continuous body of the front-side first non-woven fabric 24*a* and the continuous body of the front-side second non-woven fabric 24*b* have an irregularity shape may be formed. Specifically, after passing through the mesh region 93, the tension of the continuous body of the front-side second non-woven fabric 24*b* can be adjusted so that a part or entirety of the part 24*b*2 pushed into the concave portion 92*a* of the continuous body of the front-side second non-woven fabric 24*b* remains in the concave portion 92*a*. Due to this, a part or entirety of the part 24*b*2 pushed into the concave portion 92*a* of the continuous body of the front-side second non-woven fabric 24*b* can remain in the concave portion 92*a*. In this manner, both the continuous body of the front-side first non-woven fabric 24*a* and the continuous body of the front-side second non-woven fabric 24*b* are shaped, and the continuous body of the front sheet 24 having an irregularity shape can be formed. In this case, it is not necessary to prepare a roll for shaping the continuous body of the front-side second non-woven fabric 24*b* separately from the roll for shaping the continuous body of the front-side first non-woven fabric 24*a*.

As still another form, in addition to or instead of the continuous body of the front-side second non-woven fabric 24*b*, a member that is plastically deformed when the convex portion 94*a* and the concave portion 92*a* mesh with each other can also be applied. In this manner, when passing through the mesh region 93, the continuous body of the front-side second non-woven fabric 24*b* or the plastically deforming member is plastically deformed, whereby the continuous body of the front-side first non-woven fabric 24*a* can remain in the concave portion 92*a* by this plastically deformed part. Therefore, both the continuous body of the front-side first non-woven fabric 24*a* and the continuous body of the front-side second non-woven fabric 24*b* are shaped, and an irregularity shape can be formed in the continuous body of the front-side first non-woven fabric 24*a* and the continuous body of the front-side second non-woven fabric 24*b*.

In the above step, inside of the concave portion 92*a* of at least the first roll 92 may be heated at a temperature lower than the melting point of the continuous body of the front-side first non-woven fabric 24*a*. This makes it possible to more reliably shape the continuous body of the front-side first non-woven fabric 24*a*. For example, by providing a heater inside the first roll 92, it is possible to heat the surroundings of the concave portion 92*a*. In addition to or instead of heating of the first roll 92, the second roll 94 (particularly around the convex portion 94*a*) can be heated at a temperature lower than the melting point of the continuous body of the front-side first non-woven fabric 24*a*.

Unlike the above, the front-side first non-woven fabric 24*a* having a flat surface shape can be used as a continuous body of the front sheet 24.

(Step 4)

In step 4, the continuous body of the core 25 where the plurality of cores 25 are continuous is formed, and the core 25 is produced using the continuous body of the core 25. The continuous body of the core 25 and the method for producing the core 25 will be described with reference to FIGS. 13 to 15.

In the wearing article 1, the continuous body of the core 25 is formed by laminating two of the continuous body of the core-side first non-woven fabric S1 where the plurality of core-side first non-woven fabric S1 are continuous and the continuous body of the core-side second non-woven fabric S2 where the plurality of core-side second non-woven fabric S2 are continuous. In the examples of FIGS. 5A to 5C, the continuous body of the core-side first non-woven fabric S1 is produced by holding the SAP such that the holding region R2 holding the SAP and the first low-density region R11 holding the SAP having a lower density than the SAP in the holding region R2 are formed. In the examples of FIGS. 6A to 7C, the continuous body of the core-side first non-woven fabric S1 is produced by holding the SAP such that the holding region R2, the first low-density region R11, and the second low-density region R12 are formed. A method for producing the continuous body of such the core 25 will be described below. As described above, the continuous body of the core 25 can also be formed from a continuous body of one core-side non-woven fabric.

Figure 13:
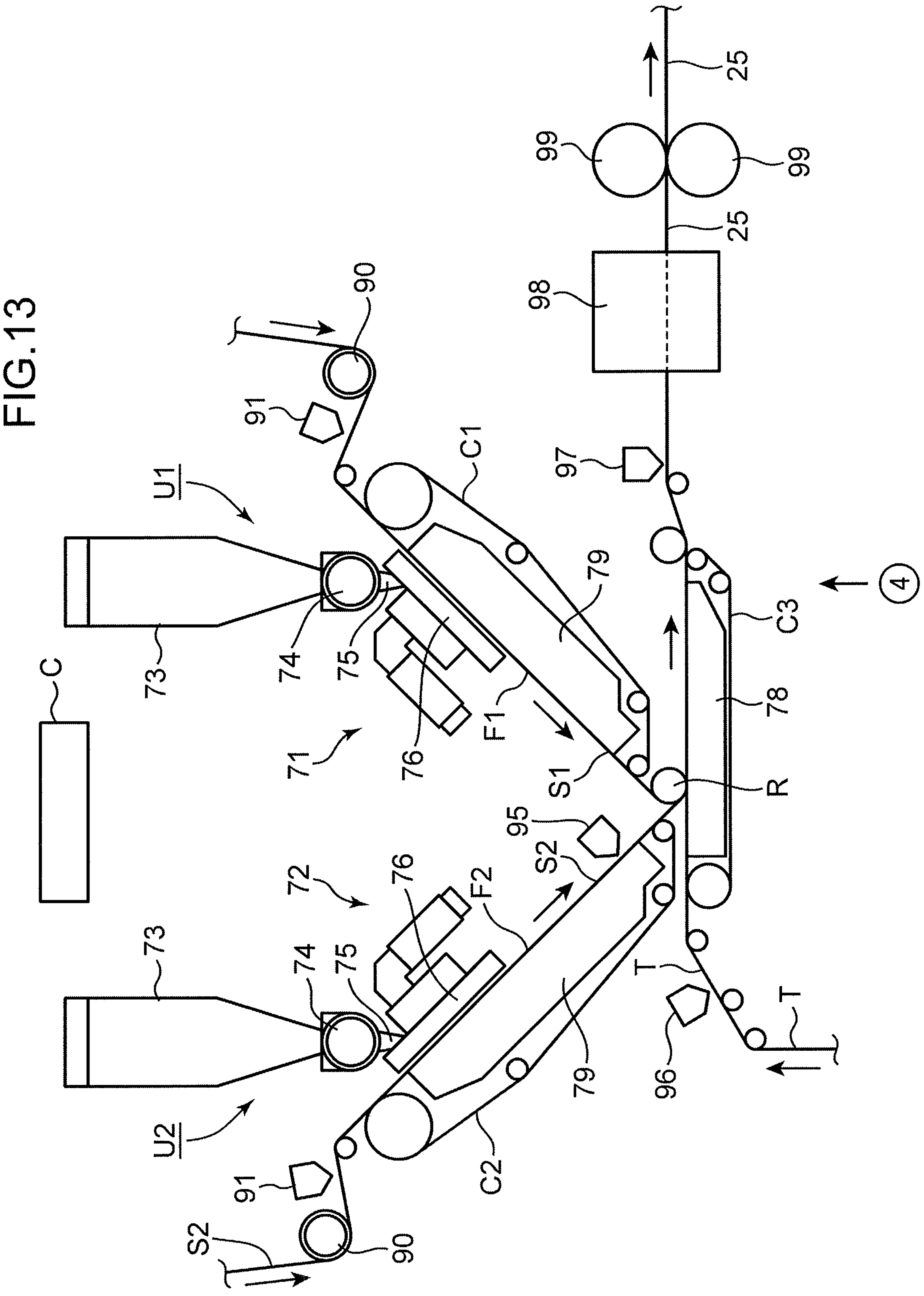
FIG. 13 is a schematic view of a production device of a core.

As illustrated in FIG. 13, the production device of the continuous body of the core 25 includes first and second units U1 and U2, a lamination roller R, a control device C, a lamination conveyor C3, a third applicator 96, a fourth applicator 97, a folder 98, and a pair of pressure welding rollers 99. The first and second units U1 and U2 have the same structure as each other, and are disposed substantially plane-symmetrically with respect to a plane including a central axis of the lamination roller R.

The first unit U1 includes a first conveyor C1, a raising roller 90, a first applicator 91, a first scatter device 71, and a negative pressure case 79 provided on the first conveyor C1. The second unit U2 includes a second conveyor C2, the raising roller 90, the first applicator 91, a second applicator 95, a second scatter device 72, and the negative pressure case 79 provided on the second conveyor C2. The control device C drives and controls both the first and second units U1 and U2 to laminate the continuous body of the two core-side non-woven fabrics S1 and S2, thereby producing the continuous body of the core 25. Note that when the continuous body of the core 25 is formed of a continuous body of one core-side non-woven fabric, the control device C is only required to control driving of one of the two units U1 and U2.

In the present embodiment, the continuous body of the core 25 includes the continuous body of the core-side first non-woven fabric S1 and the continuous body of the core-side second non-woven fabric S2. The continuous body of the core-side first non-woven fabric S1 and the continuous body of the core-side second non-woven fabric S2 include a diffusion layer 81 serving as a base and a short fiber layer 82 laminated on the diffusion layer 81 (see FIGS. 14 and 15). The short fiber layer 82 is a layer of a non-woven fabric formed of a short fiber, and is a layer of a non-woven fabric subjected to air through processing, for example. Such a non-woven fabric layer can be formed by arraying short fibers and blowing hot air to them, and is also referred to as an air-laid non-woven fabric. On the other hand, the diffusion layer 81 has a thickness smaller than that of the short fiber layer 82, and has a fiber density higher than that of the short fiber layer 82. This diffusion layer 81 has high diffusivity in the plane direction and can allow liquid to permeate a wide range.

Figure 15A:
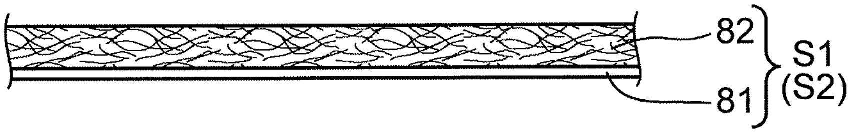
FIG. 15A is a cross-sectional view illustrating a process for producing the core, and illustrates a state before raising of the core-side first non-woven fabric and the core-side second non-woven fabric.
Figure 15B:
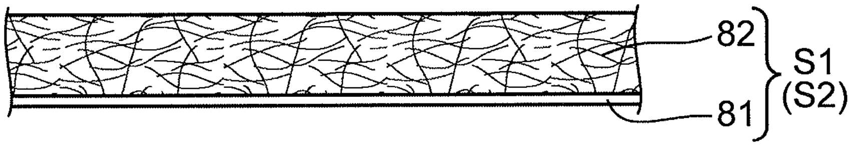
FIG. 15B is a cross-sectional view illustrating a process for producing the core, and illustrates a state after raising of the core-side first non-woven fabric and the core-side second non-woven fabric.

The continuous body of the core-side first non-woven fabric S1 and the continuous body of the core-side second non-woven fabric S2 are supplied to the raising roller 90. The raising roller is a roller having an outer surface on which a large number of teeth are formed, and rotates at a peripheral speed lower than the conveyance speed of the continuous body of the core-side first non-woven fabric S1 and the continuous body of the core-side second non-woven fabric S2. By setting the speed difference between the conveyance speed and the peripheral speed as described above, the raising roller 90 can raise, as illustrated in FIG. 15B, the short fiber layer 82 of the continuous body of the core-side first non-woven fabric S1 and the continuous body of the core-side second non-woven fabric S2 illustrated in FIG. 15A. The speed difference between the conveyance speed and the peripheral speed is not necessarily limited to a speed difference in the same direction, and includes a speed difference in a case where the conveyance direction and the rotation direction are opposite directions. Due to the raising, the short fiber layer 82 of the continuous body of the core-side first non-woven fabric S1 and the continuous body of the core-side second non-woven fabric S2 is brought into a raised state as illustrated in FIG. 15B from the lowering state illustrated in FIG. As a result, the bulk density of the continuous body of the core-side first non-woven fabric S1 and the continuous body of the core-side second non-woven fabric S2 decreases, and the thickness of the continuous body of the core-side first non-woven fabric S1 and the continuous body of the core-side second non-woven fabric S2 increases. That is, in the continuous body of the core-side first non-woven fabric S1 and the continuous body of the core-side second non-woven fabric S2, a gap for supporting an SAP 80 is formed by the raising.

As illustrated in FIG. 13, the first applicator 91 for applying an adhesive for supporting the SAP 80 on the continuous body of the core-side first non-woven fabric S1 and the continuous body of the core-side second non-woven fabric S2 is provided between the raising roller 90 and the first and second conveyors C1 and C2 described later in the conveyance direction. An adhesive is applied by the first applicator 91 to the front surface of the raised short fiber layer 82 of the continuous body of the core-side first non-woven fabric S1 and the continuous body of the core-side second non-woven fabric S2.

After application of the adhesive, the continuous body of the core-side first non-woven fabric S1 is conveyed along a flat first inclined surface F1 of the first conveyor C1 while being sucked by the negative pressure supplied by the negative pressure case 79. The continuous body of the core-side second non-woven fabric S2 is conveyed along a flat second inclined surface F2 having an inclination opposite to that of the first inclined surface F1 of the second conveyor C2 while being sucked by the negative pressure supplied by the negative pressure case 79.

Figure 14:
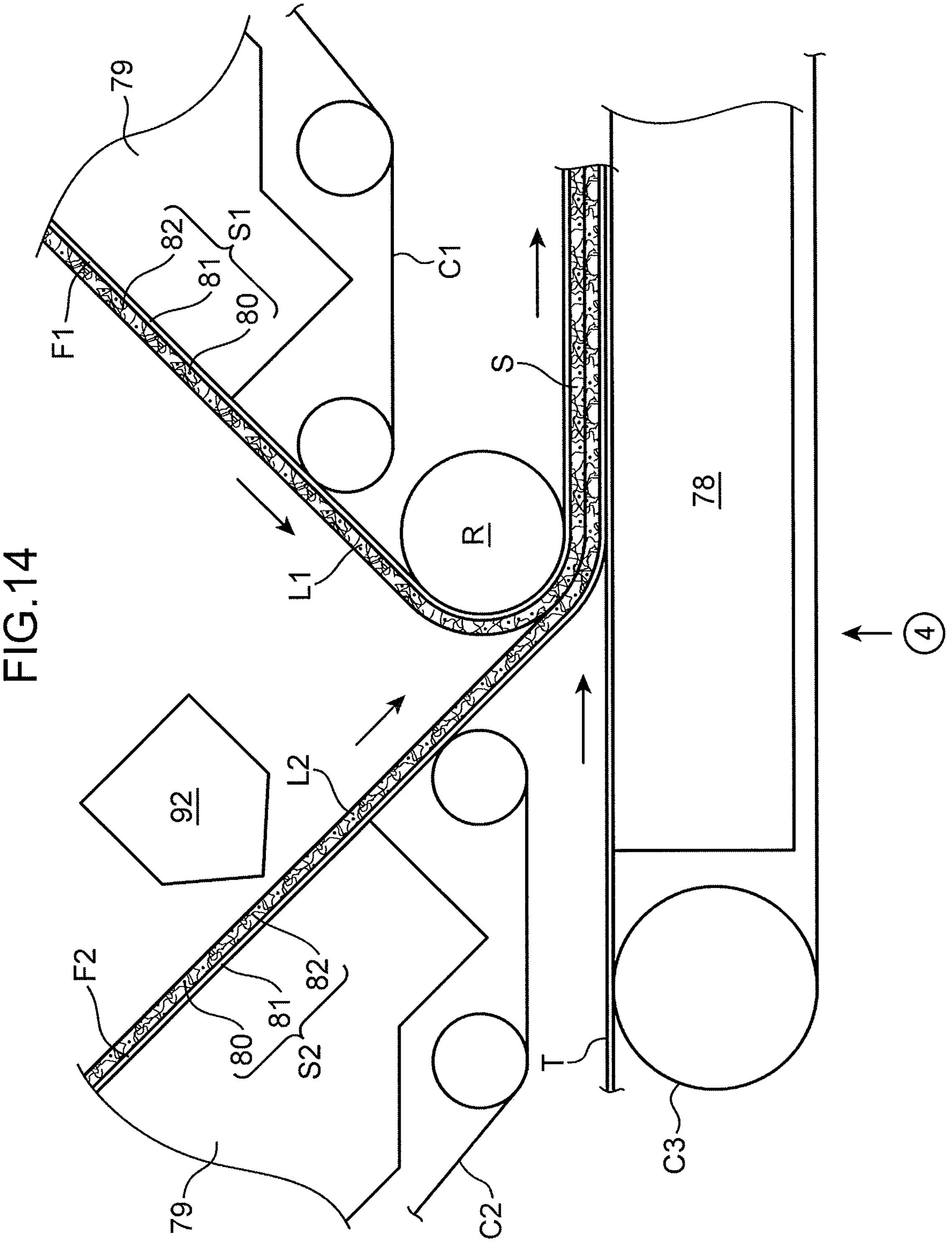
FIG. 14 is an explanatory view of a process for producing a core by laminating a core-side first non-woven fabric and a core-side second non-woven fabric.
Figure 15C:
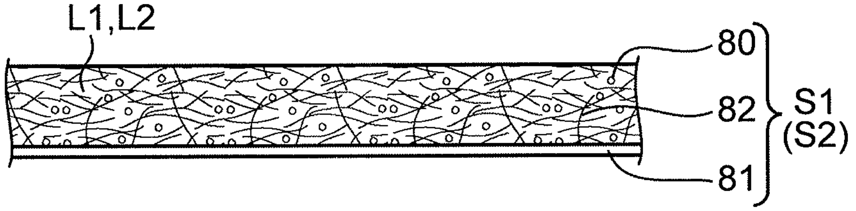
FIG. 15C is a cross-sectional view illustrating a process for producing the core, and illustrates a state where the core-side first non-woven fabric and the core-side second non-woven fabric support the SAP.

Each of the first and second scatter devices 71 and 72 in FIG. 13 scatters the SAP 80 (see FIG. 14), which is an absorbent particulate matter, onto the upper surface of the continuous body of the core-side first non-woven fabric S1 conveyed along the first inclined surface F1 and the continuous body of the core-side second non-woven fabric S2 conveyed along the second inclined surface F2. During this scattering, the continuous body of the core-side first non-woven fabric S1 and the continuous body of the core-side second non-woven fabric S2 are sucked by the negative pressure case 79, and thus the SAP 80 having been scattered enters a gap of the short fiber layer 82 formed by raising as illustrated in FIGS. 14 and 15C. The SAP 80 adheres to the continuous body of the core-side first non-woven fabric S1 and the continuous body of the core-side second non-woven fabric S2 by the adhesive applied by the first applicator 91.

A first absorption layer L1 is formed of the short fiber layer 82 supporting the SAP 80 of the continuous body of the core-side first non-woven fabric S1, and a second absorption layer L2 is formed of the short fiber layer 82 supporting the SAP 80 of the continuous body of the core-side second non-woven fabric S2.

Each of the scatter devices 71 and 72 will be further described. Each of the scatter devices 71 and 72 includes a hopper 73 that stores the SAP 80, a metering portion 74, a guider 75, and a scatter case 76. The metering portion 74 adjusts a scatter amount of the SAP 80 dropping from the hopper 73. The guider 75 guides the SAP 80 guided from the metering portion 74 to the scatter case 76. The scatter case 76 scatters the SAP 80 supplied from the guider 75 to a predetermined region on the front surface of the continuous body of the core-side first non-woven fabric S1 and the continuous body of the core-side second non-woven fabric S2, and prevents the SAP 80 from scattering to a region other than the predetermined region. Specifically, the scatter case 76 includes a case body that is provided with a scatter opening (not illustrated) for dropping the SAP guided by the guider 75 and prevents the SAP 80 dropping from the scatter opening from being scattered around, and a shutter (not illustrated) that is accommodated in the case body and intermittently opens and closes the opening. With the scatter case 76, the SAP 80 is scattered (FIGS. 5A to 7C) to a predetermined region of the short fiber layer 82 of the continuous body of the core-side first non-woven fabric S1 and the continuous body of the core-side second non-woven fabric S2.

A method for forming the first and second low-density regions R11 and R12 and the holding region R2 in the continuous body of the core-side first non-woven fabric S1 illustrated in FIGS. 5A to 7C will be further described.

First, a first method for forming the first low-density region R11, the second low-density region R12, and the holding region R2 will be described. In the first method, the second low-density region R12 and the holding region R2 of the continuous body of the core-side first non-woven fabric S1 are formed as follows. The first applicator 91 applies the adhesive in a state where the amount per unit area of the adhesive applied to the region corresponding to the second low-density region R12 (the second low-density region R12 in FIGS. 6A to 7C) in the continuous body of the core-side first non-woven fabric S1 is adjusted to become smaller than the amount per unit area of the adhesive applied to the region corresponding to the holding region R2. Therefore, the SAP 80 scattered in the region corresponding to the second low-density region R12 becomes smaller than the SAP 80 scattered in the region corresponding to the holding region R2 in terms of the amount supported on the continuous body of the core-side first non-woven fabric S1. For example, the application region of the first applicator 91 can be set such that the adhesive is applied to the region corresponding to the holding region R2 in the continuous body of the core-side first non-woven fabric S1, and the adhesive is not applied to the region corresponding to the second low-density region R12.

On the other hand, the application amount of the adhesive to the continuous body of the core-side second non-woven fabric S2 by the first applicator 91 is adjusted in accordance with the amount of the SAP to be supported in the holding region R3 (FIG. 5B).

In the first method, the first low-density region R11 of the continuous body of the core-side first non-woven fabric S1 is formed by stopping or substantially stopping the supply of the SAP 80 to the region corresponding to the cut region Cut (see FIG. 5A) between the adjacent cores 25 in the continuous body of the core-side first non-woven fabric S1. Specifically, the supply of the SAP 80 to the cut region Cut is stopped or suppressed by closing or substantially closing the scatter opening by the shutter of the scatter case 76. Due to this, the first low-density region R11 is formed in the cut region Cut of the core-side first non-woven fabric S1. In the cut region Cut, the application of the adhesive from the first applicator 91 is stopped or suppressed.

Similarly, the third low-density region R13 is formed in the core-side second non-woven fabric S2 by stopping or suppressing the supply of the SAP 80 and the adhesive to the region corresponding to the cut region Cut between the adjacent cores 25 in the continuous body of the core-side second non-woven fabric S2.

As a second method for forming the first low-density region R11, the second low-density region R12, and the holding region R2, the first low-density region R11, the second low-density region R12, and the holding region R2 as illustrated in FIGS. 5A to 7C can also be formed by the metering portion 74 adjusting the supply amount of the SAP 80 in a direction orthogonal to the conveyance direction of the continuous body of the core-side first non-woven fabric S1. Specifically, the metering portion 74 adjusts the supply amount per unit area of the SAP 80 in the first low-density region R11 and the second low-density region R12 to become smaller than the supply amount per unit area of the SAP 80 in the holding region R2. The scatter case 76 scatters the amount of the SAP 80 adjusted by the metering portion 74 to the continuous body of the core-side first non-woven fabric S1. Due to this, the amount of the SAP 80 supported in the first low-density region R11 and the second low-density region R12 can be made smaller than the amount of the SAP 80 supported in the holding region R2.

In the second method, the first low-density region R11 of the continuous body of the core-side first non-woven fabric S1 can also be formed by closing or substantially closing the scatter opening by the shutter in the first method.

As a third method for forming the first low-density region R11, the second low-density region R12, and the holding region R2, the first low-density region R11, the second low-density region R12, and the holding region R2 as illustrated in FIGS. 5A to 7C can also be formed using a transfer body capable of holding the SAP 80 in a predetermined pattern and transferring the SAP 80 to the continuous body of the core-side first non-woven fabric S1. Specifically, the transfer body has a region corresponding to the holding region R2 holding the SAP 80 at a predetermined distribution density, and a region corresponding to the first low-density region R11 and the second low-density region R12 holding the SAP 80 at a density lower than that in the region corresponding to the holding region R2. The transfer body is provided on an outer surface of a transfer roller. The continuous body of the core-side first non-woven fabric S1 is tucked between the conveyance roller around which the continuous body of the core-side first non-woven fabric S1 is wound and the transfer roller. Due to this, the SAP 80 held by the transfer body of the transfer roller is transferred to the continuous body of the core-side first non-woven fabric S1, and the first low-density region R11, the second low-density region R12, and the holding region R2 are formed.

On the other hand, the continuous body of the core-side second non-woven fabric S2 having the holding region R3 can be formed using a transfer body having a region corresponding to the holding region R3 holding the SAP 80 at a predetermined distribution density.

As yet another method, the holding region R2 (uncut region) and the low-density region R1 (cut region) can be formed by cutting a formation target part of the low-density region R1 (the first low-density region R11 in the examples of FIGS. 5A to 5C, and the first low-density region R11 and the second low-density region R12 in the examples of FIGS. 6A to 7C) in the continuous body of the core-side first non-woven fabric S1 on which the SAP 80 is scattered.

As still another method, the low-density region R1 and the holding region R2 can be formed by scattering the SAP 80 to the entire region that is a formation target of the low-density region R1 (the first low-density region R11 in the examples of FIGS. 5A to 5C, and the first low-density region R11 and the second low-density region R12 in the examples of FIGS. 6A to 7C) and the holding region R2 in the continuous body of the core-side first non-woven fabric S1, and then additionally scattering the SAP 80 only to the region that is a formation target of the holding region R2.

The conveyance of the continuous body of the core-side first non-woven fabric S1 and the continuous body of the core-side second non-woven fabric S2 and the scatter of the SAP 80 thereto are disclosed in, for example, WO 2017/131014, and the entire description thereof is incorporated.

Figure 15D:
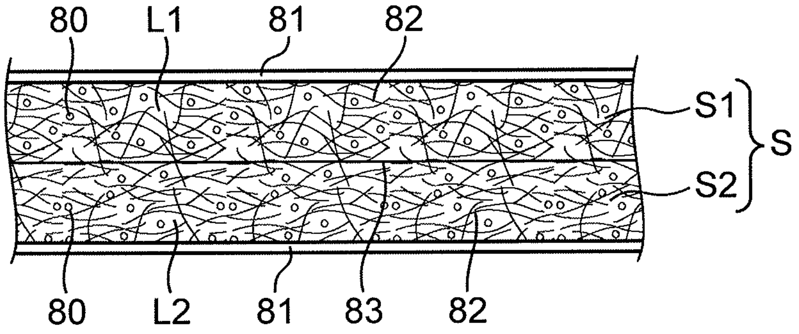
FIG. 15D is a cross-sectional view illustrating a process for producing the core, and illustrates a state where the core-side first non-woven fabric and the core-side second non-woven fabric are laminated to form a laminate.

Next, as illustrated in FIG. 13, after the SAP 80 is scattered, the adhesive is applied from the second applicator 95 onto the front surface of the continuous body of the one core-side second non-woven fabric S2. Due to this, an adhesive layer 83 illustrated in FIG. 15D is formed on the continuous body of the core-side second non-woven fabric S2. The continuous body of the core-side second non-woven fabric S2 on which the adhesive layer 83 is formed is conveyed to the lamination roller R by the second conveyor C2, and the continuous body of the core-side first non-woven fabric S1 is conveyed to the lamination roller R by the first conveyor C1.

As illustrated in FIGS. 13 and 14, the first conveyor C1, the second conveyor C2, and the lamination roller R are configured such that the continuous body of the core-side first non-woven fabric S1 and the continuous body of the core-side second non-woven fabric S2 to be conveyed are disposed in a V shape in side view. The lamination roller R tucks the continuous body of the core-side first non-woven fabric S1 and the continuous body of the core-side second non-woven fabric S2 with the lamination conveyor C3 in a state where the continuous body of the core-side first non-woven fabric S1 and the continuous body of the core-side second non-woven fabric S2 are laminated. At this time, the first absorption layer L1 of the continuous body of the core-side first non-woven fabric S1 conveyed by the first conveyor C1 and the second absorption layer L2 of the continuous body of the core-side second non-woven fabric S2 conveyed by the second conveyor C2 oppose each other. Due to this, as illustrated in FIGS. 14 and 15D, the continuous body of the core-side first non-woven fabric S1 and the continuous body of the core-side second non-woven fabric S2 are laminated and joined in a state with the adhesive layer 83 interposed therebetween in a state where the first absorption layer L1 and the second absorption layer L2 oppose each other. Due to this, one thick laminate S is formed. In the laminate S, the first absorption layer L1 and the second absorption layer L2 oppose each other with the adhesive layer 83 interposed therebetween, and both the layers L1 and L2 are sandwiched between the diffusion layers 81 and 81 of the continuous body of the core-side first non-woven fabric S1 and the continuous body of the core-side second non-woven fabric S2.

As described above, since the core-side first non-woven fabric S1 and the core-side second non-woven fabric S2 are laminated with the first absorption layer L1 and the second absorption layer L2 of the core-side first non-woven fabric S1 and the core-side second non-woven fabric S2 of the two layers opposing each other, the SAP 80 can be suppressed from falling off from the first absorption layer L1 and the second absorption layer L2. In a case where the core 25 formed by laminating the first absorption layer L1 and the second absorption layer L2 to oppose each other in this manner is used in a subsequent step, it is possible to suppress the SAP 80 from falling off from the core 25.

As illustrated in FIG. 13, tissue paper T is supplied onto the lamination conveyor C3. The third applicator 96 (FIG. 13) provided upstream of the lamination conveyor C3 applies the adhesive to the upper surface of the tissue paper T.

Figure 15E:
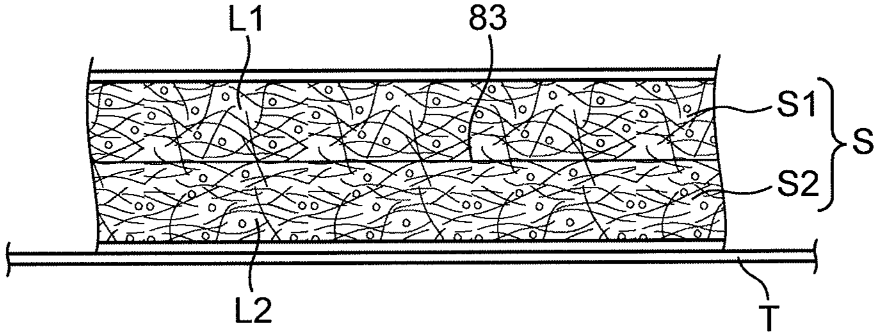
FIG. 15E is a cross-sectional view illustrating a process for producing the core, and illustrates a state where tissue paper is supplied to the laminate.

Then, as illustrated in FIGS. 13 and 14, the lamination conveyor C3 supplies the tissue paper T applied with the adhesive to below the laminate S, and sandwiches the laminate S with the lamination roller R. Due to this, as illustrated in FIG. 15E, the laminate S is joined to the front surface of the tissue paper T. Furthermore, the lamination conveyor C3 conveys downstream a joint body of the laminate S and the tissue paper T.

As illustrated in FIG. 13, the fourth applicator 97, the folder 98, and the pair of pressure welding rollers 99 are provided downstream of the lamination conveyor C3. The lamination conveyor C3 is provided with a negative pressure case 78 that sucks the tissue paper T.

The fourth applicator 97 applies the adhesive to at least one edge portion of both side edge portions in a direction orthogonal to the conveyance direction on the upper surface of the tissue paper T. Note that in the case of the present example, the width of the tissue paper T in the direction orthogonal to the conveyance direction is larger than twice the width of the laminate S.

Figure 15F:
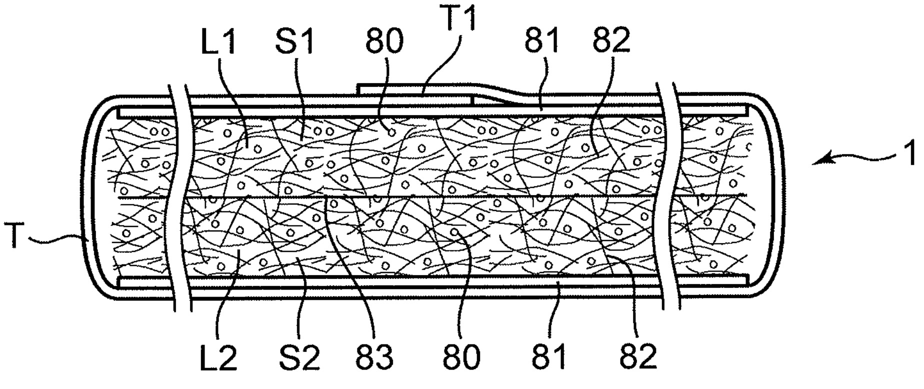
FIG. 15F is a cross-sectional view illustrating a process for producing the core, and illustrates a state where the laminate is wrapped with the tissue paper.

The folder 35 wraps the laminate S with the tissue paper T by folding back, as illustrated in FIG. 15F, side portions extending from the laminate S to both sides in the width direction in the tissue paper T. The pressure welding roller 99 press the laminate S and the tissue paper T in a thickness direction, thereby joining the tissue paper T to the laminate S. Due to this, the continuous body of the core 25 where the plurality of cores 25 are continuous is produced. The continuous body of the core 25 is cut into each core 25 by a cutter (not illustrated).

Note that the continuous body of the core-side first non-woven fabric S1 and the continuous body of the core-side second non-woven fabric S2 may not have the diffusion layer 81. In this case, the step of laminating the diffusion layer 81 can be omitted. The continuous body of the core-side first non-woven fabric S1 and the continuous body of the core-side second non-woven fabric S2 may not be wrapped with the tissue paper T. In this case, the step of laminating the tissue paper T and wrapping the laminate S can be omitted. Furthermore, the core 25 may be produced only from the continuous body of the core-side first non-woven fabric S1, not formed from the laminate S of the continuous body of the core-side first non-woven fabric S1 and the continuous body of the core-side second non-woven fabric S2.

(Step 5)

In step 5, as illustrated in FIG. 10, the back sheet in-process item where a continuous body of the back sheet 26 and a continuous body of the leg gather 31 are joined is formed. Specifically, a continuous body of the liquid impermeable sheet 26*a* and a continuous body of the outer layer sheet 26*b* are conveyed along the MD direction A. An adhesive is applied to at least one of these sheets, and the continuous body of both sheets 26*a* and 26*b* is sandwiched between a pair of nip rolls (reference numeral omitted) illustrated in FIG. 8 in a state of being overlapped, whereby the continuous body of the both sheets 26*a* and 26*b* is joined by adhesion using a hot melt adhesive, welding by heat sealing, ultrasonic welding, or the like. Due to this, the continuous body of the back sheet 26 is formed.

Furthermore, the continuous body of the leg gather 31, which is an elastic member, is joined to both side portions in the CD direction W orthogonal to the MD direction A of the liquid impermeable sheet 26*a* by adhesion using a hot melt adhesive, welding by heat sealing, ultrasonic welding, or the like in an expanded state in the MD direction A. Due to this, the continuous body of the leg gather 31 is provided on the continuous body of the back sheet 26, and the back sheet in-process item is produced.

(Step 6)

In step 6, the absorber in-process item where the front sheet in-process item formed in step 3, the core 25 formed in step 4, and the back sheet in-process item formed in step 5 are combined is formed.

In a nip roll (reference numeral omitted) provided at a converging point of step 4 and step 5, the core 25 produced in step 4 is placed and joined on the liquid impermeable sheet 26*a* of the back sheet in-process item produced in step 5. A plurality of absorber elastic members 21 having a predetermined length is held on a drum surface (outer surface) of a rotary drum P (FIG. 8) provided on a downstream side of the nip roll. In response to the rotation of the rotary drum P, the absorber elastic member 21 is joined in an expanded state in a direction orthogonal to the conveyance direction between the adjacent cores 25 on the back sheet in-process item.

Figure 18F:
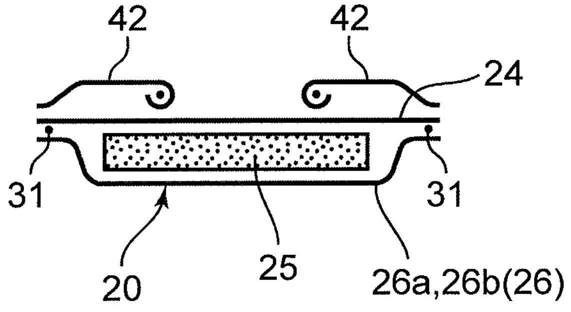
FIG. 18F is a cross-sectional view of a main part in a production process of step 6, and illustrates a state of forming an absorber in-process item where a front sheet in-process item formed in step 3, a core formed in step 4, and a back sheet in-process item formed in step 5 are combined.

The front sheet in-process item is supplied onto the back sheet in-process item so as to tuck the core 25, the continuous body of the leg gather 31, and the absorber elastic member 21, and the front sheet in-process item is joined onto the back sheet in-process item (see FIG. 18F).

The female fastener 22 (FIGS. 1 and 2) is provided over the entire width direction (corresponding to the waist width direction) with respect to the outer surface on the side opposite to the core 25 at the end portion provided with the absorber elastic member 21 in the back sheet in-process item.

Furthermore, the surface facing the skin surface side provided with the core 25 in the back sheet in-process item is provided with the indicator 50 (FIGS. 1 and 2) extending in the conveyance direction (MD direction A) of the back sheet in-process item in the center portion in the CD direction W of the outer layer sheet 26*b*. Due to this, the in-process item of the absorber 20 (absorber in-process item) continuous in the MD direction A is produced.

The step of providing the female fastener 22 is only required to be performed between steps 5 to 12. The step of providing the indicator 50 is only required to be performed between steps 5 to 13.

(Step 7)

In step 7, the absorber in-process item formed in step 6 is cut into individual absorbers 20. Specifically, the absorber in-process item including the absorber 20 and the three-dimensional gather 40 extending in the MD direction A is cut by an interior cutter 64 for constant length in the MD direction A, and the individual absorbers 20 are produced. Thereafter, the orientation of the absorber 20 is reversed by 90 degrees by an interior turn drum 65 so as to be in a posture suitable for an assembly step in a subsequent horizontal flow state. At this time, the absorber elastic member 21 is disposed so as to be positioned at the tip end portion of the absorber 20 on the side opposite to the waist body 16 in the MD direction A (see FIG. 3).

(3) Step 8 to Step 13

Figure 16:
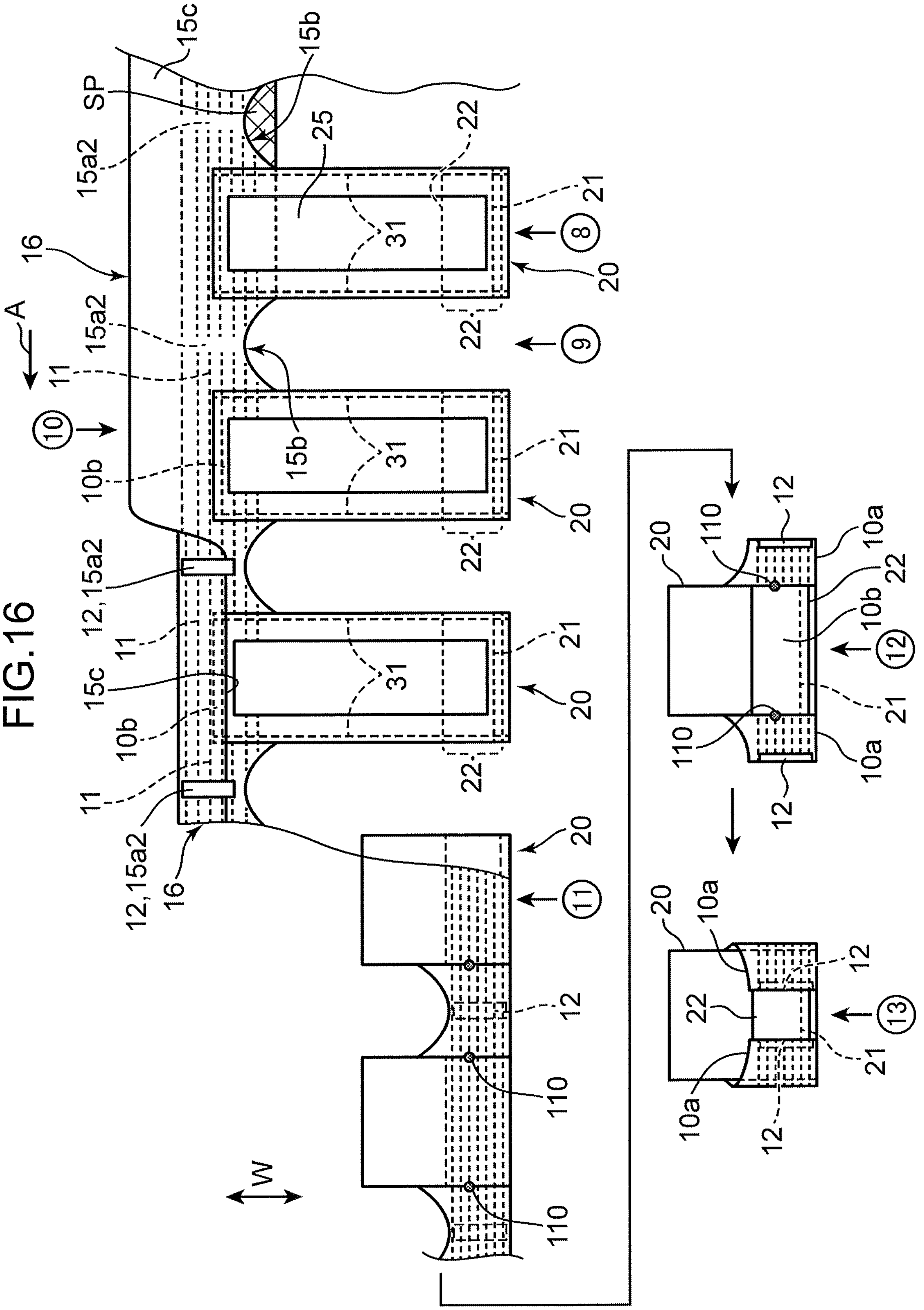
FIG. 16 is a plan view of a production situation of step 8 to step 13.

Steps 8 to 13 are steps for assembling the wearing article 1 in the horizontal flow state illustrated in FIG. 16. In these steps, first, the absorber 20 produced in step 7 is joined to the waist continuous body produced in steps 1 to 2. Next, the absorber 20 is folded in two in the waist orthogonal direction (CD direction W in FIG. 16), and the waist continuous body is cut into the individual waist members 10. Thereafter, the both side portions 10*a* positioned on both sides in the waist width direction (MD direction A in FIG. 16) with respect to the joint portion 10*b* in the waist member 10 are folded in the waist width direction (MD direction A in FIG. 16), and the male fastener 12 and the female fastener 22 are engaged with each other.

In the horizontal flow state of FIG. 16, the MD direction A coincides with the waist width direction, and the CD direction W coincides with the waist orthogonal direction.

(Step 8)

Figure 19A:
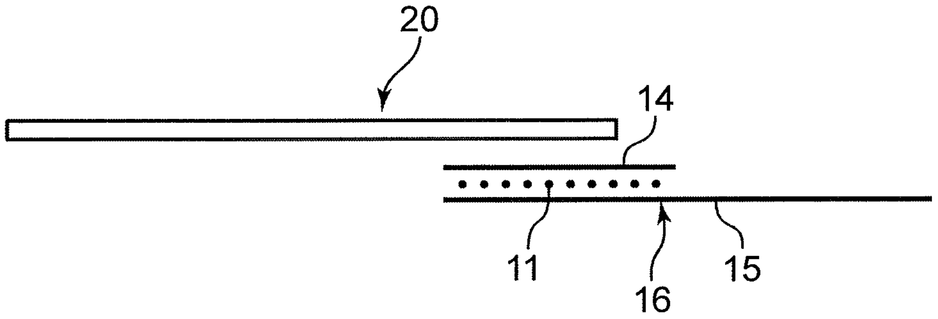
FIG. 19A is a cross-sectional view of a main part in a production process of step 8 and step 9, and illustrates a state where an absorber turned in a predetermined direction through step 7 is joined to a waist continuous body.

In step 8, in FIGS. 8, 16, and 19, one end portion (end portion opposite to the female fastener 22) of the absorber 20 reversed by 90 degrees is disposed on the joint portion 10*b* of each of the waist bodies 16 in the waist continuous body produced in step 2 (see FIG. 19A). The absorber 20 is joined to the joint portion 10*b* on the surface facing the skin surface side of the inner sheet 14 of each of the waist bodies 16. The joint means is not limited to adhesion by a hot melt adhesive, and welding by heat sealing or ultrasonic welding can also be used.

In the present embodiment, in steps 1 to 2, the waist continuous body where the waist bodies 16 of the plurality of wearing articles 1 are continuous in the waist width direction (MD direction A in FIGS. 9 and 16) is produced. That is, in the waist continuous body, the both end portions 10*c* of the waist bodies 16 are continuous so that the waist bodies 16 of the plurality of wearing articles 1 are continuous in the waist width direction. The absorber 20 of each of the wearing articles 1 extending in the waist orthogonal direction (CD direction W in FIGS. 9 and 16) is joined to the joint portion 10*b* of the part corresponding to each of the waist bodies 16 in the waist continuous body.

(Step 9)

In step 9, the waist continuous body (the continuous body of the plurality of waist bodies 16) is cut by an elliptical die cutter 66 so as to provide a leg hole SP in FIG. 16. Due to this, the leg round curve portion 15*b* is formed.

Step 8 and step 9 can be interchanged. That is, first, a part between the joint portions 10*b* in the waist continuous body is cut by the die cutter 66 so as to provide the leg hole SP. Thereafter, one end portion of the absorber 20 reversed by 90 degrees is disposed on the joint portion 10*b* of each of the waist bodies 16 in the waist continuous body.

(Step 10)

Figure 19B:
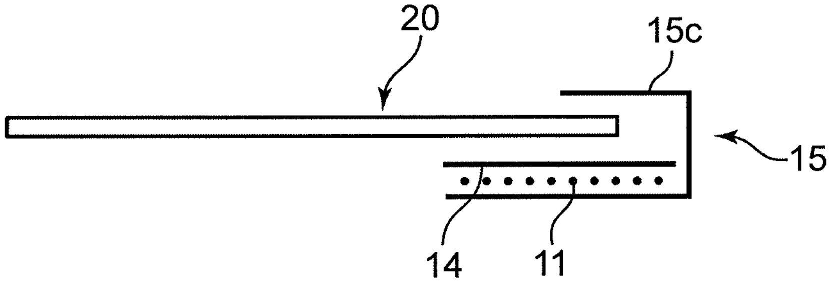
FIG. 19B is a cross-sectional view of a main part in a production process of step 10, and illustrates a state where an extending portion is folded back.
Figure 19C:
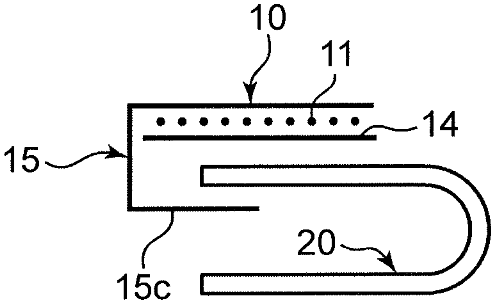
FIG. 19C is a cross-sectional view of a main part in a production process of step 11 to step 13, and illustrates a state where the wearing article is folded in two.

In step 10, the extending portion 15*c* of the waist continuous body is folded back so as to cover a part of the waist elastic member 11, and the male fastener 12 is joined (see FIG. 19B). Specifically, the extending portion 15*c* is joined to each absorber 20 in a state of covering the end portion joined to the waist continuous body of each absorber 20. The joint means is not limited to adhesion by a hot melt adhesive, and welding by heat sealing or ultrasonic welding can also be used.

The male fastener 12 is joined to the weakened portion 15*a*2 on the surface of the skin surface side of the waist continuous body. The weakened portion 15*a*2 is provided over a range from the folded part of the extending portion 15*c* to a position below the folded part. The joint means is not limited to adhesion by a hot melt adhesive, and welding by heat sealing or ultrasonic welding can also be used. The weakened portion 15*a*2 is positioned in the middle between the absorbers 20 adjacent in the MD direction A in the waist continuous body. The male fastener 12 is joined to this middle position.

(Step 11)

In step 11, the absorber 20 is folded in two in the CD direction W. Specifically, the waist continuous body and the absorber 20 are conveyed in the MD direction A in a state where tension is applied to the waist continuous body while a suction device (not illustrated) holds a free end in the CD direction W of the absorber 20, that is, a tip end portion opposite to an end portion joined to the waist continuous body in the CD direction W. In a two-folding device 67, a plurality of pairs of rollers sandwiching the waist continuous body between the front and back sides are disposed so that the waist continuous body is inverted toward the free end of the absorber 20. As a result, the absorber 20 is folded in two with the middle position in the CD direction W as a boundary (see FIG. 19C).

Note that the absorber 20 may be folded in two such that the waist continuous body moves on the absorber 20 side in a state where the tip end portion of at least one absorber 20 is held by the suction device and pressed by a pressing device.

By this step 11, each absorber 20 is folded in the CD direction W such that the surface facing the skin surface side of each absorber 20 opposes the surface facing the skin surface side at a position corresponding to the joint portion 10*b* of each of the waist bodies 16 of the waist continuous body. It is desirable that the end portion of the absorber 20 on the side opposite to the end portion joined to each of the waist members 10 and at least one of the absorber 20 and each of the waist members 10 overlapping the end portion are detachably temporarily fixed (temporary fix 110 in FIG. 16) so as to maintain the state of being folded in two. As a temporary fixing means, adhesion by a hot melt adhesive, welding by heat sealing, ultrasonic welding, or the like may be used, or temporary fixing may be performed by mechanical engagement such as pin embossing.

The temporary fixing position is preferably outside the core 25 in the waist width direction from the viewpoint of reducing the influence on the core 25. Furthermore, as a temporary fixing position, in the vicinity of both end portions of each absorber 20, the three-dimensional gather 40 extending in the waist orthogonal direction is preferably temporarily fixed at a position outside in the waist width direction. In this case, rising of the three-dimensional gather 40 at the time of wearing is not inhibited by the temporary fix 110, and as a result, the three-dimensional gather 40 reliably functions as a weir for the body fluid.

The position of the temporary fix 110 is preferably disposed between the plurality of waist elastic members 11 in the waist orthogonal direction. In this manner, a decrease in elastic force due to cutting or the like of the waist elastic member 11 is suppressed.

The position of the temporary fix 110 is most preferably within the region of weakened portion **15*a*1. This is because the final shape of the wearing article 1 in which the male fastener 12 and the female fastener 22 are engaged can be held by suppressing the movement of the position of the temporary fix 110 by the elasticity of the waist elastic member 11**.

Here, when it is difficult to form the temporary fix 110 within the region of the weakened portion **15*a*1, it is conceivable to form a surplus part in the weakened portion 15*a*1 by relatively increasing the weakened portion 15*a*1 with respect to the core 25, and form the temporary fix 110 in this surplus part. As a method for forming the surplus part, for example, at least one of reducing the size of the core 25 while maintaining the size of the weakened portion 15*a*1 and increasing the size of the weakened portion 15*a*1 while maintaining the size of the core 25 can be adopted. When the core 25 is made small, the final shape of the wearing article 1 can be maintained as described above, but the absorption performance of the wearing article 1 decreases. When the weakened portion 15*a*1 is increased, the final shape of the wearing article 1 can be held as described above, but the elastic force of the waist member 10** decreases.

On the other hand, as another method, when it is difficult to form the temporary fix 110 within the region of the weakened portion **15*a*1, it is conceivable to perform temporary fixing outside the weakened portion 15*a*1 although the holding ability of the final shape of the wearing article 1** decreases.

Whether or not to form the temporary fix 110 in the region of the weakened portion **15*a*1 is determined in consideration of the balance among the degree of holding of the final shape of the wearing article 1, the absorption performance, and the degree of the elastic force of the waist member 10**.

In the present embodiment, temporary fixing is performed outside the weakened portion **15*a*1** in consideration of these.

By performing such temporary fixing, the absorber 20 can be maintained in a state of being folded in two in the CD direction W until the cutting step in step 12 and the engaging step in step 13 described later. Due to this, when the waist continuous body is cut in step 12 after the absorber 20 is temporarily fixed, the two-folded state of the absorber 20 can be maintained before and after the cutting.

The temporary fixing is performed with an adhesive force to an extent that it can be easily pulled off when the wearing article is worn. Note that in step 11, the absorber 20 is folded in two so that the female fastener 22 is exposed on the outer surface opposite to the surface facing the skin surface side of each absorber 20.

By this step 11, the absorber 20 is folded in two such that the waist continuous body overlaps the tip end portion of the absorber 20 in a state where the tip end portion of the absorber 20 is held. Therefore, the plurality of wearing articles 1 can be continuously folded in the waist orthogonal direction. Therefore, each wearing article 1 can be folded in the waist orthogonal direction at a high speed as compared with the case where each wearing article 1 is folded separately. Since the absorber 20 is folded in a state where the tip end portion opposite to the joint portion **10*b* joined to the waist continuous body of the absorber 20 is held, it is possible to fold the absorber 20 in two in the waist orthogonal direction so that the waist continuous body and the tip end portion of the absorber 20 overlap each other while suppressing the movement of the absorber 20. It is possible to produce the wearing article 1 folded by folding back as they are the both end portions of each of the waist bodies 16** cut from the waist continuous body.

(Step 12)

In step 12, the waist continuous body is cut in the CD direction W by a cutter 68 at a middle position between the adjacent absorbers 20 and a middle position in the MD direction A of the male fastener 12. Due to this, the waist continuous body and the plurality of absorbers 20 are separated into each of the waist bodies 16 and each absorber 20 joined thereto. The male fastener 12 is divided into two in the MD direction A along the CD direction W between the adjacent absorbers 20, and is left at the both end portions **10*c* of each of the adjacent waist bodies 16. In this state, each of the waist bodies 16 is in a state of being developed in the MD direction A. The male fastener 12 is not limited to a case of being divided into two by the cut, and the male fasteners 12 divided in advance may be disposed at intervals at the both end portions 10*c* of the adjacent waist body 16**.

(Step 13)

In step 13, the both side portions **10*a* in the MD direction A of the waist member 10 are folded back toward the joint portion 10*b* of the waist member 10 such that both male fasteners 12 at the both end portions 10*c* oppose the outer surface of the absorber 20. Next, the male fasteners 12 of the waist member 10 and the female fastener 22 of the absorber 20** are engaged.

The method for producing the refastenable type wearing article 1 described above is a method for producing a wearing article including: the waist member 10 disposed around the waist of a wearer, and the absorber 20 joined to the joint portion **10*b* in the waist width direction of the waist member 10 and extending in the waist orthogonal direction orthogonal to the waist width direction from the joint portion 10*b* so as to be disposed from a back portion to a front abdomen portion of the wearer via a crotch portion, and the method includes the following steps of the step of producing the waist member 10, the step of producing the absorber 20, the step of joining the absorber 20 to the joint portion 10*b* of the waist body 16, and the step of engaging the male fastener 12 and the female fastener 22** with each other.

(Step of Producing Waist Member 10)

The step of producing the waist member 10 includes steps 1 to 2 for producing the waist continuous body, a step (part of step 10) for joining the male fastener 12 to each of the waist bodies 16 constituting the waist continuous body, and step 12 of cutting the waist continuous body.

(Step of Producing Absorber 20)

The step of producing the absorber 20 includes step 3 for producing the front sheet in-process item, step 4 for producing the core 25, step 5 for producing the back sheet in-process item, step 6 for producing the absorber in-process item, and step 7 for cutting the absorber in-process item into individual absorbers 20.

(Step of Joining Absorber 20 to Joint Portion 10*b* of Waist Body 16)

Step 8 corresponds to the step of joining the absorber 20 to the joint portion 10*b* of the waist body 16.

(Step of Engaging Male Fastener 12 and Female Fastener 22 with Each Other)

Step 13 corresponds to the step of engaging the male fastener 12 and the female fastener 22 with each other.

Note that the present invention is not limited to the above embodiment, and for example, the following aspect can also be adopted.

In the refastenable type wearing article 1, the joint portion 10*b* of the waist member 10 is disposed at the back portion. The absorber 20 extends from the joint portion 10*b* disposed in the back portion to the front abdomen portion via the crotch portion, and the tip end portion is disposed in the front abdomen portion. Then, the both side portions 10*a* of the waist member 10 are expanded from the back portion to the front abdomen portion, and are engaged with the tip end portion of the absorber 20. However, the joint portion 10*b* of the waist member 10 may be disposed in the front abdomen portion. The absorber 20 may extend from the joint portion 10*b* disposed in the front abdomen portion to the back portion via the crotch portion, and the tip end portion may be disposed in the back portion. The both side portions 10*a* of the waist member 10 may be expanded from the front abdomen portion to the back portion, and engaged with the tip end portion of the absorber 20.

In the refastenable type wearing article 1, the female fastener 22 is provided on the outer surface of the back sheet 26 of the absorber 20. However, the female fastener 22 may be omitted, and the outer surface of the back sheet 26 may be treated so as to be engageable with the male fastener 12. The back sheet 26 having a property capable of engaging with the male fastener 12 can also be adopted. Furthermore, the male fastener 12 may be provided on the outer surface of the back sheet 26 of the absorber 20, and the surface on the skin surface side of the waist member 10 may be configured to be engageable with the male fastener 12.

Note that the above-described specific embodiment mainly includes the invention having the following configuration.

A method for producing a wearing article for solving the above problems is a method for producing a wearing article including a waist member disposed around a waist of a wearer, and an absorber joined to the waist member and extending in an orthogonal direction with respect to a width direction from a joint portion with the waist member so as to be disposed from a back portion to a front abdomen portion of the wearer via a crotch portion, the method including: a step of producing the waist member including a waist body that extends in the width direction, has elasticity capable of expanding and contracting in the width direction, and is disposed around the waist of the wearer, and first engagement portions provided on a surface facing a skin surface side of the wearer at both end portions of the waist body in the width direction; a step of producing the absorber including a core for absorbing a body fluid, a front sheet provided on the skin surface side of the wearer of the core, a back sheet provided on an outer surface side opposite to the skin surface side of the core so as to sandwich the core between the back sheet and the front sheet, and a second engagement portion provided on an outer surface opposite to a surface facing the skin surface side of the back sheet and detachable with respect to each of the first engagement portions; a step of joining the absorber to the joint portion of the waist body so as to extend in the orthogonal direction from the waist body; and a step of engaging the first engagement portion and the second engagement portion with each other by folding the absorber in two in the orthogonal direction, then folding, in the width direction, both side portions positioned on both sides in the width direction with respect to the joint portion in the waist member, in which the step of producing the absorber includes a step of producing the core by holding a water absorbent polymer on a core-side first non-woven fabric so as to form a holding region and a first low-density region that holds the water absorbent polymer having a lower density than the water absorbent polymer in the holding region and is adjacent in the orthogonal direction to both end portions of the holding region in the orthogonal direction.

According to the above production method, it is possible to produce a wearing article capable of improving the wearing feeling. Specifically, according to the wearing article, the core-side first non-woven fabric holds a water absorbent polymer. Since the absorption performance per unit volume of the water absorbent polymer is higher than the absorption performance per unit volume of fluff pulp, the amount of fluff pulp used when fluff pulp is used can be reduced. Therefore, the thickness of the core can be made thinner than that of a non-woven fabric formed of only fluff pulp having an amount necessary for a predetermined absorption performance. Since the thickness of the wearing article including this core-side first non-woven fabric is also thin, the wearing article can be easily fitted to the body shape of the waist of the wearer, and the fitting feeling of the wearing article can be improved.

Since the distribution density of the water absorbent polymer is higher in the holding region than in the first low-density region, flexibility is poor. On the other hand, since the distribution density of the water absorbent polymer is lower in the first low-density region than in the holding region, the first low-density region has higher flexibility than the holding region. Therefore, the shape of the core having the first low-density region is easily deformed. Here, when the wearer wears the wearing article, the both end portions in the orthogonal direction of the holding region are disposed to face the front abdomen portion and the back portion of the wearer, respectively. The first low-density region where the distribution density of the water absorbent polymer is lower than that in the holding region is disposed in a part adjacent in the orthogonal direction to both end portions in the orthogonal direction of the holding region. Therefore, the part of the core where the first low-density region is disposed is flexibly deformed along the body shape of the front abdomen portion and the back portion, and the part abuts on the front abdomen portion and the back portion with a soft tactile sense, whereby the wearing feeling of the wearing article can be improved.

Since the second engagement portion is engaged with the first engagement portion in the initial state, the wearing article has an underpants-shaped form, and the wearer can wear the wearing article as underpants. By releasing the engagement between the first engagement portion and the second engagement portion, it is possible to develop into a predetermined mode. In the development form, both side portions of the waist member protrude with respect to the absorber disposed at the joint portion of the waist member. The both side portions can be directed to the tip end portion of the absorber along the waist of the wearer, and can be caused to abut on the back sheet of the absorber disposed along the crotch portion of the wearer. Then, the first engagement portions in the both end portions in the width direction of the waist member are engaged with the second engagement portion of the back sheet to support the wearing article around the waist, whereby the absorber is pulled up and the absorber is brought into close contact with the crotch portion of the wearer.

In the method for producing the wearing article, it is preferable that in the step of producing the core, the water absorbent polymer is held on the core-side first non-woven fabric so as to form a second low-density region that holds the water absorbent polymer having a lower density than the water absorbent polymer in the holding region and is sandwiched in the width direction by the holding region.

According to the above production method, the core of the absorber having the second low-density region in which the distribution density of the water absorbent polymer is lower than that in the holding region is formed. The second low-density region has a higher flexibility than the holding region because the distribution density of the water absorbent polymer is low whereas the holding region has poor flexibility because the distribution density of the water absorbent polymer is high. Therefore, the shape of the core having the second low-density region is easily deformed. Specifically, the second low-density region is formed so as to be sandwiched in the width direction by the holding region. Therefore, by bending the core based on the second low-density region, the absorber is easily deformed along the body shape, and the fitting feeling can be improved.

Urine and the like can be diffused in the orthogonal direction along the second low-density region in which an absorption amount of the urine and the like is small, and the urine and the like can be effectively absorbed using the holding region. Furthermore, since the second low-density region can be used as a region for expansion of the water absorbent polymer in the holding region, excessively close contact of the absorber to the skin surface can be suppressed. Hence, it is possible to more quickly eliminate the sticky feeling on the skin surface due to urine and the like and to mitigate the discomfort.

In a state where the first engagement portion and the second engagement portion are engaged with each other to support the wearing article around the waist, and the absorber is brought into close contact with the crotch portion, before absorption of the body fluid, the feeling of close contact with the crotch portion can be improved by the second low-density region of the core. Furthermore, even after absorption of the body fluid, since the expansion space of the absorbent polymer can be secured by the second low-density region of the core, the core can be suppressed from expanding more than necessary on the skin surface side, and the good texture can be maintained.

In the method for producing the wearing article, it is preferable that in the step of producing the core, the second low-density region is formed such that the second low-density region extends in the orthogonal direction.

According to the above production method, it is possible to produce a wearing article having a core in which the second low-density region extending in the orthogonal direction is formed. In the wearing article, by bending the core based on the second low-density region extending in the orthogonal direction, it is possible to deform the absorber along the body shape of the wearer over the formation range of the second low-density region in the orthogonal direction, and to further improve the fitting feeling of the wearing article.

In the method for producing the wearing article, it is preferable that the step of producing the absorber includes a step of producing the front sheet by forming an irregularity shape on a front-side first non-woven fabric and joining a front-side second non-woven fabric to an outer surface opposite to a surface facing the skin surface side in the front-side first non-woven fabric in a state of maintaining the irregularity shape.

According to the wearing article produced by the above production method, the front-side first non-woven fabric of the front sheet is provided with an irregularity shape. Therefore, since the convex part of the irregularity shape is elastically brought into point contact with the skin surface of the wearer, air can pass through the concave part, and the breathability is good, it is possible to improve the texture as compared with the case where the front sheet and the skin surface are in surface contact with each other. The front-side first non-woven fabric having the irregularity shape is joined to the front-side second non-woven fabric so that the irregularity shape is maintained. Therefore, for example, even when the wearer presses the irregularity shape by contact, the convex part is hardly deformed, and the good texture due to point contact with the convex part can be maintained.

In a state where the first engagement portion and the second engagement portion are engaged with each other to support the wearing article around the waist, and the absorber is in close contact with the crotch portion, the breathability and texture can be improved by the irregularity shape of the front sheet before a body fluid is absorbed. Furthermore, even after absorption of the body fluid, the good breathability and texture can be maintained by the irregularity shape of the front sheet.

When the front-side first non-woven fabric of the front sheet has an irregularity shape, and the second low-density region is sandwiched in the width direction by the holding region in the core, the following effects are obtained. In a state where the first engagement portion and the second engagement portion are engaged with each other to support the wearing article around the waist, and the absorber is brought into close contact with the crotch portion, before absorption of the body fluid, the breathability and the texture can be improved while improving the feeling of close contact with the crotch portion by the irregularity shape of the front sheet and the second low-density region of the core. Furthermore, even after absorption of the body fluid, since the expansion space of the absorbent polymer can be secured by the second low-density region of the core, the core can be suppressed from expanding more than necessary on the skin surface side, and the good breathability and texture can be maintained by the irregularity shape of the front sheet.

In the method for producing the wearing article, it is preferable that in the step of producing the front sheet, the front-side first non-woven fabric and the front-side second non-woven fabric are overlapped to simultaneously form the irregularity shape, and the front-side second non-woven fabric is joined to the front-side first non-woven fabric in a state where tension is applied to the front-side second non-woven fabric so that undulation of the front-side second non-woven fabric becomes gentle.

According to the above production method, the irregularity shape is simultaneously formed on two non-woven fabrics in a state where the front-side first non-woven fabric and the front-side second non-woven fabric to be joined to each other are overlapped. Then, the front-side second non-woven fabric is joined to the front-side first non-woven fabric while maintaining the irregularity shape of the front-side first non-woven fabric in a state where tension is applied to the front-side second non-woven fabric so that the undulation of the front-side second non-woven fabric becomes gentle, of the two non-woven fabrics provided with the irregularity shape. Therefore, the step and the production device can be simplified as compared with the case where the step of forming the irregularity shape on the front-side first non-woven fabric and the step of forming the front-side second non-woven fabric having a gentle undulation are separately performed, and the step of overlapping the front-side first non-woven fabric and the front-side second non-woven fabric having been subjected to these steps is further performed. That is, according to the above production method, for example, different undulation shapes can be formed on the same line for the front-side first non-woven fabric and the front-side second non-woven fabric, the number of lines can be reduced as compared with a case where a line for producing the front-side first non-woven fabric and a line for producing the front-side second non-woven fabric are separately provided, and a configuration in which the separate lines are converged can be omitted.

In the method for producing the wearing article, it is preferable that in the step of producing the core, the core-side first non-woven fabric is raised, and the water absorbent polymer is scattered so that the water absorbent polymer enters a gap in fiber layers formed by the raising.

According to the above production method, the core-side first non-woven fabric is raised to form, in the core-side first non-woven fabric, a fiber layer having a gap, and the water absorbent polymer is scattered on the fiber layer. Therefore, a large amount of water absorbent polymer can be supported in the gap between the fiber layers of the core-side first non-woven fabric.

In the method for producing the wearing article, it is preferable that the step of producing the core further includes a step of raising a core-side second non-woven fabric and scattering the water absorbent polymer so that the water absorbent polymer enters a gap in fiber layers formed by the raising, and a step of laminating the core-side first non-woven fabric and the core-side second non-woven fabric such that a fiber layer of the core-side first non-woven fabric and a fiber layer of the core-side second non-woven fabric oppose each other.

According to the above production method, the water absorbent polymer is scattered onto the fiber layers of the two-layer core-side first non-woven fabric and core-side second non-woven fabric, and the fiber layers are laminated to oppose each other, whereby it is possible to produce a wearing article capable of suppressing falling of the water absorbent polymer from the fiber layers. When the core formed by laminating the fiber layers to oppose each other is used in a subsequent step, falling of the water absorbent polymer from the core can be suppressed.

In the method for producing the wearing article, it is preferable that the step of producing the absorber further includes a step of providing an absorber elastic member so as to be capable of expanding and contracting in the width direction at a tip end portion on a side opposite to an end portion joined to the waist body of the absorber in the orthogonal direction.

According to the above production method, it is possible to produce a wearing article having the absorber elastic member at the tip end portion on the side opposite to the end portion joined to the waist body of the absorber in the orthogonal direction. In the absorber of the wearing article, the tip end portion on the side opposite to the end portion joined to the waist body is capable of expanding and contracting in the width direction by the absorber elastic member. The waist body is also capable of expanding and contracting in the width direction. Due to this, since both the waist body and the absorber become capable of expanding and contracting in the width direction in accordance with the waist length of the wearer, the degree of freedom in selection of the engagement position between the first engagement portion provided in the waist body and the second engagement portion of the absorber is large. Therefore, the fitting feeling of the wearing article can be improved.

In the method for producing the wearing article, it is preferable that the step of producing the absorber further includes a step of providing the second engagement portion over substantially an entirety of the width direction of a tip end portion of the back sheet on an outer surface of the tip end portion on a side opposite to the waist member of the back sheet in the orthogonal direction.

According to the above production method, it is possible to produce a wearing article having the second engagement portion over the entire width direction of the tip end portion on the outer surface of the tip end portion of the back sheet. Therefore, by expanding and contracting the waist member in the width direction, the first engagement portion can be engaged with an arbitrary position in the width direction of the second engagement portion, and the degree of freedom in selection of the engagement position is large. Therefore, the engagement position between the waist member and the absorber can be easily adjusted in accordance with the length of the waist of each wearer, and the fitting feeling can be improved.

In the method for producing the wearing article, it is preferable that the step of producing the waist member includes a step of joining a waist elastic member to at least one of an inner sheet and an outer sheet so as to be capable of expanding and contracting along the width direction in a state of being sandwiched between the inner sheet extending in the width direction and the outer sheet extending in the width direction and covering an outer surface opposite to a surface facing the skin surface side of the inner sheet, and a step of performing a weakening treatment on the joint portion such that an elastic force of a core arrangement portion in which the core is arranged among joint portions of the waist body to which the absorber is joined becomes weaker than an elastic force of a part adjacent in the width direction to the core arrangement portion.

According to the above production method, it is possible to produce a wearing article in which the elastic force of the core arrangement portion of the waist body in which the core is arranged is weaker than the elastic force of the part adjacent in the width direction to the core arrangement portion. By joining the core to the core arrangement portion of the waist body of the wearing article, contraction of the core can be suppressed. Therefore, the back portion and the like can be reliably covered with the core. Since the part adjacent to the core arrangement portion expands and contracts, the degree of freedom in selection of the engagement position between the second engagement portion of the tip end portion of the absorber disposed along the crotch portion of the wearer and the first engagement portion provided in the waist body can be improved.

In the method for producing the wearing article, it is preferable that the step of producing the waist member further includes a step of disposing the inner sheet on the outer sheet so as to form an extending portion that protrudes in a direction away from the inner sheet beyond an edge portion of the inner sheet in the orthogonal direction, and a step of covering an end portion in the orthogonal direction of the absorber by folding back the extending portion in the orthogonal direction.

According to the above production method, it is possible to produce a wearing article having improved wearing feeling and good appearance. Specifically, in a wearing article produced by the above production method, the extending portion formed on the outer sheet is folded back so as to protrude in a direction away from the inner sheet beyond the edge portion of the inner sheet, whereby the end portion to be joined to the waist member of the absorber is covered with the extending portion of the outer sheet. Therefore, discomfort caused by contact of the end portion of the absorber with the skin can be suppressed. The end portion of the absorber is not exposed, and the good appearance can be improved.

In the method for producing the wearing article, it is preferable that the step of producing the waist member further includes a step of performing a weakening treatment on a part where the first engagement portion is disposed such that an elastic force of a part where the first engagement portion is disposed in the waist body becomes weaker than an elastic force of a part adjacent in the width direction to the part.

According to the above production method, by weakening the elastic force in the part where the first engagement portion of the waist body is disposed, contraction of the first engagement portion provided thereafter can be suppressed. Therefore, it is possible to suppress the engagement force between the first engagement portion and the second engagement portion from being impaired.

In the method for producing the wearing article, it is preferable that in the step of producing the waist member, a waist continuous body in which each waist body of a plurality of wearing articles is continuous in the width direction is prepared, and the waist continuous body is cut for each region corresponding to each waist body to produce the waist body, in the step of joining the absorber to the joint portion of the waist body, the absorber is joined so as to extend from the joint portion in the orthogonal direction with respect to the joint portion in a region corresponding to each waist body in the waist continuous body, and the step of engaging the first engagement portion and the second engagement portion with each other includes a step of folding the absorber in two in the orthogonal direction so that the waist continuous body overlaps a tip end portion of the absorber in a state of holding a tip end portion on a side opposite to an end portion joined to the waist continuous body in the orthogonal direction of an absorber joined to the waist continuous body at a stage before the waist continuous body is cut into the waist body, and a step of folding back both side portions of the waist body such that both end portions in the width direction of the waist body overlap with the tip end portion of the absorber at a stage after the waist continuous body is cut into the waist body.

According to the above production method, the absorber is joined to each region corresponding to each waist body in the waist continuous body in which the waist body is continuous in the width direction. Then, in a state where the tip end portion of the absorber is held, the absorber is folded in two so that the waist continuous body overlaps the tip end portion of the absorber. Therefore, the plurality of wearing articles can be continuously folded in the orthogonal direction. Therefore, each wearing article can be folded in the orthogonal direction at high speed as compared with a case where each wearing article is folded separately. Since the absorber is folded in a state where the tip end portion opposite to the end portion joined to the waist continuous body of the absorber is held, it is possible to fold the absorber in two in the orthogonal direction so that the waist continuous body and the tip end portion of the absorber overlap each other while suppressing movement of the absorber. It is possible to produce the wearing article folded by folding back as they are the both side portions of each of the waist bodies cut from the waist continuous body.

In the method for producing the wearing article, it is preferable that the step of engaging the first engagement portion and the second engagement portion with each other includes a step of forming a temporary fixing so that an end portion on a side opposite to an end portion joined to the waist member of the absorber and at least one of the absorber and the waist member overlapping the end portion is detachable at a stage after the absorber is folded in two in the orthogonal direction.

According to the above production method, the temporary fixing is formed so that the end portion on the side opposite to the end portion joined to the waist member of the absorber and at least one of the absorber and the waist member overlapping the end portion can be detached, whereby the absorber can be maintained in a state of being folded in two. In a case of adopting a step of cutting the waist continuous body in which the waist body is continuous in the width direction to form the waist member after the temporary fixing is formed, the waist continuous body can be cut while maintaining the two-folded state of the absorber before and after the cutting.

In the method for producing the wearing article, it is preferable that in the step of temporarily fixing, temporary fixing is formed outside relative to the core in the width direction.

According to the above production method, since process by temporary fixing is not performed on the core, deterioration in absorption performance of the core can be suppressed.

The invention claimed is:

1. A method for producing a wearing article including a waist member configured to be disposed around a waist of a wearer, and an absorber joined to the waist member and extending in an orthogonal direction with respect to a width direction of the waist member from a joint portion with the waist member so as to be disposed from a back portion to a front abdomen portion of the wearer via a crotch portion, the method comprising:

producing the waist member including a waist body that extends in the width direction, has elasticity capable of expanding and contracting in the width direction, and is configured to be disposed around the waist of the wearer, and first engagement portions provided on a surface facing a skin surface of the wearer at both end portions of the waist body in the width direction;

producing the absorber including a core for absorbing a body fluid, and a second engagement portion;

joining the absorber to the joint portion of the waist body in a form of extending in the orthogonal direction from the waist body; and engaging the first engagement portions and the second engagement portion with each other by folding the absorber in two in the orthogonal direction, then folding, in the width direction, both side portions positioned on both sides in the width direction with respect to the joint portion in the waist member, wherein the producing of the absorber includes:

producing the core by scattering water absorbent polymer over a core-side first non-woven fabric of the core so as to form a holding region, and so as to form first low-density regions on first and second end portions in the orthogonal direction of the holding region, respectively, wherein each first low-density region includes the water absorbent polymer, and a distribution density of the water absorbent polymer in each first low-density region is lower than that of the holding region, wherein one of the first and second end portions in the orthogonal direction of the holding region is disposed to face the front abdomen portion, and the other of the first and second end portions in the orthogonal direction of the holding region being disposed to face the back portion when the wearing article is worn by the wearer;

providing a front sheet and a back sheet on opposite surfaces of the core, respectively, so as to sandwich the core between the front sheet and the back sheet, wherein the front sheet is arranged on a surface of the core which faces the skin surface of the wearer when the wearing article is worn by the wearer; and providing the second engagement portion on an outer surface of the back sheet to detachably engage the absorber to the first engagement portions, wherein the outer surface of the back sheet faces away from the skin surface of the wearer when the wearing article is worn by the wearer, wherein the engaging of the first engagement portions and the second engagement portion with each other includes forming a temporary fixing so that an end portion on a side opposite to an end portion joined to the waist member of the absorber and at least one of the absorber and the waist member overlapping the end portion is detachable at a stage after the absorber is folded in two in the orthogonal direction, and in the forming of the temporary fixing, the temporary fixing is formed outside relative to the core in the width direction.

2. The method for producing a wearing article according to claim 1, wherein in the producing of the core, the water absorbent polymer is held on the core-side first non-woven fabric so as to form a second low-density region that holds the water absorbent polymer having a lower density than the water absorbent polymer in the holding region and is sandwiched in the width direction by the holding region.

3. The method for producing a wearing article according to claim 2, wherein in the producing of the core, the second low-density region is formed such that the second low-density region extends in the orthogonal direction.

4. The method for producing a wearing article according to claim 1, wherein the producing of the absorber includes producing the front sheet by forming an irregularity shape on a front-side first non-woven fabric, and joining a front-side second non-woven fabric to an outer surface of the front-side first non-woven fabric in a state of maintaining the irregularity shape, wherein the outer surface of the front-side first non-woven fabric faces away from the skin surface of the wearer when the wearing article is worn by the wearer.

5. The method for producing a wearing article according to claim 4, wherein in the producing of the front sheet, the front-side first non-woven fabric and the front-side second non-woven fabric are overlapped to simultaneously form the irregularity shape, and the front-side second non-woven fabric is joined to the front-side first non-woven fabric in a state where tension is applied to the front-side second non-woven fabric so that undulation of the front-side second non-woven fabric becomes gentle.

6. The method for producing a wearing article according to claim 1, wherein in the producing of the core, the core-side first non-woven fabric is raised, and the water absorbent polymer is scattered so that the water absorbent polymer enters a gap in fiber layers formed by the raising.

7. The method for producing a wearing article according to claim 6, wherein the producing of the core further includes raising a core-side second non-woven fabric and scattering the water absorbent polymer so that the water absorbent polymer enters a gap in fiber layers formed by the raising, and laminating the core-side first non-woven fabric and the core-side second non-woven fabric such that a fiber layer of the core-side first non-woven fabric and a fiber layer of the core-side second non-woven fabric oppose each other.

8. The method for producing a wearing article according to claim 1, wherein the producing of the absorber further includes providing an absorber elastic member so as to be capable of expanding and contracting in the width direction at a tip end portion on a side opposite to an end portion joined to the waist body of the absorber in the orthogonal direction.

9. The method for producing a wearing article according to claim 1, wherein the producing of the absorber further includes providing the second engagement portion over substantially an entirety of the width direction of a tip end portion of the back sheet on an outer surface of the tip end portion on a side opposite to the waist member of the back sheet in the orthogonal direction.

10. The method for producing a wearing article according to claim 1, wherein the producing of the waist member includes joining a waist elastic member to at least one of an inner sheet and an outer sheet so as to be capable of expanding and contracting along the width direction in a state of being sandwiched between the inner sheet extending in the width direction and the outer sheet extending in the width direction and covering an outer surface of the inner sheet, wherein the outer surface of the inner sheet faces away from the skin surface of the wearer when the wearing article is worn by the wearer, and performing a weakening treatment on the joint portion such that an elastic force of a core arrangement portion in which the core is arranged among joint portions of the waist body to which the absorber is joined becomes weaker than an elastic force of a part adjacent in the width direction to the core arrangement portion.

11. The method for producing a wearing article according to claim 10, wherein the producing of the waist member further includes disposing the inner sheet on the outer sheet so as to form an extending portion that protrudes in a direction away from the inner sheet beyond an edge portion of the inner sheet in the orthogonal direction, and covering an end portion in the orthogonal direction of the absorber by folding back the extending portion in the orthogonal direction.

12. The method for producing a wearing article according to claim 10, wherein the producing of the waist member further includes performing a weakening treatment on a part where one of the first engagement portions is disposed such that an elastic force of a part where the one of the first engagement portions is disposed in the waist body becomes weaker than an elastic force of a part adjacent in the width direction to the part.

13. The method for producing a wearing article according to claim 1, wherein in the producing of the waist member, a waist continuous body in which each waist body of a plurality of wearing articles is continuous in the width direction is prepared, and the waist continuous body is cut for each region corresponding to each waist body to produce the waist body, in the joining of the absorber to the joint portion of the waist body, the absorber is joined so as to extend from the joint portion in the orthogonal direction with respect to the joint portion in a region corresponding to each waist body in the waist continuous body, and the engaging of the first engagement portions and the second engagement portion with each other includes folding the absorber in two in the orthogonal direction so that the waist continuous body overlaps a tip end portion of the absorber in a state of holding the tip end portion on a side opposite to an end portion joined to the waist continuous body in the orthogonal direction of the absorber joined to the waist continuous body at a stage before the waist continuous body is cut into the waist body, and folding back both side portions of the waist body such that both end portions in the width direction of the waist body overlap with the tip end portion of the absorber at a stage after the waist continuous body is cut into the waist body.

14. The method for producing a wearing article according to claim 1, wherein the forming of the temporary fixing is performed prior to the first engagement portions and the second engagement portion becoming engaged with each other.

* * * * *